US007524883B2

(12) United States Patent
Agoulnik et al.

(10) Patent No.: US 7,524,883 B2
(45) Date of Patent: Apr. 28, 2009

(54) EPONEMYCIN AND EPOXOMICIN ANALOGS AND USES THEREOF

(75) Inventors: Sergei Agoulnik, Wilmington, MA (US); Kozo Akasaka, Belmont, MA (US); Frank Fang, Andover, MA (US); Jean-Christophe Harmange, Andover, MA (US); Lynn Hawkins, Concord, MA (US); Yimin Jiang, Londonderry, NH (US); Charles Johannes, Newbury, MA (US); Xiang-Yi Li, Andover, MA (US); Pamela McGuiness, Methuen, MA (US); Erin A. Murphy, Atkinson, NH (US); Shawn Schiller, Haverhill, MA (US); Mary Vermeulen, Ipswich, MA (US); Jiayi Wu, Brookline, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 468 days.

(21) Appl. No.: 10/501,120

(22) PCT Filed: Jan. 8, 2003

(86) PCT No.: PCT/US03/00390

§ 371 (c)(1),
(2), (4) Date: Dec. 20, 2004

(87) PCT Pub. No.: WO03/059898

PCT Pub. Date: Jul. 24, 2003

(65) Prior Publication Data

US 2005/0101781 A1 May 12, 2005

Related U.S. Application Data

(60) Provisional application No. 60/346,711, filed on Jan. 8, 2002, provisional application No. 60/373,011, filed on Apr. 16, 2002.

(51) Int. Cl.
*C07D 303/46* (2006.01)
*A61K 31/336* (2006.01)

(52) U.S. Cl. .................. 514/475; 514/307; 514/314; 514/414; 514/456; 514/457; 514/466; 546/146; 546/169; 548/467; 549/402; 549/405; 549/435; 549/548

(58) Field of Classification Search ................. 549/548, 549/402, 405, 435; 546/146, 169; 548/467; 514/314, 414, 457, 456, 466, 475, 307
See application file for complete search history.

(56) References Cited

U.S. PATENT DOCUMENTS 4,990,448 A 2/1991 Konishi et al. .............. 435/106
5,071,957 A 12/1991 Konishi et al. .............. 530/330

FOREIGN PATENT DOCUMENTS

| EP | 0 332 080 B1 | 9/1989 |
| EP | 0 411 660 A1 | 2/1991 |
| JP | 3-197492 | 8/1991 |
| JP | 5-286955 | 11/1993 |
| WO | WO 95/24914 | 9/1995 |
| WO | WO 96/13266 | 5/1996 |
| WO | WO 02/096933 | 12/2002 |
| WO | WO 03/033506 A1 | 4/2003 |

OTHER PUBLICATIONS

Adams, et al., "Proteasome Inhibitors: A Novel Class of Potent and Effective Antitumor Agents", *Cancer Research*; 59: 2615-2622, 1999.
Elofsson, et a., Towards subunit-specific proteasome inhibitors: synthesis and evaluation of peptide $\alpha',\beta'$-epoxyketones, *Chemistry & Biology*, 6(11): 811-822, 1999.
Gardner, et al., "Characterization of peptidyl boronic acid inhibitors of mammalian 20 S and 26 S proteasomes and their inhibition of proteasomesin cultured cells", *Biochem J.*, 346: 447-454, 2000.
Harding, et al., "Novel Dipeptide Aldehydes Are Proteasome Inhibitors and Block the MHC-I Antigen-Processing Pathway[1]", *The Journal of Immunology*, 155(4):1767-75, 1995.
Iqbal, et al., "Potent $\alpha$-Ketocarboyl and Boronic Ester Derived Ihibitors of Proteasome", *Bioorganic & Medicinal Chemistry Letters*, 6(3): 287-90, 1996.
Momose, et al., "Tyropeptins A and B, New Proteasome Inhibitors Produced by *Kitasatospora* sp. MK993-dF2. I. Taxonomy, Isolation, Physico-chemical Properties and Biological Activities", *Journal of Antibiotics*, 54(12): 997-1003, 2001.
Sin, et al., "Total Synthesis of the Potent Proteasome Inhibitor Epoxomicin: A Useful Tool For Understanding Proteasome Biology", *Bioorganic & Medicinal Chemistry Letters*, 9(15:, 2283-2288, 1999.
Sun, et al., "CEP1612, a Dipeptidyl Proteasome Inhibitor, Induces $p21^{WAF1}$ and $p27^{KIP1}$ Expression and Apoptosis and Inhibits the Growth of the Human Lung Adenocarcinoma A-549 in Nude Mice[1]", *Cancer Research*, 61(4): 1280-1284, 2001.
Hanada, et al., "Epoxomicin. A New Antitumor Agent Of Microbial Origin", *Journal of Antibiotics*, 45 (11): 1746-1752, 1992.
Koguchi, et al., "TMC-86A, B and TMC-96, New Proteasome Inhibitors from *Streptomyces* sp. TC 1084 and *Saccharothrix* sp. TC 1094 II. Physico-chemical Properties and Structure Determination", *Journal of Antibiotics*, 53 (1): 63-65, 2000.
Koguchi, et al., "TMC-89A and B, New Proteasome Inhibitors from *Streptomyces* sp. TC 1087", *Journal of Antibiotics*, 53 (9): 967-972, 2000.
Meng, et al., "Eponemycin Exerts Its Antitumor Effect through the Inhibition of Proteasome Function[1]", *Cancer Research*, 59: 2798-2801, 1999.
Meng, et al., "Epoxomicin, a potent and selective proteasome inhibitor, exhibits in vivo antiinflammatory activity", *Proc. Natl. Acad. Sci. USA*, 96: 10403-10408, 1999.
Myung, et al., "The Ubiquitin-Proteasome Pathway and Proteasome Inhibitors", *Medicinal Research Reviews*, 21 (4): 245-273, 2001.
Sugawara, et al., "Eponemycin† A New Antibiotic Active Against B16 Melanoma I. Production, Isolation, Structure And Biological Activity", *Journal of Antibiotics*, XLIII (1): 8-18, 1990.

*Primary Examiner*—Bernard Dentz
(74) *Attorney, Agent, or Firm*—Myers Bigel Sibley & Sajovec, PA

(57) ABSTRACT

The present invention provides compounds having formula (1): wherein $R_1$-$R_6$, A, J, D, E, G, Q, w, x, y, and z are as described generally and in classes and subclasses herein, and additionally provides pharmaceutical compositions thereof, and methods for the use thereof in the treatment of cancer and/or inflammatory disorders, and more generally as proteasome inhibitors.

52 Claims, 1 Drawing Sheet

EPONEMYCIN AND EPOXOMICIN ANALOGS AND USES THEREOF

PRIORITY CLAIM

The present application claims the benefit under 35 U.S.C. 0 371 of International Application No.: PCT/US03/00390 (published PCT application No. WO 03/59898), filed Jan. 8, 2003, which claims priority to U.S. patent application Ser. No. 60/346,711, filed Jan. 8, 2002, and U.S. patent application Ser. No. 60/373,011, filed Apr. 16, 2002, the entire contents of each of the above applications are incorporated herein by reference.

BACKGROUND OF THE INVENTION

Epoxomicin and Eponemycin, depicted below, are natural products isolated from unidentified *actinomycete* strain No. Q996-17 and from *streptomyces thiogroscopicus* No. P247-271, respectively (see, Hanada et al. *J. Antibiotics* 1992, 45, 1746-1752; Sugawara et al. *J. Antibiotics* 1990, 43, 8-18) that exhibit anti-tumor, and, in the case of epoxomicin, anti-inflammatory activity. Interestingly, both of these compounds have also been shown to bind covalently and irreversibly to the 20S proteasome (see, Sin et al. *Bioorg. Med. Chem. Lett.* 1999, 9, 2283-2288; Meng et al. *Proc. Nail. Acad. Sci. USA* 1999, 96, 10403-10408; Meng et al. *Cancer Res.* 1999, 59, 2798-2801).

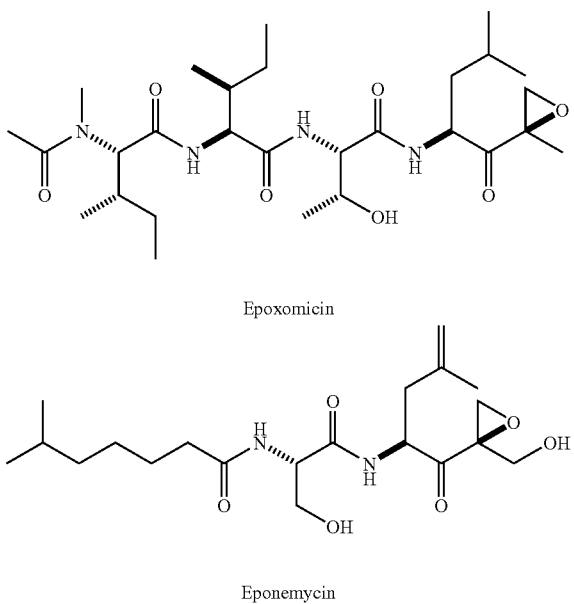

The ability of these natural products and other compounds to act as proteasome inhibitors has attracted significant interest because of the wide range of cellular substrates and processes controlled or affected by the ubiquitin-proteasome pathway. For example, the oscillation of cyclins (cell cycle proteins required for the orderly progression through the cell cycle) has been found to be due to the regulated degradation mediated by the ubiquitin-proteasome pathway, and inhibition of this pathway is believed to result in the blockage of cell cycle progression. Additionally, the transcription factor NF-κB is another regulatory protein involved in a variety of cellular processes, including immune and inflammatory responses, apoptosis, and cellular proliferation, whose mode of action is controlled by the ubiquitin-proteasome pathway. Furthermore, it has also been shown that the ubiquitin-proteasome pathway is involved in retrovirus assembly and thus may be a useful target for the development of anti-HIV drugs. For a general discussion of the ubiquitin-proteasome pathway and proteasome inhibitors see, Myung et al. "The Ubiquitin-Proteasome Pathway and Proteasome Inhibitors" *Medicinal Research Reviews* 2001, 21, 245-273.

As a result of the ability of the epoxyketones epoxomicin and eponemycin to inhibit the proteasome, there has been interest in developing the therapeutic potential of this class of compounds. Examples of other linear peptide epoxyketones that have been isolated recently on the basis of proteasome inhibition screening from microbial metabolites include TMC-86A, TMC-86B, TC 1084, TMC-89A and TMC-89B (see, Koguchi et al. *J. Antibiotics,* 2000, 53, 63-65; Koguchi et al. *J. Antibiotics* 2000, 53, 967-972). Additionally, certain synthetic epoxyketones have been prepared and investigated (Elofsson et al. *Chem. Biol.* 1999, 6, 811-822). Although there has been significant interest in the development of epoxyketones as proteasome inhibitors useful as potential therapeutics, there remains a need to prepare and investigate the biological activity of a wider range of analogues of this class of compounds. Clearly, it would be desirable to develop analogues that are safe and efficacious for the treatment of cancer, immune or inflammatory disorders, or HIV, to name a few. Additionally, it would be desirable to develop analogues that specifically target the ubiquitin-proteasome pathway.

SUMMARY OF THE INVENTION

As discussed above, there remains a need for the development of novel therapeutic agents and agents useful for treating disorders mediated by proteasomes. The present invention provides novel compounds of general formula (I),

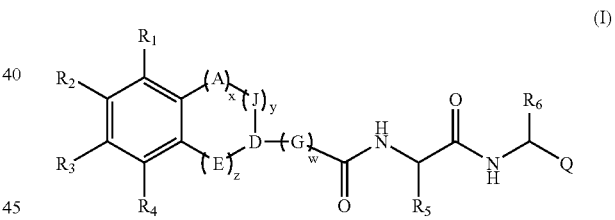

and pharmaceutical compositions thereof, as described generally and in subclasses herein, which compounds are useful as inhibitors of proteasomes, and thus are useful, for example, for the treatment of various disorders involving proteasome activity, including, for example, cancer, immune or inflammatory disorders, or HIV.

DESCRIPTION OF CERTAIN PREFERRED EMBODIMENTS OF THE INVENTION

Figure 1:
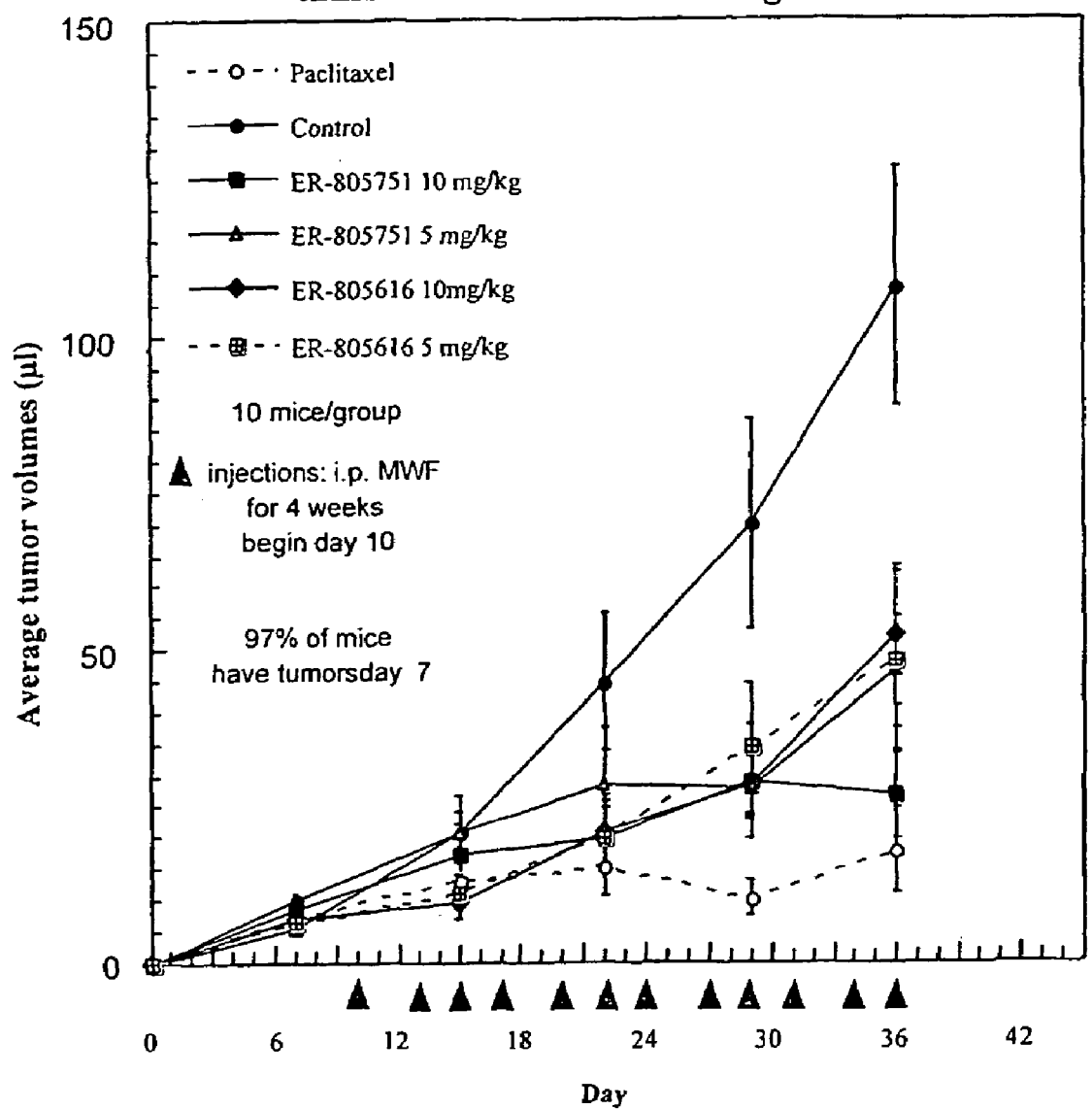
FIG. 1 is a graphical representation depicting comparative human breast carcinoma cell growth inhibition of Paclitaxel and exemplary inventive compounds.

As discussed above, the demonstrated antitumor and anti-inflammatory activity of the natural products epoxomicin and eponemycin, as well as their ability to inhibit the 20S proteasome, has led to increased interest in the synthesis and biological investigation of these compounds and, epoxyketones generally. In recognition of the need to further develop the therapeutic potential of this class of compounds, the present invention provides novel epoxomicin and eponemycin analogs. In certain embodiments, the compounds of the present invention can be used for the treatment of cancer and inflammatory disorders. More generally, in certain other embodiments, the compounds of the invention act as proteasome inhibitors.

1) General Description of Compounds of the Invention

The compounds of the invention include compounds of the general formula (I) as further defined below:

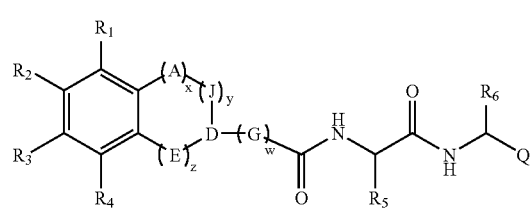

(I)

and pharmaceutically acceptable derivatives thereof;
wherein each occurrence of A, J, C, D and G is independently absent, $CR_A$, $CR_AR_B$, C=O, O, S, $NR_A$, or N, wherein each occurrence of $R_A$ and $R_B$ is independently hydrogen, a protecting group, or an aliphatic, alicyclic, heteroaliphatic, heteroalicyclic, aryl or heteroaryl moiety;

A and J, J and D, D and E, and D and G are each independently linked by a single or double bond as valency permits;

w, x, y and z are each independently 0, 1, 2, 3, 4, 5 or 6, but the sum of x, y and z is 0-6;

$R_1$, $R_2$, $R_3$ and $R_4$ are each independently hydrogen, halogen, —CN, —$OR_C$, —$SR_C$, —$NR_CR_D$, —(C=O)$R_C$ or an aliphatic, alicyclic, heteroaliphatic, heteroalicyclic, aryl or heteroaryl moiety, wherein each occurrence of $R_C$ and $R_D$ is independently hydrogen, a protecting group, or an aliphatic, alicyclic, heteroaliphatic, heteroalicyclic, aryl or heteroaryl moiety, or $R_C$ and $R_D$, taken together, form a heteroalicyclic or heteroaryl moiety; or wherein any two adjacent groups $R_1$, $R_2$, $R_3$ and $R_4$, taken together, form an alicyclic or heteroalicyclic moiety, or an aryl or heteroaryl moiety;

$R_5$ and $R_6$ are each independently an aliphatic, alicyclic, heteroaliphatic, heteroalicyclic, aryl or heteroaryl moiety; and Q is an O-containing heteroaliphatic or heteroalicyclic moiety.

In certain embodiments, the present invention defines certain classes of compounds which are of special interest. For example, one class of compounds of special interest includes those compounds of formula (I) wherein the compound has the stereochemistry as shown in Formula ($I^A$)

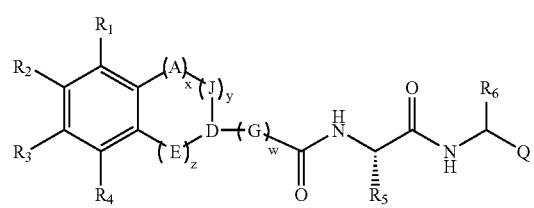

($I^A$)

Another class of compounds of special interest includes those compounds wherein the compound has the stereochemistry as shown in Formula ($I^B$):

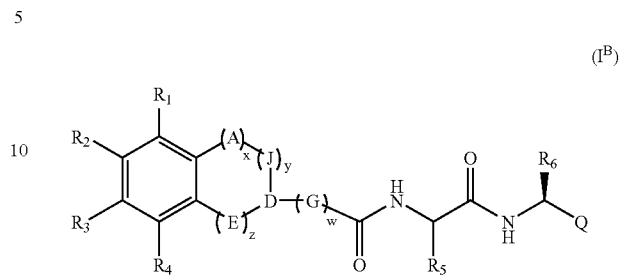

($I^B$)

Another class of compounds of special interest includes those compounds wherein the compound has the stereochemistry as shown in Formula ($I^C$):

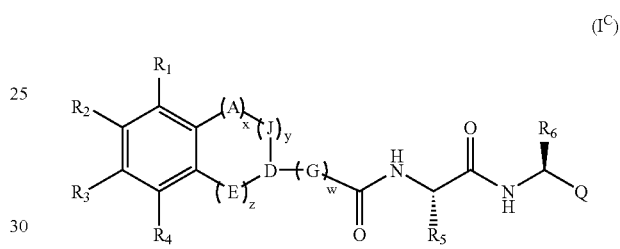

($I^C$)

Another class of compounds of special interest includes those compounds wherein, in the compound of formula (I) above, Q is an epoxycarbonyl moiety and the compound has the formula (II):

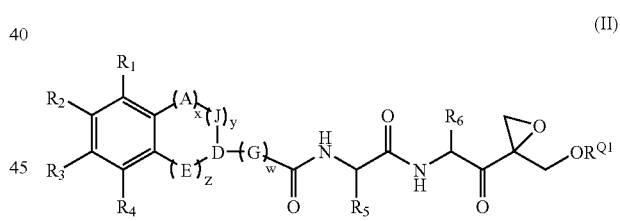

(II)

wherein $R^{Q1}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein the compound of formula (II) above has the stereochemistry shown in formula ($II^A$)

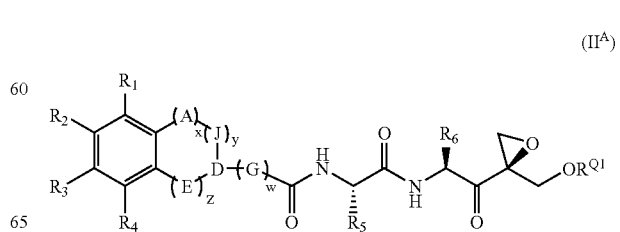

($II^A$)

Another class of compounds of special interest includes those compounds wherein, in the compound of formula (II) above, $R_5$ is —CH$_2$OR$_{5a}$ and the compound has the formula (II$^B$):

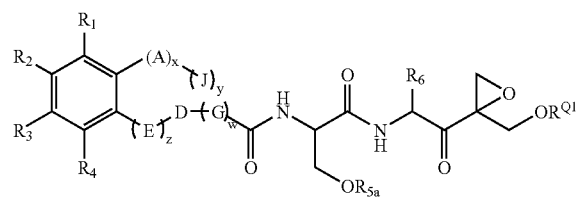

(II$^B$)

wherein R$_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (II) above, R$_5$ is aryl or heteroaryl and the compound has the formula (II$^C$):

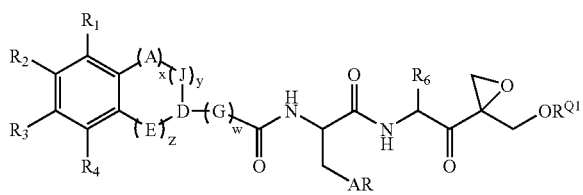

(II$^C$)

wherein AR is an aryl or heteroaryl moiety.

Another class of compounds of special interest includes those compounds wherein, in the compound of formula (II) above, R$_5$ is —CH$_2$NR$_{5a}$R$_{5b}$ and the compound has the formula (II$^D$):

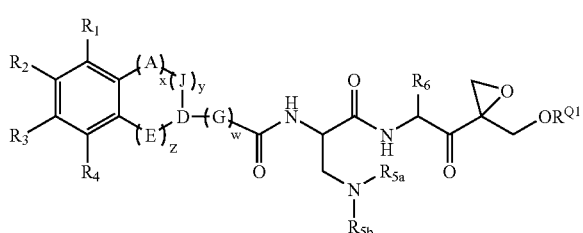

(II$^D$)

wherein R$_{5a}$ and R$_{5b}$ are each independently hydrogen, a nitrogen protecting group, an aliphatic, alicyclic, heteroaliphatic, heteroalicyclic, aryl or heteroaryl moiety, or a prodrug, or R$_{5a}$ and R$_{5b}$, taken together, form a heteroalicyclic or heteroaryl moiety.

Another class of compounds of special interest includes those compounds wherein, in the compound of formula (II) above, R$_6$ is —CH$_2$CH(CH$_3$)$_2$ and the compound has the formula (II$^E$):

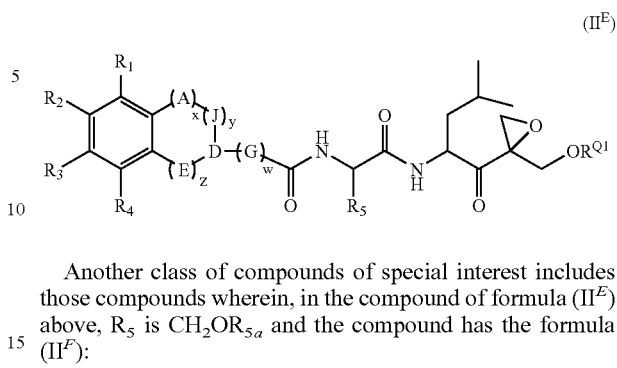

(II$^E$)

Another class of compounds of special interest includes those compounds wherein, in the compound of formula (II$^E$) above, R$_5$ is CH$_2$OR$_{5a}$ and the compound has the formula (II$^F$):

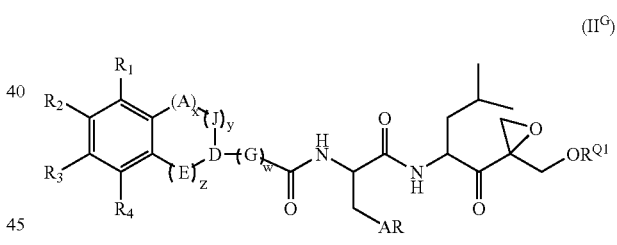

(II$^F$)

wherein R$_{5a}$ is hydrogen, an aliphatic, alicyclic, heteroaliphatic, heteroalicyclic, aryl or heteroaryl moiety, an oxygen protecting-group or a prodrug moiety.

Another class of compounds of special interest includes those compounds wherein, in the compound of formula (II$^E$) above, R$_5$ is aryl or heteroaryl and the compound has the formula (II$^G$):

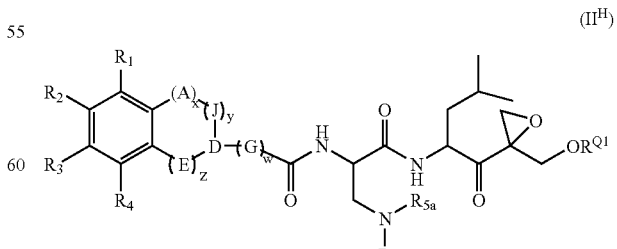

(II$^G$)

wherein AR is an aryl or heteroaryl moiety.

Another class of compounds of special interest includes those compounds wherein, in the compound of formula (II$^E$) above, R$_5$ is —CH$_2$NR$_{5a}$R$_{5b}$ and the compound has the formula (II$^H$):

(II$^H$)

wherein R$_{5a}$ and R$_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (I) above, Q is a boron-containing moiety and the compound has the formula (III):

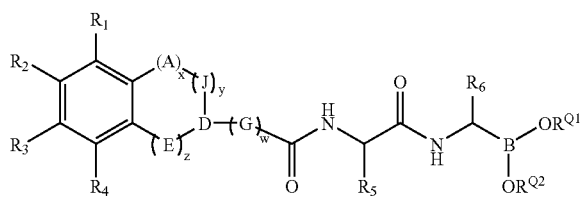

(III)

wherein $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety.

Another class of compounds of special interest includes those compounds wherein the compound of formula (III) above has the stereochemistry shown in formula (III$^A$):

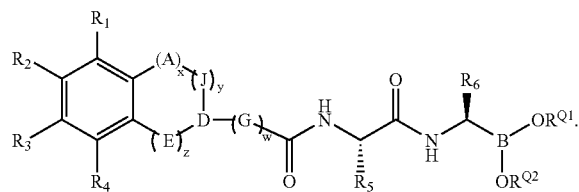

(III$^A$)

Another class of compounds of special interest includes those compounds wherein, in the compound of formula (III) above, $R_5$ is —$CH_2OR_{5a}$ and the compound has the formula (III$^B$):

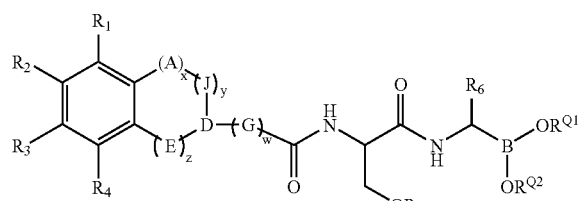

(III$^B$)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (III) above, $R_5$ is aryl or heteroaryl and the compound has the formula (III$^C$):

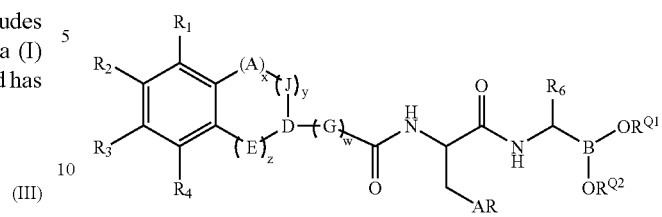

(III$^C$)

wherein AR is an aryl or heteroaryl moiety.

Another class of compounds of special interest includes those compounds wherein, in the compound of formula (III) above, $R_5$ is —$CH_2NR_{5a}R_{5b}$ and the compound has the formula (III$^D$):

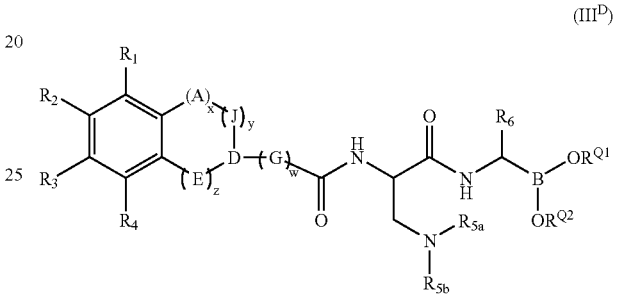

(III$^D$)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (III) above, $R_6$ is —$CH_2CH(CH_3)_2$ and the compound has the formula (III$^E$):

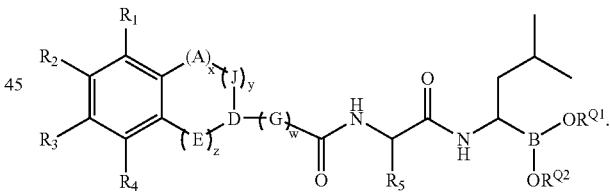

(III$^E$)

Another class of compounds of special interest includes those compounds wherein, in the compound of formula (III$^E$) above, $R_5$ is —$CH_2OR_{5a}$ and the compound has the formula (III$^F$):

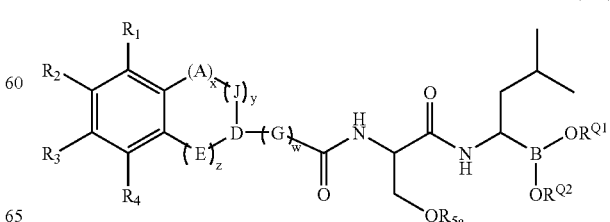

(III$^F$)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula ($III^E$) above, $R_5$ is aryl or heteroaryl and the compound has the formula ($III^G$):

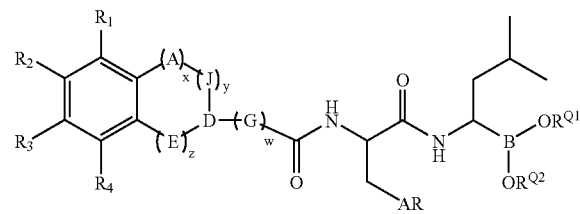

($III^G$)

wherein AR is an aryl or heteroaryl moiety.

Another class of compounds of special interest includes those compounds wherein, in the compound of formula ($III^E$) above, $R_5$ is —$CH_2NR_{5a}R_{5b}$ and the compound has the formula ($III^H$):

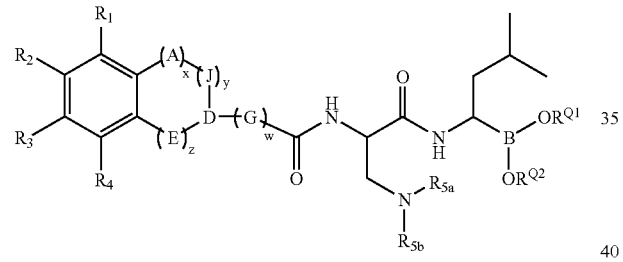

($III^H$)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (I) above, A, J, D, and E are each $CH_2$ and the compound has the structure of formula (IV):

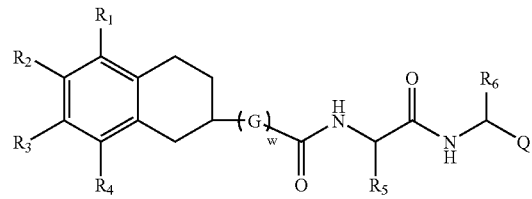

(IV)

Another class of compounds of special interest includes those compounds of formula (IV) above, wherein the compound has the stereochemistry as shown in Formula ($IV^A$):

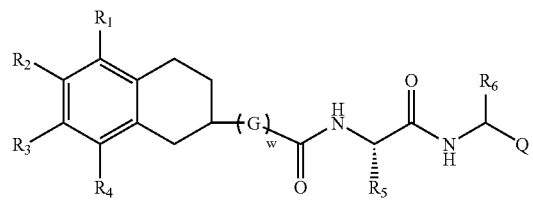

($IV^A$)

Another class of compounds of special interest includes those compounds of formula (IV) above, wherein the compound has the stereochemistry as shown in Formula ($IV^B$):

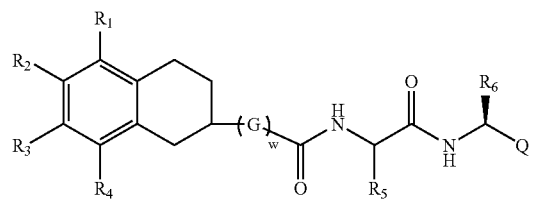

($IV^B$)

Another class of compounds of special interest includes those compounds of formula (IV) above, wherein the compound has the stereochemistry as shown in Formula ($IV^C$):

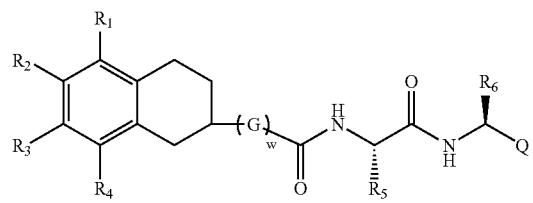

($IV^C$)

Another class of compounds of special interest includes those compounds wherein, in the compound of formula (IV) above, Q is an epoxycarbonyl moiety and the compound has the formula (V):

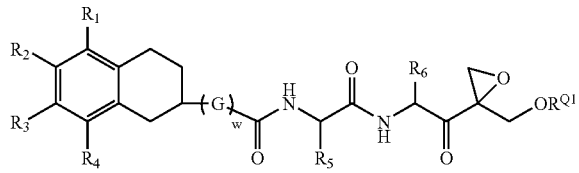

(V)

wherein $R^{Q1}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein the compound of formula (V) above has the stereochemistry shown in formula ($V^A$):

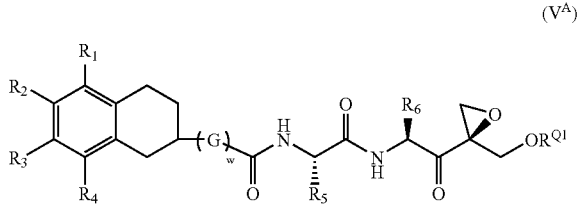

(V^A)

Another class of compounds of special interest includes those compounds wherein, in the compound of formula (V) above, $R_5$ is —$CH_2OR_{5a}$ and the compound has the formula (V^B):

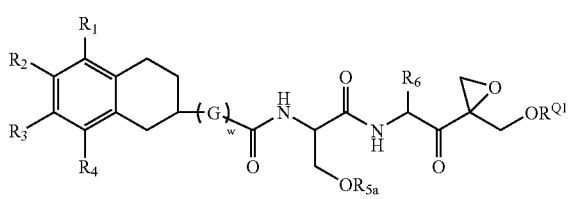

(V^B)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (V) above, $R_5$ is aryl or heteroaryl and the compound has the formula (V^C):

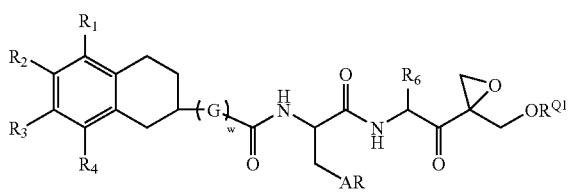

(V^C)

wherein AR is an aryl or heteroaryl moiety.

Another class of compounds of special interest includes those compounds wherein, in the compound of formula (V) above, $R_5$ is —$CH_2NR_{5a}R_{5b}$ and the compound has the formula (V^D):

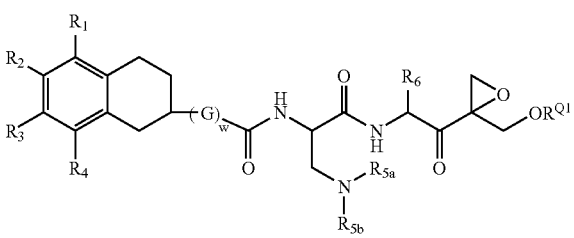

(V^D)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (V) above, $R_6$ is —$CH_2CH(CH_3)_2$ and the compound has the formula (V^E):

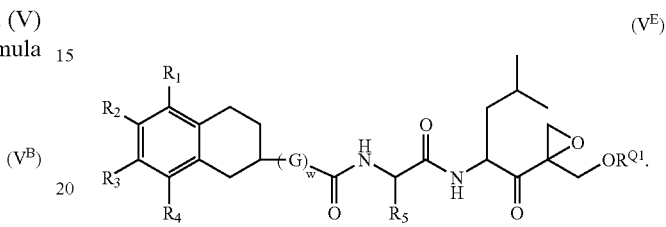

(V^E)

Another class of compounds of special interest includes those compounds wherein, in the compound of formula (V^E) above, $R_5$ is —$CH_2OR_{5a}$ and the compound has the formula (V^F):

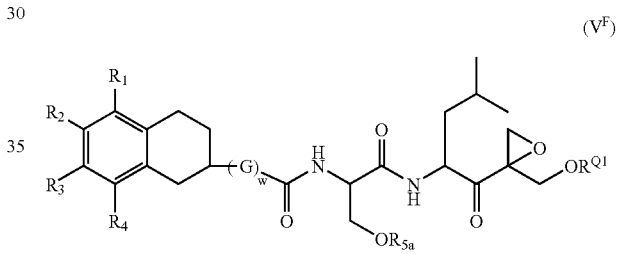

(V^F)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (V^E) above, $R_5$ is aryl or heteroaryl and the compound has the formula (V^G):

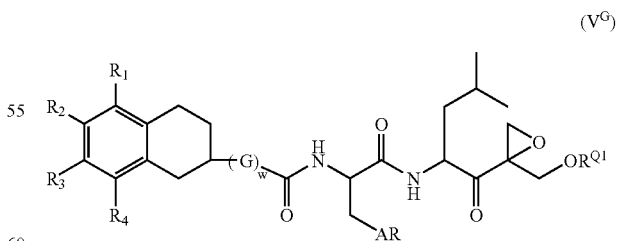

(V^G)

wherein AR is an aryl or heteroaryl moiety.

Another class of compounds of special interest includes those compounds wherein, in the compound of formula (V^E) above, $R_5$ is —$CH_2NR_{5a}R_{5b}$ and the compound has the formula (V^H):

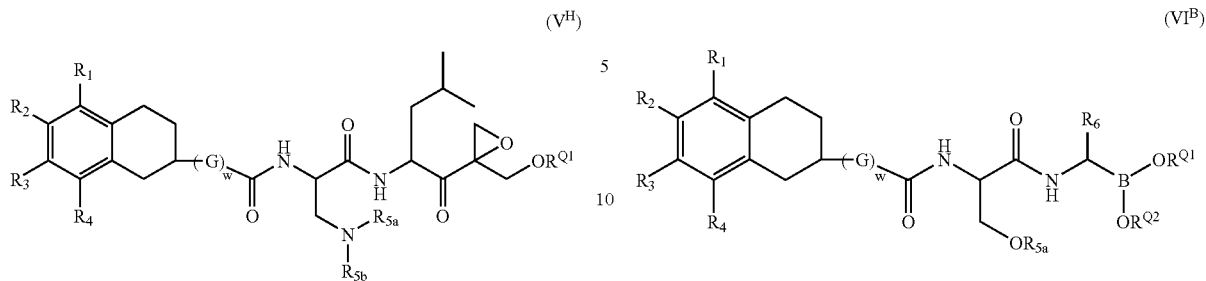
(V^H)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (IV) above, Q is a boron-containing moiety and the compound has the formula (VI):

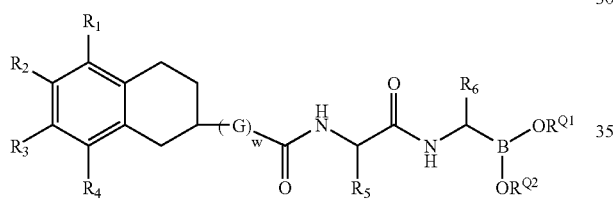
(VI)

wherein $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety.

Another class of compounds of special interest includes those compounds wherein the compound of formula (VI) above has the stereochemistry shown in formula (VI^A):

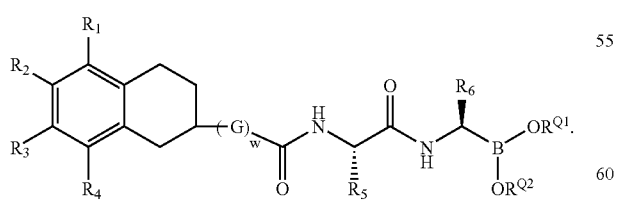
(VI^A)

Another class of compounds of special interest includes those compounds wherein, in the compound of formula (VI) above, $R_5$ is —CH$_2$OR$_{5a}$ and the compound has the formula (VI^B):

(VI^B)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (VI) above, $R_5$ is aryl or heteroaryl and the compound has the formula (VI^C):

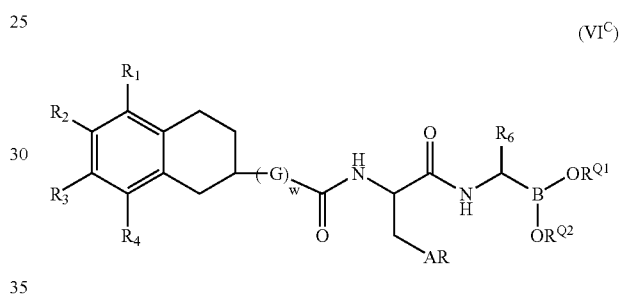
(VI^C)

wherein AR is an aryl or heteroaryl moiety.

Another class of compounds of special interest includes those compounds wherein, in the compound of formula (VI) above, $R_5$ is —CH$_2$NR$_{5a}$R$_{5b}$ and the compound has the formula (VI^D):

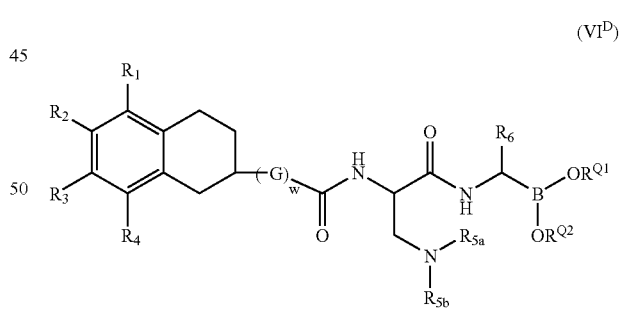
(VI^D)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (VI) above, $R_6$ is —CH$_2$CH(CH$_3$)$_2$ and the compound has the formula (VI^E):

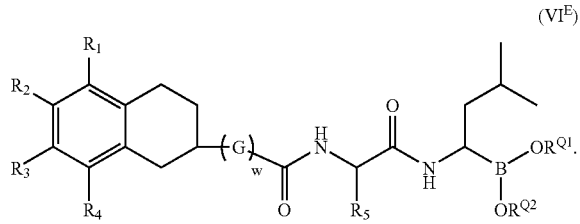

(VI^E)

Another class of compounds of special interest includes those compounds wherein, in the compound of formula (VI^E) above, $R_5$ is —CH$_2$OR$_{5a}$ and the compound has the formula (VI^F):

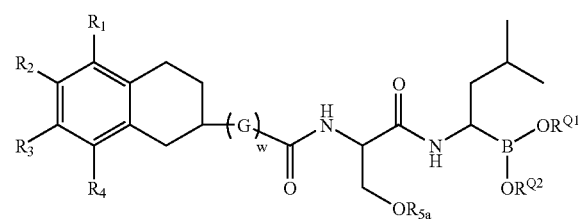

(VI^F)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (VI^E) above, $R_5$ is aryl or heteroaryl and the compound has the formula (VI^G):

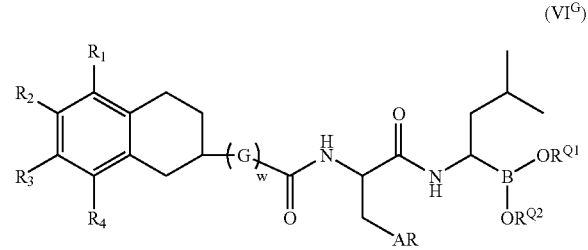

(VI^G)

wherein AR is an aryl or heteroaryl moiety.

Another class of compounds of special interest includes those compounds wherein, in the compound of formula (VI^E) above, $R_5$ is —CH$_2$NR$_{5a}$R$_{5b}$ and the compound has the formula (VI^H):

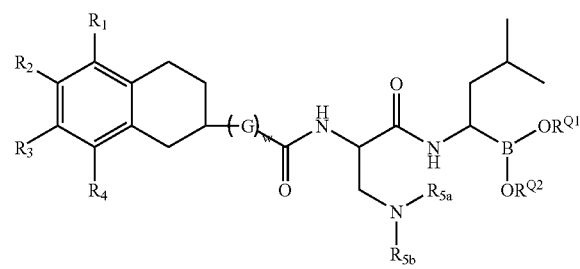

(VI^H)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest consists of compounds wherein, in the compound of formula (I) above, w, x and y are each 0 the compound has the formula (VII):

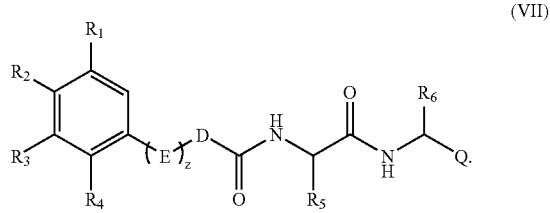

(VII)

Another class of compounds of special interest consists of those compounds of formula (VII) wherein the compound has the stereochemistry shown in formula (VII^A):

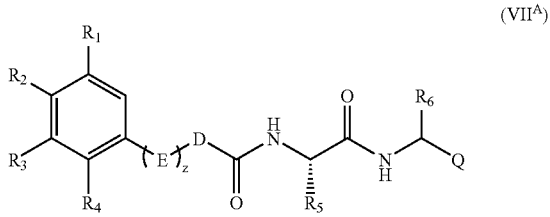

(VII^A)

Another class of compounds of special interest includes those compounds of formula (VII) wherein the compound has the stereochemistry shown in Formula (VII^B):

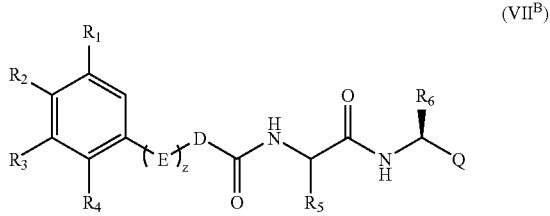

(VII^B)

Another class of compounds of special interest includes those compounds of formula (VII) wherein the compound has the stereochemistry shown in Formula (VII^C):

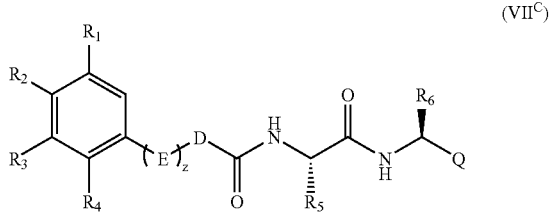

(VII^C)

Another class of compounds of special interest includes those compounds wherein, in the compound of formula (VII) above, Q is an epoxycarbonyl moiety and the compound has the formula (VIII):

(VIII)

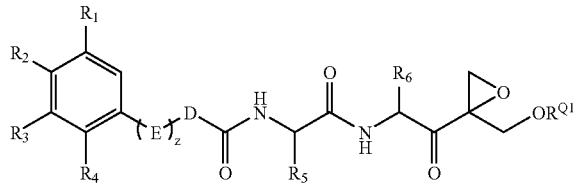

wherein $R^{Q1}$ is hydrogen, alkyl, aryl, heteroaryl, an oxygen protecting group or a prodrug moiety.

Another class of compounds of special interest includes those compounds wherein the compound of formula (VIII) above has the stereochemistry shown in formula (VIII$^A$):

(VIII$^A$)

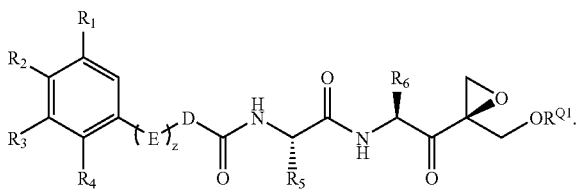

Another class of compounds of special interest includes those compounds wherein, in the compound of formula (VIII) above, $R_5$ is —CH$_2$OR$_{5a}$ and the compound has the formula (VIII$^B$):

(VIII$^B$)

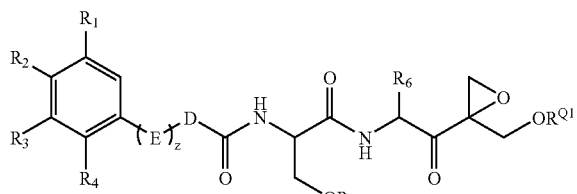

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (VIII) above, $R_5$ is aryl or heteroaryl and the compound has the formula (VIII$^C$):

(VIII$^C$)

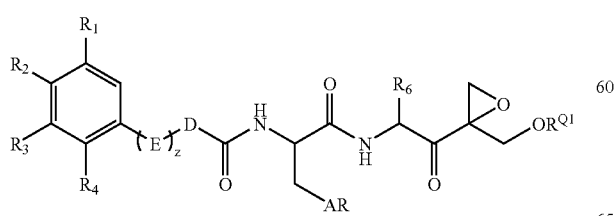

wherein AR is an aryl or heteroaryl moiety.

Another class of compounds of special interest includes those compounds wherein, in the compound of formula (VIII) above, $R_5$ is —CH$_2$NR$_{5a}$R$_{5b}$ and the compound has the formula (VIII$^D$):

(VIII$^D$)

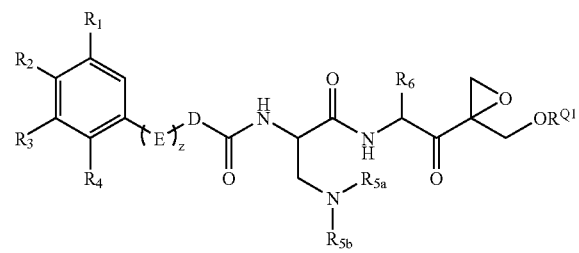

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (VIII) above, $R_6$ is —CH$_2$CH(CH$_3$)$_2$ and the compound has the formula (VIII$^E$):

(VIII$^E$)

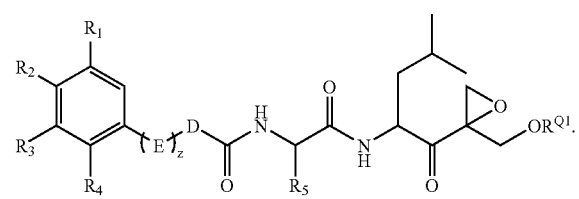

Another class of compounds of special interest includes those compounds wherein, in the compound of formula (VIII$^E$) above, $R_5$ is —CH$_2$OR$_{5a}$ and the compound has the formula (VIII$^F$):

(VIII$^F$)

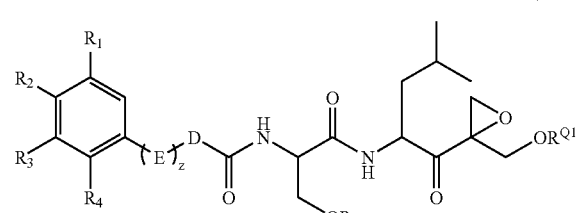

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (VIII$^E$) above, $R_5$ is aryl or heteroaryl and the compound has the formula (VIII$^G$):

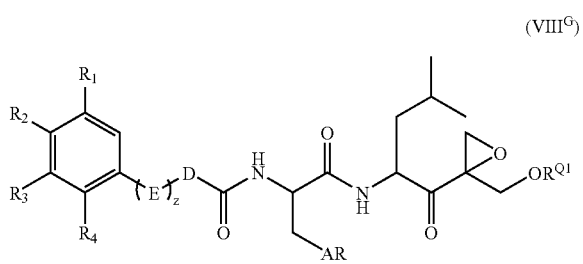
(VIII$^G$)

wherein AR is an aryl or heteroaryl moiety.

Another class of compounds of special interest includes those compounds wherein, in the compound of formula (VIII$^E$) above, R$_5$ is —CH$_2$NR$_{5a}$R$_{5b}$ and the compound has the formula (VIII$^H$):

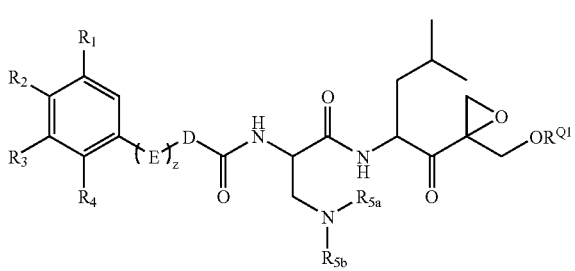
(VIII$^H$)

wherein R$_{5a}$ and R$_{5b}$ are each independently hydrogen, a nitrogen protecting group, an aliphatic, alicyclic, hetero aliphatic, heteroalicyclic, aryl or hetero aryl moiety, or a pro drug, or R$_{5a}$ and R$_{5b}$, taken together, form a heteroalicyclic or heteroaryl moiety.

Another class of compounds of special interest includes those compounds wherein, in the compound of formula (VII) above, Q is a boron-containing moiety and the compound has the formula (IX):

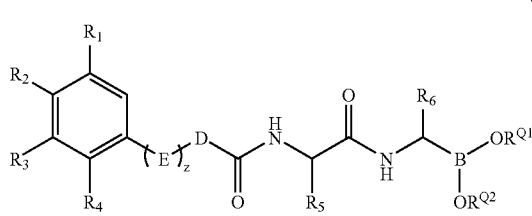
(IX)

wherein R$^{Q1}$ and R$^{Q2}$ are each independently hydrogen, an aliphatic, alicyclic, heteroaliphatic, heteroalicyclic, aryl or heteroaryl moiety, or an oxygen protecting group, or R$^{Q1}$ and R$^{Q2}$, taken together, form a heteroalicyclic moiety.

Another class of compounds of special interest includes those compounds wherein the compound of formula (IX) above has the stereochemistry shown in formula (IX$^A$):

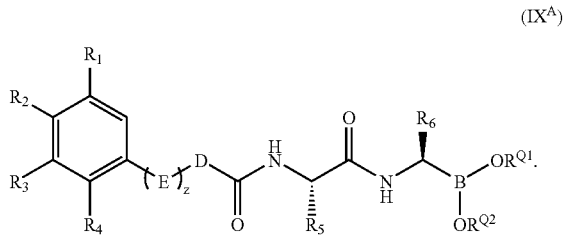
(IX$^A$)

Another class of compounds of special interest includes those compounds wherein, in the compound of formula (IX) above, R$_5$ is —CH$_2$OR$_{5a}$ and the compound has the formula (IX$^B$).

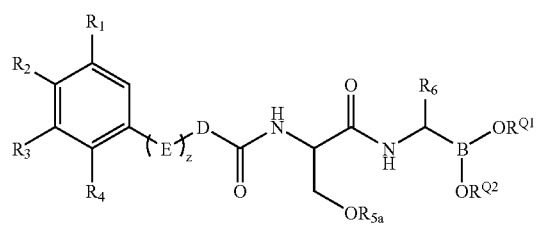
(IX$^B$)

wherein R$_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (IX) above, R$_5$ is aryl or heteroaryl and the compound has the formula (IX$^C$):

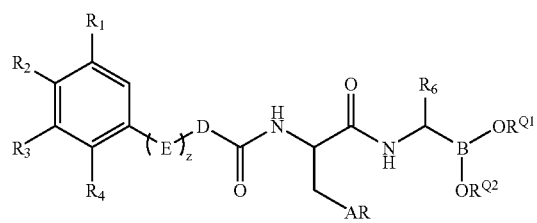
(IX$^C$)

wherein AR is an aryl or heteroaryl moiety.

Another class of compounds of special interest includes those compounds wherein, in the compound of formula (IX) above, R$_5$ is —CH$_2$NR$_{5a}$R$_{5b}$ and the compound has the formula (IX$^D$):

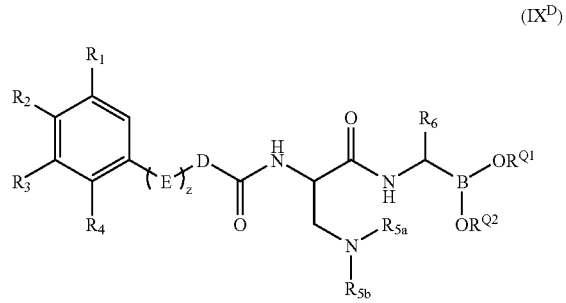
(IX$^D$)

wherein R$_{5a}$ and R$_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (IX) above, $R_6$ is —$CH_2CH(CH_3)_2$ and the compound has the formula ($IX^E$):

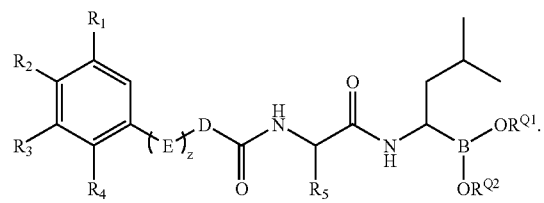

(IX$^E$)

Another class of compounds of special interest includes those compounds wherein, in the compound of formula ($IX^E$) above, $R_5$ is —$CH_2OR_{5a}$ and the compound has the formula ($IX^F$):

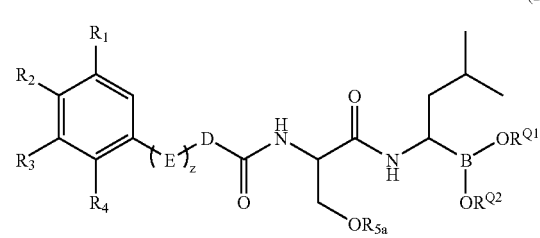

(IX$^F$)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula ($IX^E$) above, $R_5$ is aryl or heteroaryl and the compound has the formula ($IX^G$):

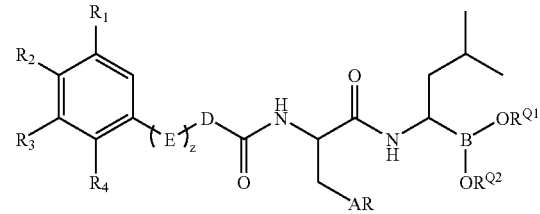

(IX$^G$)

wherein AR is an aryl or heteroaryl moiety.

Another class of compounds of special interest includes those compounds wherein, in the compound of formula ($IX^E$) above, $R_5$ is —$CH_2NR_{5a}R_{5b}$ and the compound has the formula ($IX^H$):

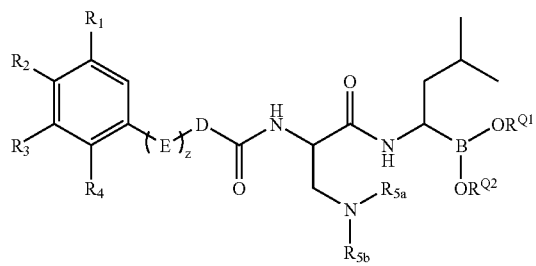

(IX$^H$)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest consists of compounds wherein, in the compound of formula (1) above, x, y, z and w are 0 and D is absent and the compound has the formula (X):

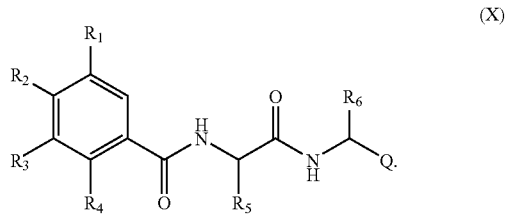

(X)

Another class of compounds of special interest consists of those compounds of formula (X) wherein the compound has the stereochemistry shown in formula ($X^A$):

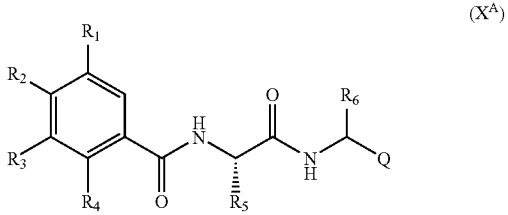

(X$^A$)

Another class of compounds of special interest includes those compounds of formula (X) wherein the compound has the stereochemistry shown in Formula ($X^B$):

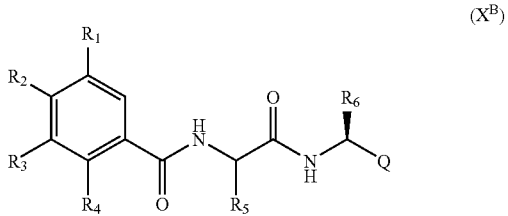

(X$^B$)

Another class of compounds of special interest includes those compounds of formula (X) wherein the compound has the stereochemistry shown in Formula ($X^C$):

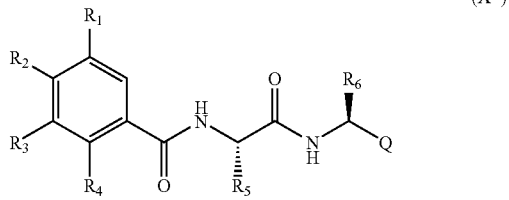

(X$^C$)

Another class of compounds of special interest includes those compounds wherein, in the compound of formula (X) above, Q is an epoxycarbonyl moiety and the compound has the formula (XI):

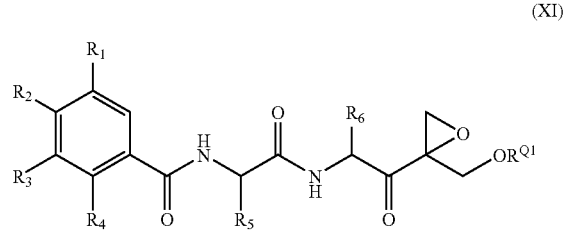

(XI)

wherein $R^{Q1}$ is hydrogen, alkyl, aryl, heteroaryl, an oxygen protecting group or a prodrug moiety.

Another class of compounds of special interest includes those compounds wherein the compound of formula (XI) above has the stereochemistry shown in formula ($XI^A$):

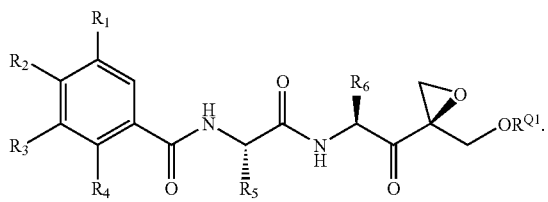

($XI^A$)

Another class of compounds of special interest includes those compounds wherein, in the compound of formula (XI) above, $R_5$ is —CH$_2$OR$_{5a}$ and the compound has the formula ($XI^B$):

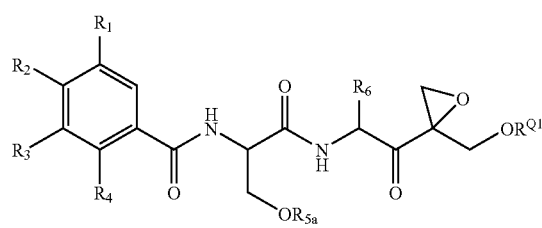

($XI^B$)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (XI) above, $R_5$ is aryl or heteroaryl and the compound has the formula ($XI^C$):

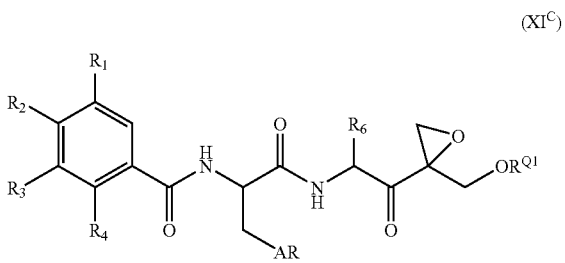

($XI^C$)

wherein AR is an aryl or heteroaryl moiety.

Another class of compounds of special interest includes those compounds wherein, in the compound of formula (XI) above, $R_5$ is —CH$_2$NR$_{5a}$R$_{5b}$ and the compound has the formula ($XI^D$):

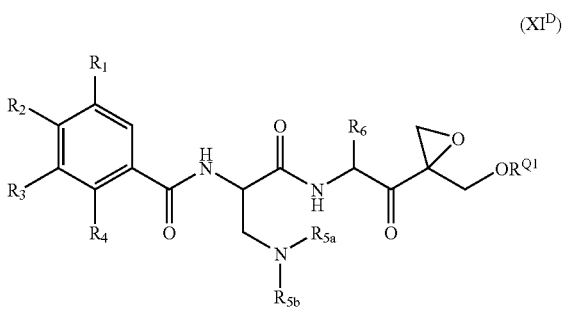

($XI^D$)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (XI) above, $R_6$ is —CH$_2$CH(CH$_3$)$_2$ and the compound has the formula ($XI^E$):

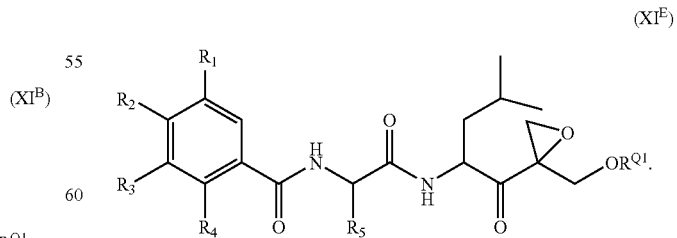

($XI^E$)

Another class of compounds of special interest includes those compounds wherein, in the compound of formula ($XI^E$) above, $R_5$ is —CH$_2$OR$_{5a}$ and the compound has the formula ($XI^F$):

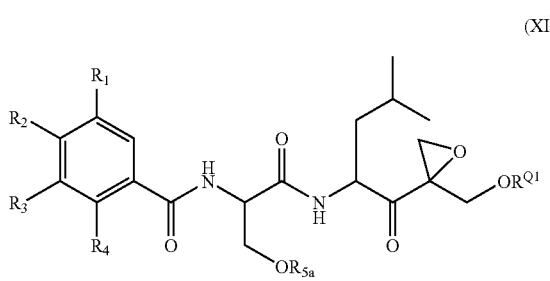

(XI$^F$)

wherein R$_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (XI$^E$) above, R$_5$ is aryl or heteroaryl and the compound has the formula (XI$^G$):

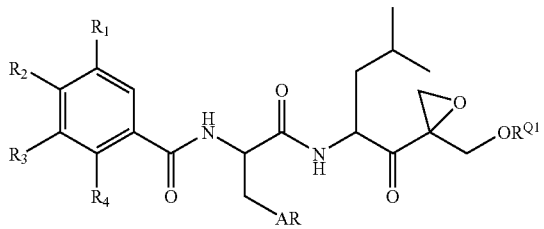

(XI$^G$)

wherein AR is an aryl or heteroaryl moiety.

Another class of compounds of special interest includes those compounds wherein, in the compound of formula (XI$^E$) above, R$_5$ is —CH$_2$NR$_{5a}$R$_{5b}$ and the compound has the formula (XI$^H$):

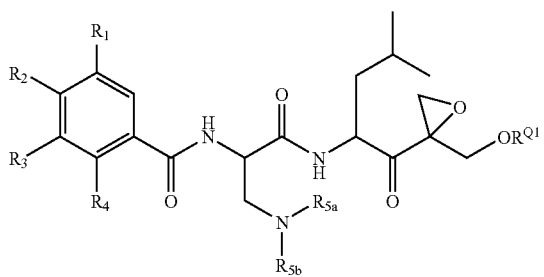

(XI$^H$)

wherein R$_{5a}$ and R$_{5b}$ are each independently hydrogen, a nitrogen protecting group, an aliphatic, alicyclic, heteroaliphatic, heteroalicyclic, aryl or heteroaryl moiety, or a prodrug, or R$_{5a}$ and R$_{5b}$, taken together, form a heteroalicyclic or heteroaryl moiety.

Another class of compounds of special interest includes those compounds wherein, in the compound of formula (X) above, Q is a boron-containing moiety and the compound has the formula (XII):

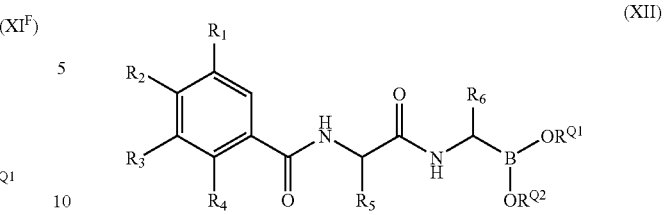

(XII)

wherein R$^{Q1}$ and R$^{Q2}$ are each independently hydrogen, an aliphatic, alicyclic, heteroaliphatic, heteroalicyclic, aryl or heteroaryl moiety, or an oxygen protecting group, or R$^{Q1}$ and R$^{Q2}$, taken together, form a heteroalicyclic moiety.

Another class of compounds of special interest includes those compounds wherein the compound of formula (XII) above has the stereochemistry shown in formula (XII$^A$):

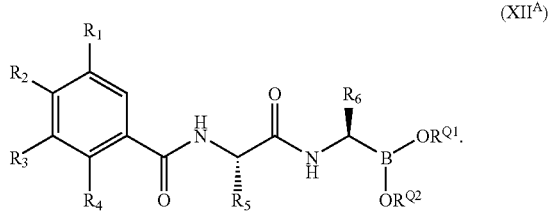

(XII$^A$)

Another class of compounds of special interest includes those compounds wherein, in the compound of formula (XII) above, R$_5$ is —CH$_2$OR$_{5a}$ and the compound has the formula (XII$^B$):

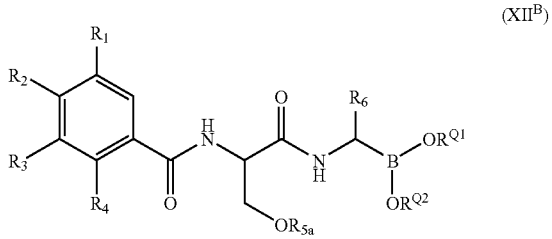

(XII$^B$)

wherein R$_{5a}$ is hydrogen, an aliphatic, alicyclic, heteroaliphatic, heteroalicyclic, aryl or heteroaryl moiety, an oxygen protecting group or a prod rug moiety.

Another class of compounds of special interest includes those compounds wherein, in the compound of formula (XII) above, R$_5$ is aryl or heteroaryl and the compound has the formula (XII$^C$):

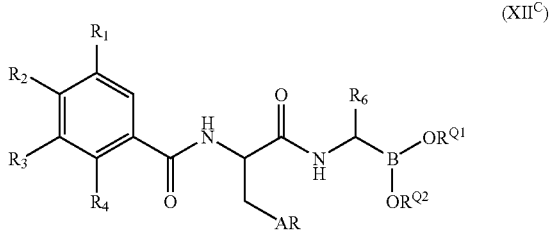

(XII$^C$)

wherein AR is an aryl or heteroaryl moiety.

Another class of compounds of special interest includes those compounds wherein, in the compound of formula (XII) above, R$_5$ is —CH$_2$NR$_{5a}$R$_{5b}$ and the compound has the formula (XII$^D$):

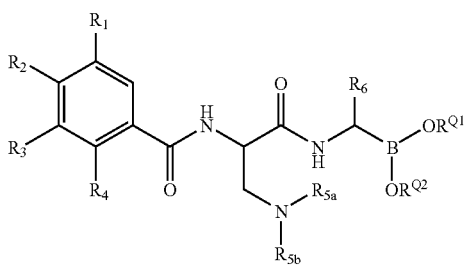

(XII^D)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

Another class of compounds of special interest includes those compounds wherein, in the compound of formula (XII) above, $R_6$ is —CH$_2$CH(CH$_3$)$_2$ and the compound has the formula (XII$^E$):

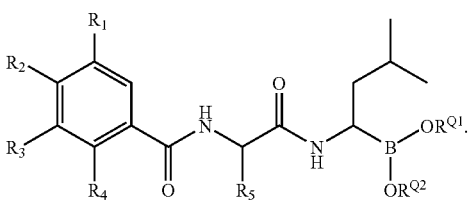

(XII^E)

Another class of compounds of special interest includes those compounds wherein, in the compound of formula (XII$^E$) above, $R_5$ is —CH$_2$OR$_{5a}$ and the compound has the formula (XII$^F$):

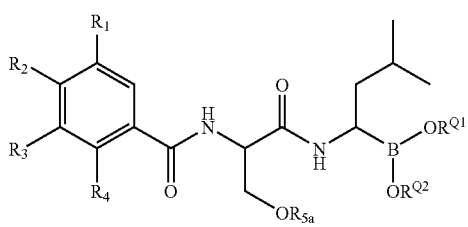

(XII^F)

wherein $R_{5a}$ is hydrogen, an aliphatic, alicyclic, heteroaliphatic, heteroalicyclic, aryl or heteroaryl moiety, an oxygen protecting group or a prodrug moiety.

Another class of compounds of special interest includes those compounds wherein, in the compound of formula (XII$^E$) above, $R_5$ is aryl or heteroaryl and the compound has the formula (XII$^G$):

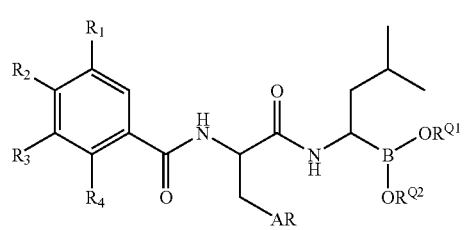

(XII^G)

wherein AR is an aryl or heteroaryl moiety.

Another class of compounds of special interest includes those compounds wherein, in the compound of formula (XII$^E$) above, $R_5$ is —CH$_2$NR$_{5a}$R$_{5b}$ and the compound has the formula (XII$^H$):

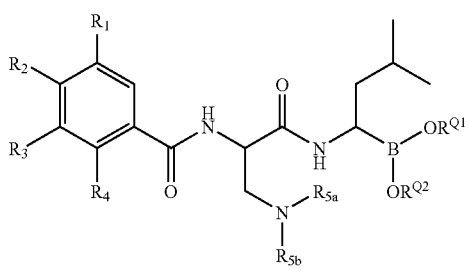

(XII^H)

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

A number of important subclasses of each of the foregoing classes deserve separate mention; these subclasses include subclasses of the foregoing classes in which:

i) G is CH$_2$ and w is 0, 1, or 2;

ii) x, y and z are each 1 and A, J, D and E are each —CH$_2$—;

iii) x, y and z are each 1 and A-J-D-E together represent —CH$_2$—CH$_2$—CH$_2$—CH$_2$—;

iv) x is 0 and A is absent, y and z are each 1, and J-D-E together represent —CH$_2$—CH$_2$—CH$_2$—;

v) x is 0 and A is absent, z is 0 and E is absent, and J-D together represents —CH$_2$—CH$_2$—;

vi) x, y and z are each 1 and A-J-D-E together represent —N=CH—CH=N—;

vii) x, y and z are each 1 and A-J-D-E together represent —CH$_2$—CH$_2$—CH$_2$—CH$_2$— and G is CH$_2$ and w is 0, 1 or 2;

viii) x, y and z are each 0 and D is absent;

ix) $R_1$, $R_2$, $R_3$ and $R_4$ are each independently hydrogen, halogen, protected or unprotected hydroxyl, protected or unprotected thiol, protected or unprotected amino, alkyl, alkoxy, thioalkyl, mono-or di-substituted alkylamino, or wherein any two adjacent groups $R_1$, $R_2$, $R_3$ or $R_4$, taken together are a cycloalkyl, heterocycloalkyl, aryl or heteroaryl moiety, whereby each of the alkyl moieties is independently substituted or unsubstituted, linear or branched, cyclic or acyclic, and each of the aryl and heteroaryl moieties is independently substituted or unsubstituted;

x) $R_1$, $R_2$, $R_3$ and $R_4$ are each independently hydrogen or lower alkoxy;

xi) $R_1$, $R_2$, $R_3$ and $R_4$ are each independently hydrogen or methoxy;

xii) $R_1$, $R_2$, $R_3$ and $R_4$ are each independently methoxy;

xiii) $R_1$ is hydrogen and each of $R_2$, $R_3$ and $R_4$ are independently lower alkoxy;

xiv) $R_1$ is hydrogen and each of $R_2$, $R_3$ and $R_4$ are methoxy;

xv) $R_5$ is alkyl, cycloalkyl, alkenyl, cycloalkenyl, alkynyl, cycloalkynyl, C$_{1-6}$OR$_{5a}$, C$_{1-6}$NR$_{5a}$R$_{5b}$, aryl or heteroaryl; wherein $R_{5a}$ and $R_{5b}$ are each independently hydrogen, alkyl, alkenyl, alkynyl, cycloalkyl, cycloalkenyl, aryl, heteroaryl, —C(NH$_2$)=N(NO$_2$), —C(=O)OR$_{5c}$, —C(=O)R$_{5c}$ or a protecting group; wherein R$_{5c}$ is hydrogen, alkyl, alkenyl, alkynyl, aryl or heteroaryl;

xvi) R$_5$ is alkyl, cycloalkyl, —CH$_2$OR$_{5a}$, —CH$_2$NR$_{5a}$R$_{5b}$, —CH$_2$aryl or —CH$_2$heteroaryl; wherein R$_{5a}$ and R$_{5b}$ are each independently hydrogen, alkyl, alkenyl, alkynyl, cycloalkyl, cycloalkenyl, aryl, heteroaryl, —C(NH$_2$)=N(NO$_2$), —C(=O)OR$_{5c}$, —C(=O)R$_{5c}$ or a protecting group; wherein R$_5$C is hydrogen, alkyl, alkenyl, alkynyl, aryl or heteroaryl;

xvii) R$_5$ is alkyl, cycloalkyl, CH$_2$OR$_{5a}$, CH$_2$NR$_{5a}$R$_{5b}$ or substituted or unsubstituted —CH$_2$Ph; wherein R$_{5a}$ and R$_{5b}$ are each independently hydrogen, alkyl, alkenyl, alkynyl, cycloalkyl, cycloalkenyl, aryl, heteroaryl, —C(NH$_2$)=N(NO$_2$), —C(=O)OR$_{5c}$, —C(=O)R$_5$, or a protecting group; wherein R$_{5c}$ is hydrogen, alkyl, alkenyl, alkynyl, aryl or heteroaryl;

xviii) R$_5$ is —CH$_2$OH or benzyl;

xix) R$_6$ is alkyl, cycloalkyl, alkenyl, cycloalkenyl, alkynyl, cycloalkynyl, aryl or heteroaryl;

xx) R$_6$ is lower alkyl or aryl;

xxi) R$_6$ is —CH$_2$CH(CH$_3$)$_2$;

xxii) Q is an epoxycarbonyl moiety;

xxiii) Q is an epoxycarbonyl moiety having the structure:

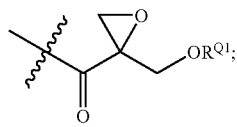

wherein R$^{Q1}$ is hydrogen, alkyl, aryl, heteroaryl, an oxygen protecting group or a prodrug moiety;

xxiv) Q is an epoxycarbonyl moiety having the structure:

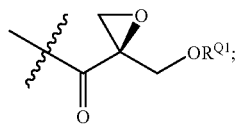

wherein R$^{Q1}$ is hydrogen, alkyl, aryl, heteroaryl, an oxygen protecting group or a prodrug moiety;

xxv) Q is an epoxycarbonyl moiety having the structure:

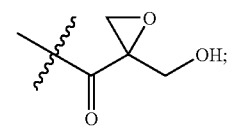

xxvi) Q is an epoxycarbonyl moiety having the structure:

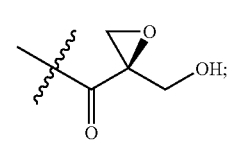

xxvii) Q is a Boron-containing moiety;

xxviii) Q is —B(OH)$_2$;

xxix) Q is a Boron-containing moiety having the structure:

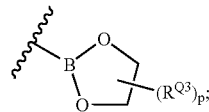

wherein R$^{Q3}$ is lower alkyl and p is an integer from 0-4; and xxxi) Q is a Boron-containing moiety having the structure:

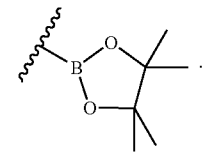

As the reader will appreciate, compounds of particular interest include, among others, those which share the attributes of one or more of the foregoing subclasses. Some of those subclasses are illustrated by the following sorts of compounds:

I) Compounds of the Formula (and Pharmaceutically Acceptable Derivatives Thereof):

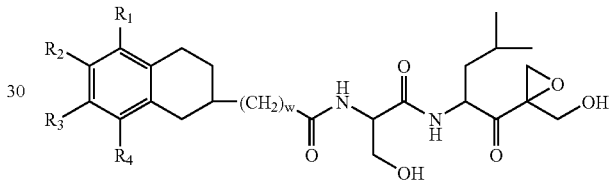

wherein w is 0, 1 or 2; and R$_1$, R$_2$, R$_3$ and R$_4$ are each independently hydrogen, OR$_C$, halogen, or NR$_C$R$_D$, wherein each occurrence of R$_C$ and R$_D$ is independently hydrogen or lower alkyl.

In certain embodiments, each of R$_1$, R$_2$, R$_3$ and R$_4$ is a substituent other than hydrogen.

In certain other embodiments, one of R$_1$, R$_2$, R$_3$ or R$_4$ is hydrogen, and each of the other groups is substituted with a substituent other than hydrogen.

In still other embodiments, two of R$_1$, R$_2$, R$_3$, or R$_4$ are hydrogen, and the other two are substituted with a substituent other than hydrogen.

In yet other embodiments, three of R$_1$, R$_2$, R$_3$ or R$_4$ are hydrogen, and the remaining group is substituted with a substituent other than hydrogen.

In certain other embodiments, w is 0 or 1. In still other embodiments, one or more of R$_1$-R$_4$ is OR$_C$, where R$_C$ is lower alkyl.

II) Compounds of the Formula (and Pharmaceutically Acceptable Derivatives Thereof):

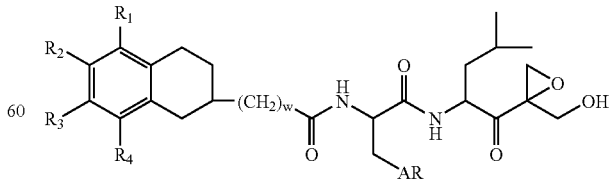

wherein AR is an aryl or heteroaryl moiety; w is 0, 1 or 2; and R$_1$, R$_2$, R$_3$ and R$_4$ are each independently hydrogen, OR$_C$, halogen, or NR$_C$R$_D$, wherein each occurrence of R$_C$ and R$_D$ is independently hydrogen or lower alkyl.

In certain embodiments, AR is substitued or unsubstituted phenyl.

In certain embodiments, each of $R_1$, $R_2$, $R_3$ and $R_4$ is a substituent other than hydrogen.

In certain other embodiments, one of $R_1$, $R_2$, $R_3$ or $R_4$ is hydrogen, and each of the other groups is substituted with a substituent other than hydrogen.

In still other embodiments, two of $R_1$, $R_2$, $R_3$, or $R_4$ are hydrogen, and the other two are substituted with a substituent other than hydrogen.

In yet other embodiments, three of $R_1$, $R_2$, $R_3$ or $R_4$ are hydrogen, and the remaining group is substituted with a substituent other than hydrogen.

In certain other embodiments, w is 0 or 1. In still other embodiments, one or more of $R_1$-$R_4$ is $OR_C$, where $R_C$ is lower alkyl.

III) Compounds of the Formula (and Pharmaceutically Acceptable Derivatives Thereof):

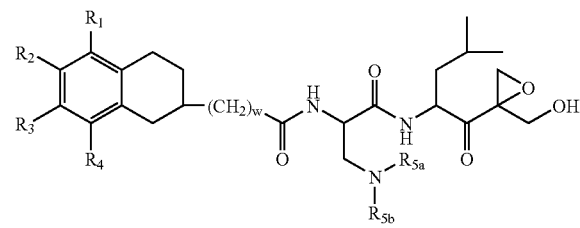

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety; w is 0, 1 or 2; and $R_1$, $R_2$, $R_3$ and $R_4$ are each independently hydrogen, $OR_C$, halogen, or $NR_CR_D$, wherein each occurrence of $R_C$ and $R_D$ is independently hydrogen or lower alkyl.

In certain embodiments, $R_{5a}$ and $R_{5b}$ are each independently hydrogen, —C(NH$_2$)=N(NO$_2$), —C(=O)OR$_{5c}$, —C(=O)R$_{5c}$, wherein $R_{5c}$ is alkyl, alkenyl, aryl or heteroaryl.

In certain embodiments, each of $R_1$, $R_2$, $R_3$ and $R_4$ is a substituent other than hydrogen.

In certain other embodiments, one of $R_1$, $R_2$, $R_3$ or $R_4$ is hydrogen, and each of the other groups is substituted with a substituent other than hydrogen.

In still other embodiments, two of $R_1$, $R_2$, $R_3$, or $R_4$ are hydrogen, and the other two are substituted with a substituent other than hydrogen.

In yet other embodiments, three of $R_1$, $R_2$, $R_3$ or $R_4$ are hydrogen, and the remaining group is substituted with a substituent other than hydrogen.

In certain other embodiments, w is 0 or 1. In still other embodiments, one or more of $R_1$-$R_4$ is $OR_C$, where $R_C$ is lower alkyl.

IV) Compounds of the Formula (and Pharmaceutically Acceptable Derivatives Thereof):

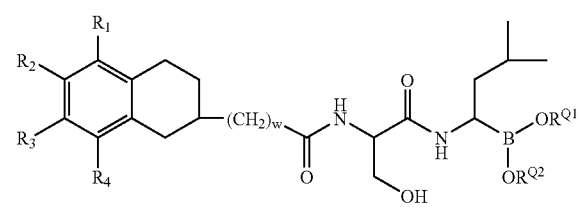

wherein $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2; and $R_1$, $R_2$, $R_3$ and $R_4$ are each independently hydrogen, $OR_C$, halogen, or $NR_CR_D$, wherein each occurrence of $R_C$ and $R_D$ is independently hydrogen or lower alkyl.

In certain embodiments, $R^{Q1}$ and $R^{Q2}$ are each independently hydrogen, lower alkyl, or, taken together, form a 5- to 6-membered alicyclic moiety.

In certain embodiments, each of $R_1$, $R_2$, $R_3$ and $R_4$ is a substituent other than hydrogen.

In certain other embodiments, one of $R_1$, $R_2$, $R_3$ or $R_4$ is hydrogen, and each of the other groups is substituted with a substituent other than hydrogen.

In still other embodiments, two of $R_1$, $R_2$, $R_3$, or $R_4$ are hydrogen, and the other two are substituted with a substituent other than hydrogen.

In yet other embodiments, three of $R_1$, $R_2$, $R_3$ or $R_4$ are hydrogen, and the remaining group is substituted with a substituent other than hydrogen.

In still other embodiments, the compound has the structure:

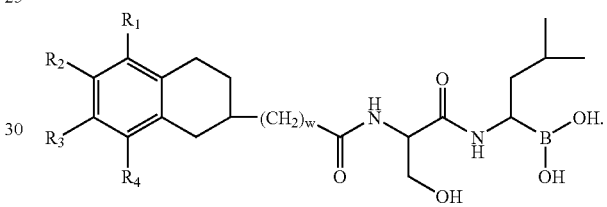

In yet other embodiments, the compound has the structure:

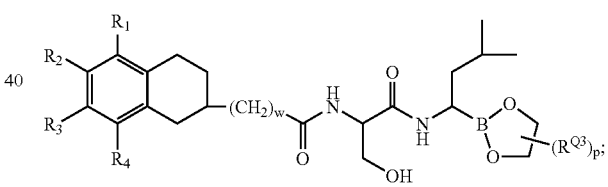

wherein $R^{Q3}$ is lower alkyl and p is an integer from 0-4.

In certain other embodiments, $R^{Q3}$ is methyl and p is 4.

In certain other embodiments, w is 0 or 1. In still other embodiments, one or more of $R_1$-$R_4$ is $OR_C$, where $R_C$ is lower alkyl.

V) Compounds of the Formula (and Pharmaceutically Acceptable Derivatives Thereof):

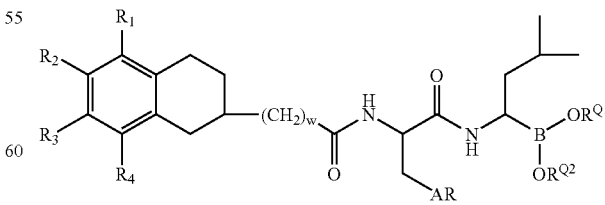

wherein AR is an aryl or heteroaryl moiety; $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2; and $R_1$, $R_2$, $R_3$ and $R_4$ are each independently hydrogen, $OR_C$, halogen, or $NR_CR_D$, wherein each occurrence of $R_C$ and RD is independently hydrogen or lower alkyl.

In certain embodiments, AR is substitued or unsubstituted phenyl.

In certain embodiments, $R^{Q1}$ and $R^{Q2}$ are each independently hydrogen, lower alkyl, or, taken together, form a 5- to 6-membered alicyclic moiety.

In certain embodiments, each of $R_1$, $R_2$, $R_3$ and $R_4$ is a substituent other than hydrogen.

In certain other embodiments, one of $R_1$, $R_2$, $R_3$ or $R_4$ is hydrogen, and each of the other groups is substituted with a substituent other than hydrogen.

In still other embodiments, two of $R_1$, $R_2$, $R_3$, or $R_4$ are hydrogen, and the other two are substituted with a substituent other than hydrogen.

In yet other embodiments, three of $R_1$, $R_2$, $R_3$ or $R_4$ are hydrogen, and the remaining group is substituted with a substituent other than hydrogen.

In still other embodiments, the compound has the structure:

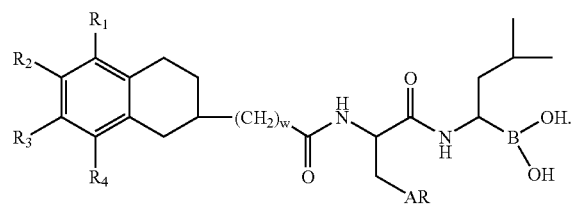

In yet other embodiments, the compound has the structure:

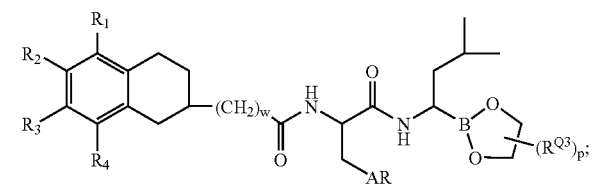

wherein $R^{Q3}$ is lower alkyl and p is an integer from 0-4.

In certain other embodiments, $R^{Q3}$ is methyl and p is 4.

In certain other embodiments, w is 0 or 1. In still other embodiments, one or more of $R_1$-$R_4$ is $OR_C$, where $R_C$ is lower alkyl.

In certain other embodiments, w is 0 or 1. In still other embodiments, one or more of $R_1$-$R_4$ is $OR_C$, where $R_C$ is lower alkyl.

VI) Compounds of the Formula (and Pharmaceutically Acceptable Derivatives Thereof):

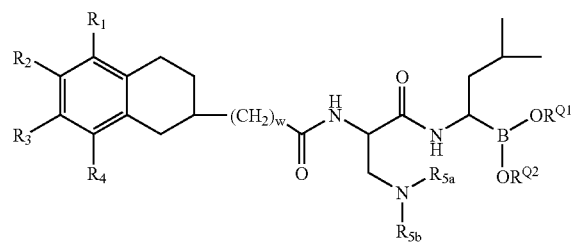

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety; $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2; and $R_1$, $R_2$, $R_3$ and $R_4$ are each independently hydrogen, $OR_C$, halogen, or $NR_CR_D$, wherein each occurrence of $R_C$ and $R_D$ is independently hydrogen or lower alkyl.

In certain embodiments, $R_{5a}$ and $R_{5b}$ are each independently hydrogen, —C(NH$_2$)=N(NO$_2$), —C(=O)OR$_{5}$C, —C(=O)R$_{5c}$, wherein $R_{5c}$ is alkyl, alkenyl, aryl or heteroaryl.

In certain embodiments, $R^{Q1}$ and $R^{Q2}$ are each independently hydrogen, lower alkyl, or, taken together, form a 5- to 6-membered alicyclic moiety.

In certain embodiments, each of $R_1$, $R_2$, $R_3$ and $R_4$ is a substituent other than hydrogen.

In certain other embodiments, one of $R_1$, $R_2$, $R_3$ or $R_4$ is hydrogen, and each of the other groups is substituted with a substituent other than hydrogen.

In still other embodiments, two of $R_1$, $R_2$, $R_3$, or $R_4$ are hydrogen, and the other two are substituted with a substituent other than hydrogen.

In yet other embodiments, three of $R_1$, $R_2$, $R_3$ or $R_4$ are hydrogen, and the remaining group is substituted with a substituent other than hydrogen.

In still other embodiments, the compound has the structure:

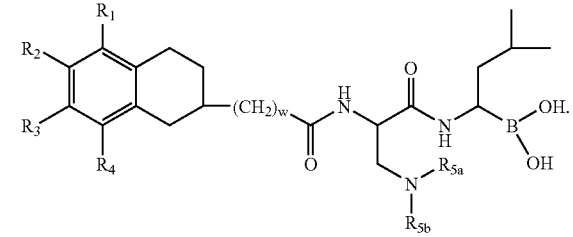

In yet other embodiments, the compound has the structure:

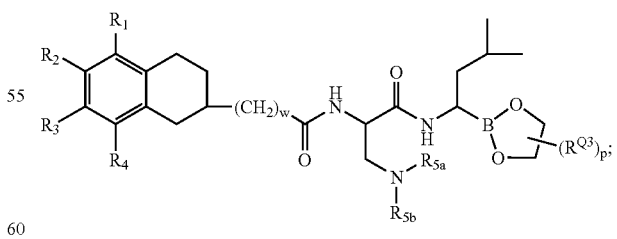

wherein $R^{Q3}$ is lower alkyl and p is an integer from 0-4.

In certain other embodiments, $R^{Q3}$ is methyl and p is 4.

In certain other embodiments, w is 0 or 1. In still other embodiments, one or more of $R_1$-$R_4$ is $OR_C$, where $R_C$ is lower alkyl.

VII) Compounds of the Formula (and Pharmaceutically Acceptable Derivatives Thereof):

wherein w is 0, 1 or 2, each occurrence of $R_C$ is independently lower alkyl, and q is 0, 1, 2, 3 or 4.

In certain embodiments, w is 0 or 1.

In certain other embodiments, q is 1. In still other embodiments, q is 2. In yet other embodiments, q is 3. In still other embodiments, q is 3.

In yet other embodiments, each occurrence of $R_C$ is methyl.

VIII) Compounds of the Formula (and Pharmaceutically Acceptable Derivatives Thereof):

wherein AR is an aryl or heteroaryl moiety; w is 0, 1 or 2, each occurrence of $R_C$ is dependently lower alkyl, and q is 0, 1, 2, 3 or 4.

In certain embodiments, AR is substitued or unsubstituted phenyl.

In certain embodiments, w is 0 or 1.

In certain other embodiments, q is 1. In still other embodiments, q is 2. In yet other embodiments, q is 3. In still other embodiments, q is 3.

In yet other embodiments, each occurrence of $R_C$ is methyl.

IX) Compounds of the Formula (and Pharmaceutically Acceptable Derivatives Thereof):

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety; w is 0, 1 or 2, each occurrence of $R_C$ is independently lower alkyl, and q is 0, 1, 2, 3 or 4.

In certain embodiments, $R_{5a}$ and $R_{5b}$ are each independently hydrogen, —C(NH$_2$)=N(NO$_2$), —C(=O)OR$_{5c}$, —C(=O)R$_{5c}$, wherein $R_{5c}$ is alkyl, alkenyl, aryl or heteroaryl.

In certain embodiments, w is 0 or 1.

In certain other embodiments, q is 1. In still other embodiments, q is 2. In yet other embodiments, q is 3. In still other embodiments, q is 3.

In yet other embodiments, each occurrence of $R_C$ is methyl.

X) Compounds of the Formula (and Pharmaceutically Acceptable Derivatives Thereof):

wherein $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2, each occurrence of $R_C$ is independently lower alkyl, and q is 0, 1, 2, 3 or 4.

In certain embodiments, $R^{Q1}$ and $R^{Q2}$ are each independently hydrogen, lower alkyl, or, taken together, form a 5- to 6-membered alicyclic moiety.

In still other embodiments, the compound has the structure:

In yet other embodiments, the compound has the structure:

herein $R^{Q3}$ is lower alkyl and p is an integer from 0-4.

In certain other embodiments, $R^{Q3}$ is methyl and p is 4.

In certain embodiments, w is 0 or 1.

In certain other embodiments, q is 1. In still other embodiments, q is 2. In yet other embodiments, q is 3. In still other embodiments, q is 3.

In yet other embodiments, each occurrence of $R_C$ is methyl.

XI) Compounds of the Formula (and Pharmaceutically Acceptable Derivatives Thereof):

wherein AR is an aryl or heteroaryl moiety; $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2, each occurrence of $R_C$ is independently lower alkyl, and q is 0, 1, 2, 3 or 4.

In certain embodiments, AR is substitued or unsubstituted phenyl.

In certain embodiments, $R^{Q1}$ and $R^{Q2}$ are each independently hydrogen, lower alkyl, or, taken together, form a 5- to 6-membered alicyclic moiety.

In still other embodiments, the compound has the structure:

In yet other embodiments, the compound has the structure:

wherein $R^{Q3}$ is lower alkyl and p is an integer from 0-4.

In certain other embodiments, $R^{Q3}$ is methyl and p is 4.

In certain embodiments, w is 0 or 1.

In certain other embodiments, q is 1. In still other embodiments, q is 2. In yet other embodiments, q is 3. In still other embodiments, q is 3.

In yet other embodiments, each occurrence of $R_C$ is methyl.

XII) Compounds of the Formula (and Pharmaceutically Acceptable Derivatives Thereof):

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety; $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2, each occurrence of $R_C$ is independently lower alkyl, and q is 0, 1, 2, 3 or 4.

In certain embodiments, $R_{5a}$ and $R_{5b}$ are each independently hydrogen, $-C(NH_2)=N(NO_2)$, $-C(=O)OR_{5c}$, $-C(=O)R_{5c}$, wherein $R_{5c}$ is alkyl, alkenyl, aryl or heteroaryl.

In certain embodiments, $R^{Q1}$ and $R^{Q2}$ are each independently hydrogen, lower alkyl, or, taken together, form a 5- to 6-membered alicyclic moiety.

In still other embodiments, the compound has the structure:

In yet other embodiments, the compound has the structure:

wherein $R^{Q3}$ is lower alkyl and p is an integer from 0-4.

In certain other embodiments, $R^{Q3}$ is methyl and p is 4.

In certain embodiments, w is 0 or 1.

In certain other embodiments, q is 1. In still other embodiments, q is 2. In yet other embodiments, q is 3. In still other embodiments, q is 3. In yet other embodiments, each occurrence of $R_C$ is methyl.

XIII) Compounds of the Formula (and Pharmaceutically Acceptable Derivatives Thereof):

wherein w is 0, 1 or 2; and q is 0, 1, 2, 3 or 4.

In certain embodiments, q is 1. In certain other embodiments, q is 2. In still other embodiments, q is 3. In yet other embodiments q is 4.

XIV) Compounds of the Formula (and Pharmaceutically Acceptable Derivatives Thereof):

wherein AR is an aryl or heteroaryl moiety; w is 0, 1 or 2; and q is 0, 1, 2, 3 or 4.

In certain embodiments, AR is substitued or unsubstitututed phenyl.

In certain embodiments, q is 1. In certain other embodiments, q is 2. In still other embodiments, q is 3. In yet other embodiments q is 4.

XV) Compounds of the Formula (and Pharmaceutically Acceptable Derivatives Thereof):

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety; w is 0, 1 or 2; and q is 0, 1, 2, 3 or 4.

In certain embodiments, $R_{5a}$ and $R_{5b}$ are each independently hydrogen, $-C(NH_2)=N(NO_2)$, $-C(=O)OR_{5c}$, $-C(=O)R_{5c}$, wherein $R_{5c}$ is alkyl, alkenyl, aryl or heteroaryl.

In certain embodiments, q is 1. In certain other embodiments, q is 2. In still other embodiments, q is 3. In yet other embodiments q is 4.

XVI) Compounds of the Formula (and Pharmaceutically Acceptable Derivatives Thereof):

wherein $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2; and q is 0, 1, 2, 3 or 4.

In certain embodiments, $R^{Q1}$ and $R^{Q2}$ are each independently hydrogen, lower alkyl, or, taken together, form a 5- to 6-membered alicyclic moiety.

In still other embodiments, the compound has the structure:

In yet other embodiments, the compound has the structure:

wherein $R^{Q3}$ is lower alkyl and p is an integer from 0-4.

In certain other embodiments, $R^{Q3}$ is methyl and p is 4.

In certain embodiments, q is 1. In certain other embodiments, q is 2. In still other embodiments, q is 3. In yet other embodiments q is 4.

XIV) Compounds of the Formula (and Pharmaceutically Acceptable Derivatives Thereof):

wherein AR is an aryl or heteroaryl moiety; $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2; and q is 0, 1, 2, 3 or 4.

In certain embodiments, AR is substitued or unsubstitututed phenyl.

In certain embodiments, $R^{Q1}$ and $R^{Q2}$ are each independently hydrogen, lower alkyl, or, taken together, form a 5- to 6-membered alicyclic moiety.

In still other embodiments, the compound has the structure:

In yet other embodiments, the compound has the structure:

wherein $R^{Q3}$ is lower alkyl and p is an integer from 0-4.

In certain other embodiments, $R^{Q3}$ is methyl and p is 4.

In certain embodiments, q is 1. In certain other embodiments, q is 2. In still other embodiments, q is 3. In yet other embodiments q is 4.

XV) Compounds of the Formula (and Pharmaceutically Acceptable Derivatives Thereof):

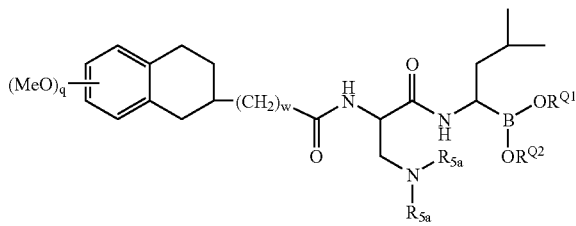

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety; $R^{Q1}$ and $R^{Q2}$ are each independently hydrogen, an aliphatic, alicyclic, heteroaliphatic, heteroalicyclic, aryl or heteroaryl moiety, or an oxygen protecting group, or $R^{Q1}$ and $R^{Q2}$, taken together, form a heteroalicyclic moiety; w is 0, 1 or 2; and q is 0, 1, 2, 3 or 4.

In certain embodiments, $R_{5a}$ and $R_{5b}$ are each independently hydrogen, —C(NH$_2$)=N(NO$_2$), —C(=O)OR$_{5c}$, —C(=O)R$_{5c}$, wherein $R_{5c}$ is alkyl, alkenyl, aryl or heteroaryl.

In certain embodiments, $R^{Q1}$ and $R^{Q2}$ are each independently hydrogen, lower alkyl, or, taken together, form a 5- to 6-membered alicyclic moiety.

In still other embodiments, the compound has the structure:

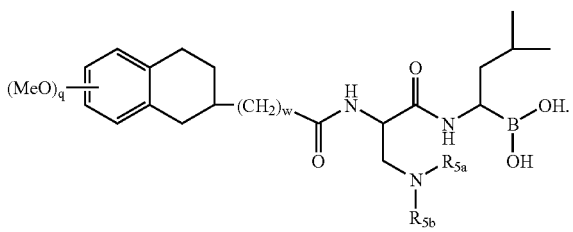

In yet other embodiments, the compound has the structure:

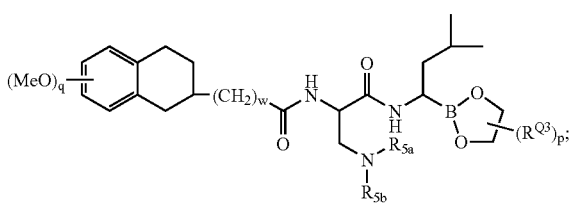

wherein $R^{Q3}$ is lower alkyl and p is an integer from 0-4.

In certain other embodiments, $R^{Q3}$ is methyl and p is 4.

In certain embodiments, q is 1. In certain other embodiments, q is 2. In still other embodiments, q is 3. In yet other embodiments q is 4.

It will also be appreciated that for each of the subgroups I-XV described above, a variety of other subclasses are of special interest, including, but not limited to those classes described above i)-xxxi) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Compounds and Definitions

As discussed above, this invention provides novel compounds with a range of biological properties. Compounds of this invention have biological activities relevant for the treatment of cancer and/or inflammatory disorders, and/or disorders caused by activation of certain regulatory subunits of the proteasome.

Compounds of this invention include those specifically set forth above and described herein, and are illustrated in part by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the prodrugs, are known and may be adapted to the present invention. Certain exemplary pharmaceutical compositions and pharmaceutically acceptable derivatives will be discussed in more detail herein below.

Numerous suitable prodrug moieties, and information concerning their selection, synthesis and use are well known in the art. Examples of prodrug moieties of interest include, among others, prodrug moieties that can be attached to primary or secondary amine-containing functionalities. Examples of such prodrug moieties include the following:

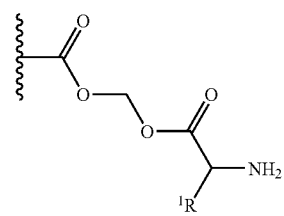

For the synthesis of the prodrug groups, see Borchardt, R. T. et. al., *J. Org. Chem.* 1997, 43, 3641-3652.

$R^1$ = all natural, unnatural amino acids

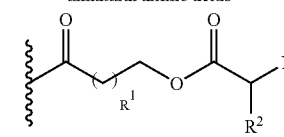

For the synthesis of the prodrug groups, see Zhou, X—X. et. al., PCT WO 99/51613.

$R^1$ = C1-C4 alkyl, cycloalkyl, oxyalkyl, aminoalkyl, etc.
$R^2$ = all natural, unnatural amino acids

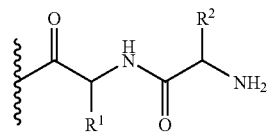

For the synthesis of the prodrug groups, see Ezra, A. et. al., *J. Med. Chem.* 2000, 43, 3641-3652.

$R^1$, $R^2$ = all natural, unnatural amino acids

Other examples of prodrug moieties of interest include prodrug moieties that can be attached to hydroxyl-containing functionalities. Such prodrug moieties a well-known in the art, and will be readily identified by a person skilled in the relevant art. The present invention encompasses any prodrug form of the compounds described herein.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of inflammatory disorders, cancer, and other disorders, as described generally above. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (ie., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "dialkylamino" refers to a group having the structure —N(R')$_2$, wherein R' is alkyl, as defined herein. The term "aminoalkyl" refers to a group having the structure NH$_2$R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of sutstituents of the above-described aliphatic (and other) moieties of compounds of the invention include, but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl" are interchangeable. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted with substituents including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have have substituted with an heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more of the hydrogen atoms thereon with but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples which are described herein.

3) Research Uses, Formulation and Administration

According to the present invention, the inventive compounds may be assayed in any of the available assays known in the art for identifying compounds having a pre-determined biological activity. For example, the assay may be cellular or non-cellular, in vivo or in vitro, high- or low-throughput format, etc. In certain exemplary embodiments, the inventive compounds are tested in assays to identify those compounds having proteasome inhibitory activity, antiproliferative/anticancer activity and/or anti-inflammatory effect.

Thus, in one aspect, compounds of this invention which are of particular interest include those which:

exhibit activity generally as proteasome inhibitors;
exhibit an antiproliferative and/or anticancer effect on suitable cell lines maintained in vitro, or in animal studies using a scientifically acceptable model;
exhibit an anti-inflammatory effect on suitable cell lines maintained in vitro, or in animal studies using a scientifically acceptable model;
exhibit in vivo efficacy vs. human cancer xenografts; and
exhibit a favorable therapeutic profile (e.g., safety, efficacy, and stability).

As detailed in the exemplification herein in assays to determine the ability of exemplary compounds to effect growth inhibition, certain of the compounds exhibit $IC_{50}s$ (growth inhibition vs. adherent HT-29, OVCAR-3, or MDA-MB-435) less than 1 µM. In certain other embodiments, compounds exhibit $IC_{50}s$ (growth inhibition vs. adherent HT-29, OVCAR-3, or MDA-MB-435) less than 100 nM. In still other embodiments, compounds exhibit $IC_{50}s$ (growth inhibition vs. adherent HT-29, OVCAR-3, or MDA-MB-435) less than 10 nM. As also described in the exemplification herein, inventive compounds are also useful as proteasome inhibitors. In certain embodiments, compounds exhibit $IC_{50}s$ (human leukocyte lysates, HT-29 colon carcinoma, and 20S proteasomes) less than 1 µM. In certain other embodiments, compounds exhibit $IC_{50}s$ (human leukocyte lysates, HT-29 colon carcinoma, and 20S proteasomes) less then 100 nM. In still other embodiments, compounds exhibit $IC_{50}s$ (human leukocyte lysates, HT-29 colon carcinoma, and 20S proteasomes) less than 10 nM.

In yet other embodiments, for compounds as described generally above where A-B-D-E together represent $CH_2$—$CH_2$—$CH_2$—$CH_2$, w is 0, and $R_1$, $R_2$, $R_3$ and $R_4$ are each independently hydrogen, $OR_C$, halogen, or $NR_CR_D$, wherein each occurrence of $R_C$ and $R_D$ is independently hydrogen or lower alkyl, or wherein $R_C$ and $R_D$ taken together, or two occurrences of $R_C$ or $R_D$, taken together are a cycloalipahtic, or heterocycloaliphatic moiety, $IC_{50}s$ (20S inhibition) in the range of 0.50 to 5.0 nM are observed and $IC_{50}s$ (growth inhibition) in the range of 1.0 to 11.0 nM are observed.

As discussed above, certain of the compounds as described herein exhibit activity generally as proteasome inhibitors. More specifically, compounds of the invention demonstrate anti-inflammatory and/or antitumor activity and thus the invention further provides a method for treating an inflammatory disorder or a proliferative disorder, such as cancer. In certain other embodiments, the compounds of the invention are useful for treating cancer, where the cancer is a solid tumor.

The method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, prostate cancer, breast cancer, lung cancer, colon cancer, lymphoma, bladder cancer, cervical cancer, uterine cancer, melanoma and/or skin cancer, kidney cancer, testicular cancer, ovarian cancer, stomach cancer, leukemia, brain cancer, multiple myeloma, liver cancer, pancreatic cancer or esophageal cancer). In other embodiments, the inventive compounds are useful for the treatment of inflammatory disorders, and/or disorders caused by activation of certain regulatory subunits of the proteasome (e.g., diseases caused by the activation of the NFκB pathway, or certain genetic diseases involving the misfolding of proteins, to name a few). These disorders include, but are not limited to inflammation, autoimmune diseases (e.g., rheumatoid arthritis, lupus erythematosus, multiple sclerosis), respiratory distress syndrome, neurological disease (e.g., Alzheimer's Disease), ischemia, cachexia, cystic fibrosis, neoplasm, and HIV infection.

Pharmaceutical Compositions

As discussed above this invention provides novel compounds that have biological properties useful for the treatment of cancer and/or inflammatory disorders, and, in certain embodiments, more generally are useful as proteaseome inhibitors. In certain embodiments, the inventive compounds as useful for the treatment of cancer (including, but not limited to, prostate cancer, breast cancer, lung cancer, colon cancer, lymphoma, bladder cancer, cervical cancer, uterine cancer, melanoma and/or skin cancer, kidney cancer, testicular cancer, ovarian cancer, stomach cancer, leukemia, brain cancer, multiple myeloma, liver cancer, pancreatic cancer or esophageal cancer). In other embodiments, the inventive compounds are useful for the treatment of inflammatory disorders, and/or disorders caused by activation of the regulatory subunits of the proteasome. These disorders include, but are not limited to inflammation, autoimmune diseases (e.g., rheumatoid arthritis, lupus erythematosus, multiple sclerosis), respiratory distress syndrome, neurological disease (e.g., Alzheimer's Disease), ischemia, cachexia, cystic fibrosis, neoplasm, and HIV infection.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an anti-inflammatory agent (e.g., an agent for the treatment of rheumatoid arthritis or psoriasis) or cytotoxic agent or anticancer agent approved for the treatment of cancer, as discussed in more detail herein, or it may be any one of a number of agents undergoing approval in the Food and Drug Administration that ultimately obtain approval for the treatment of cancer or an inflammatory disorder. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses and Formulations of Compounds of the Invention

As described in more detail herein, in general, the present invention provides compounds useful for the treatment of cancer and inflammatory disorders. Without wishing to be bound by any particular theory, more generally, the compounds of the invention have also been shown to act as proteaseome inhibitors and thus may be useful more generally for a variety of disorders that are affected by processes regulated by the proteasome (e.g., cell cycle, activation of NFκB, to name a few).

As discussed above, compounds of the invention exhibit antiproliferative and antitumor activity. As such, compounds of the invention are particularly useful for the treatment of cancer, and in certain embodiments for the treatment of solid tumors. Additionally, the inventive compounds are useful as proteasome inhibitors and can thus be used for the treatment of a variety of disorders, as discussed herein, that are affected by the proteasome.

Thus, as described above, in another aspect of the invention, a method for the treatment of cancer is provided comprising administering a therapeutically effective amount of a compound of formula (I), as described herein, to a subject in need thereof. It will be appreciated that the compounds and compositions, according to the method of the present invention, may be administered using any amount and any route of administration effective for the treatment of cancer. Thus, the expression "effective amount" as used herein, refers to a sufficient amount of agent to kill or inhibit the growth of tumor cells. In other embodiments, compounds may be useful for the treatment of inflammatory disorders, or other disorders affected by proteasome inhibition and thus "effective amount" refers to a sufficient amount of agent to treat or ameliorate the symptoms of the inflammatory disorder, or alternatively, refers to a sufficient amount to effect proteasome inhibition. The exact amount required will vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, as an aerosol, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, aerosols, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carrnustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference. It will also be appreciated that the therapies employed may achieve a desired effect for the same disorder (for example, an inventive compound may be administered concurrently with another anti-inflammatory agent or anti-cancer agent), or they may achieve different effects (e.g., control of any adverse effects).

In certain embodiments, the pharmaceutical compositions of the present invention further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The practitioner has a a well-established literature of peptide chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

1) Experimental Procedures:

As described above, the present invention provides novel epoxomicin and eponemycin analogs having formula (I) as described above and in certain classes and subclasses herein. The synthesis of certain exemplary compounds is described in detail below. It will be appreciated that the methods as described herein can be applied to each of the compounds as disclosed herein and equivalents thereof. Additionally, certain regents and starting materials are well known to those skilled in the art. Although the following examples describe certain exemplary compounds, it will be appreciated that the use of alternate starting materials will readily yield other analogues encompassed by the invention.

The Examples that follow describe exemplary synthetic methodologies for the preparation of inventive compounds wherein Q is an epoxycarbonyl moiety. In addition, the skilled practitioner has a well-established literature of boron and peptide chemistry to draw upon, in combination with the information contained in the many examples which follow, for guidance on synthetic strategies, protecting groups, and other materials and methods useful for the synthesis of those inventive compounds wherein Q is a boron-containing moiety. References of particular interest include U.S. Pat. No. 6,297,217 and references cited therein, each of which is incorporated herein by reference in its entirety. Thus, a person of ordinary skill in the art may draw upon the cited literature and the synthetic guidance provided herein (e.g., for P2 and P3 fragments) to prepare the inventive boron-containing compounds. The practitioner, armed with knowledge in the relevant art and the teaching and guidance provided herein and the cited references will know how to select available relevant chemical transformations, combined with protection and deptrotection schemes, as desired or required, to prepare compounds of the invention wherein Q is a boron-containing moiety.

In certain embodiments, as depicted generally below in Schemes 1-5, the three components of the compounds, P1, P2 and P3 can each be varied to generate a variety of analogues. In certain embodiments, P1 and P2 are constant, as depicted in Scheme 6, and P3 can be varied as desired as depicted generally below and in the exemplification herein.

Scheme 1: P1 Modification:
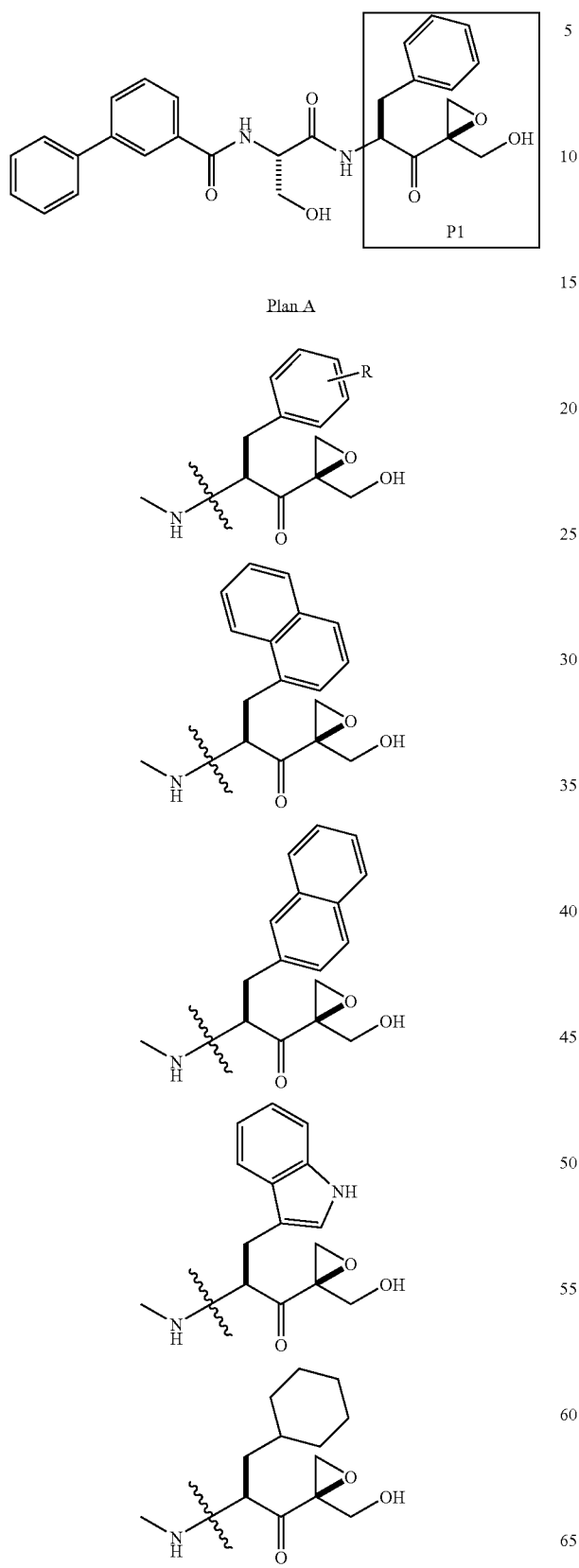
Plan A
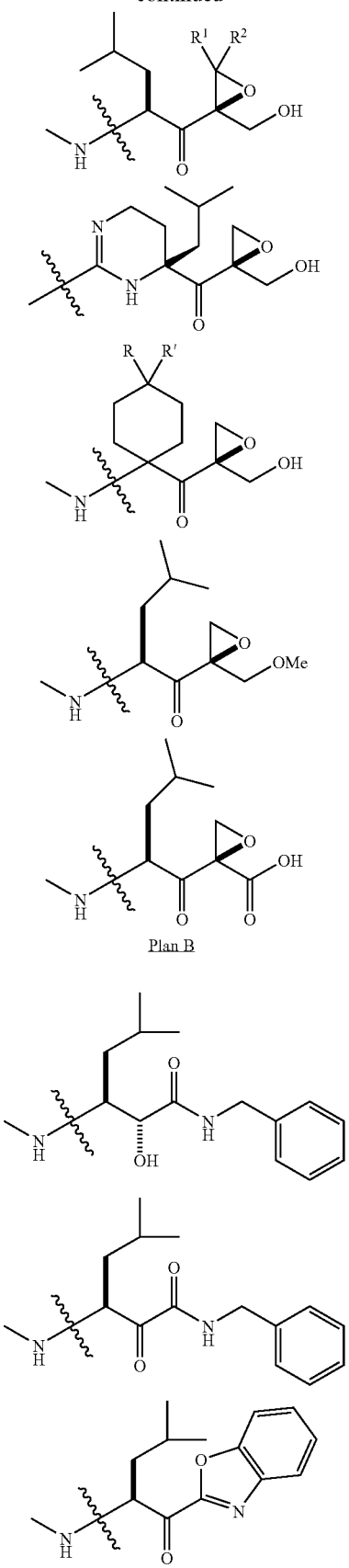
Plan B

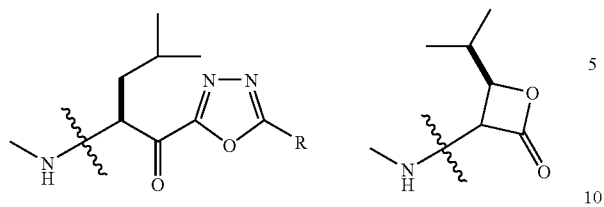
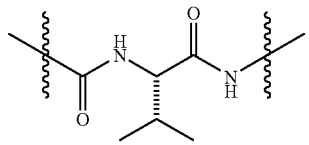
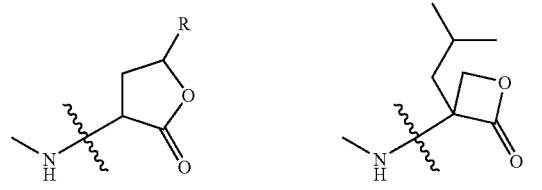
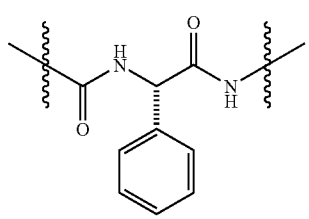
Scheme 2: P2 modifications:
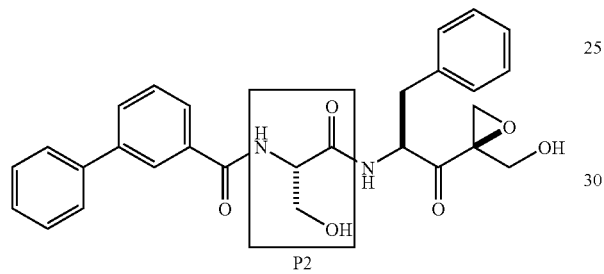
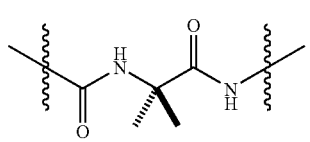
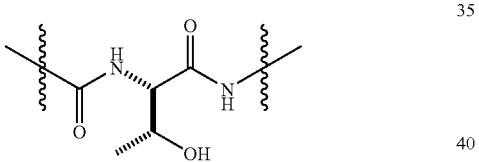
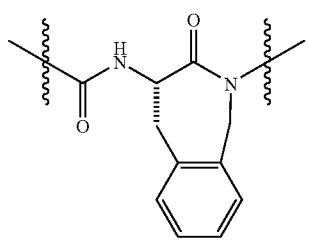
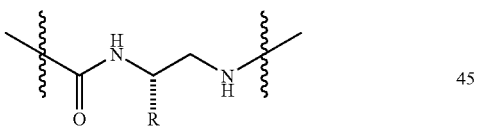
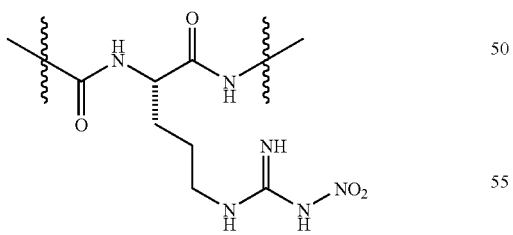
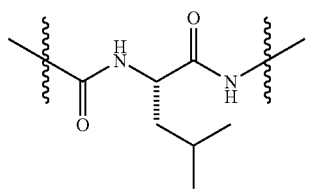
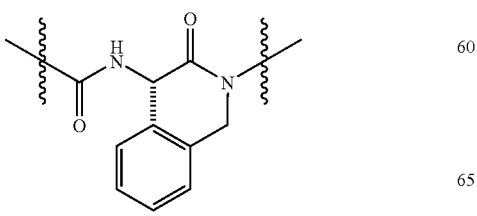
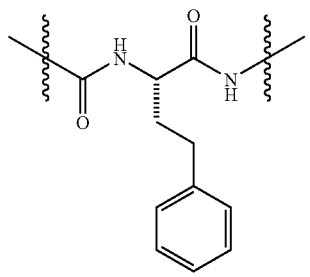

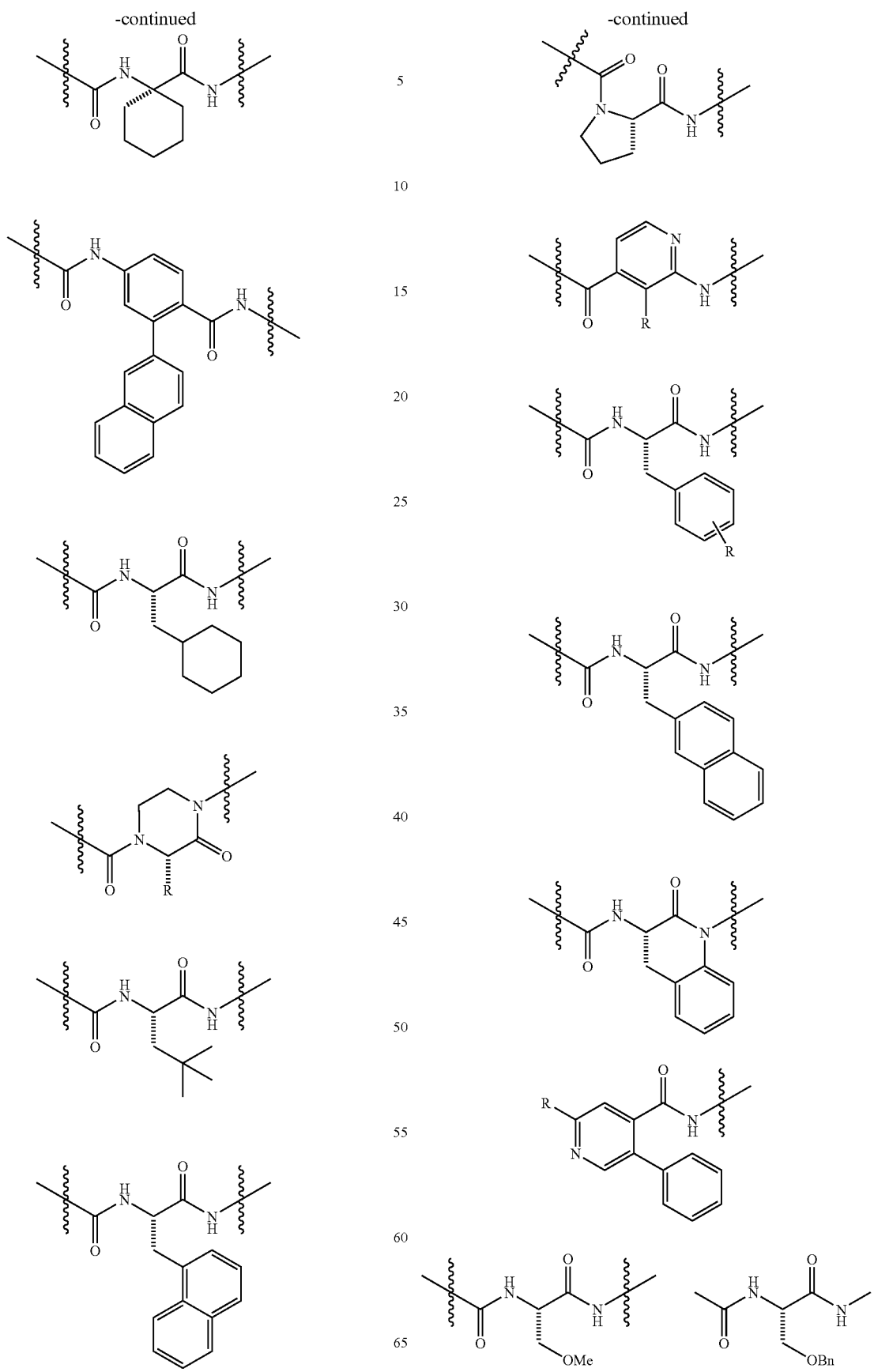

Scheme 3: P2 modifications (continued):
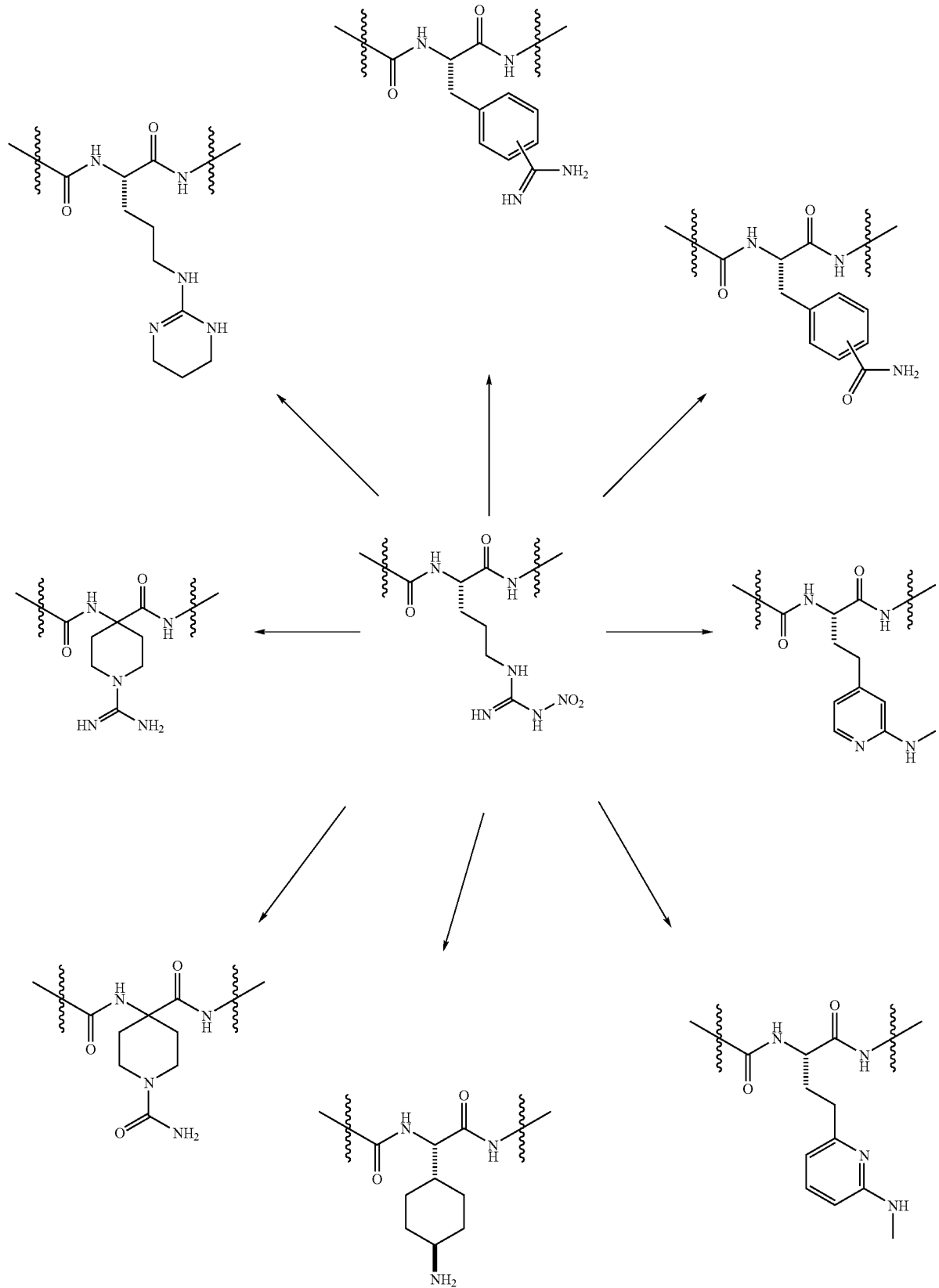

Scheme 4: P3 modifications:
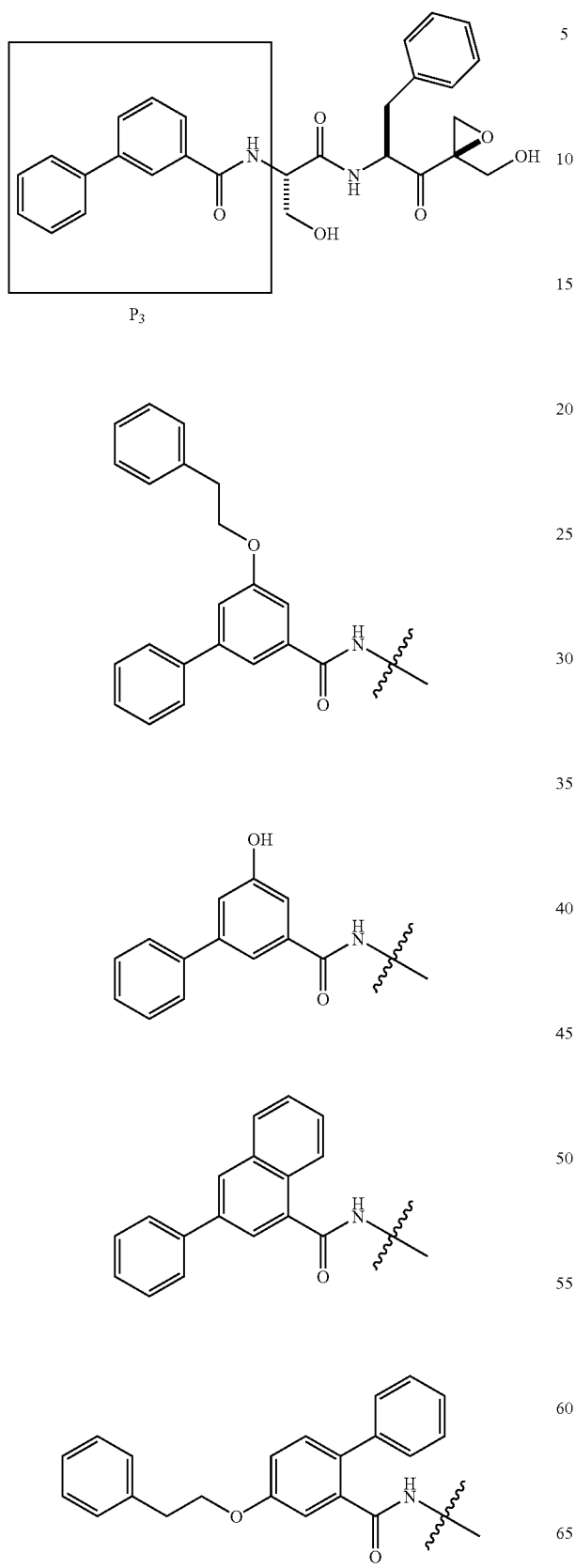
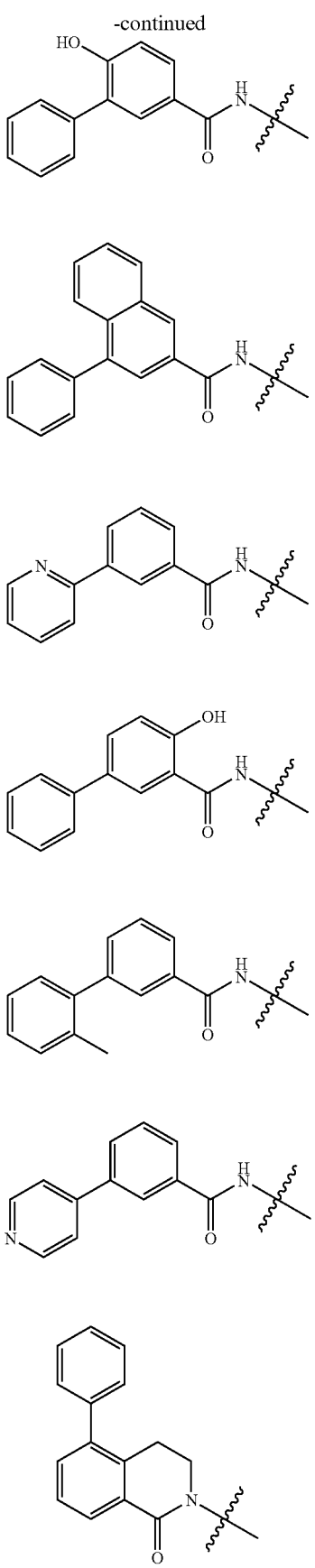

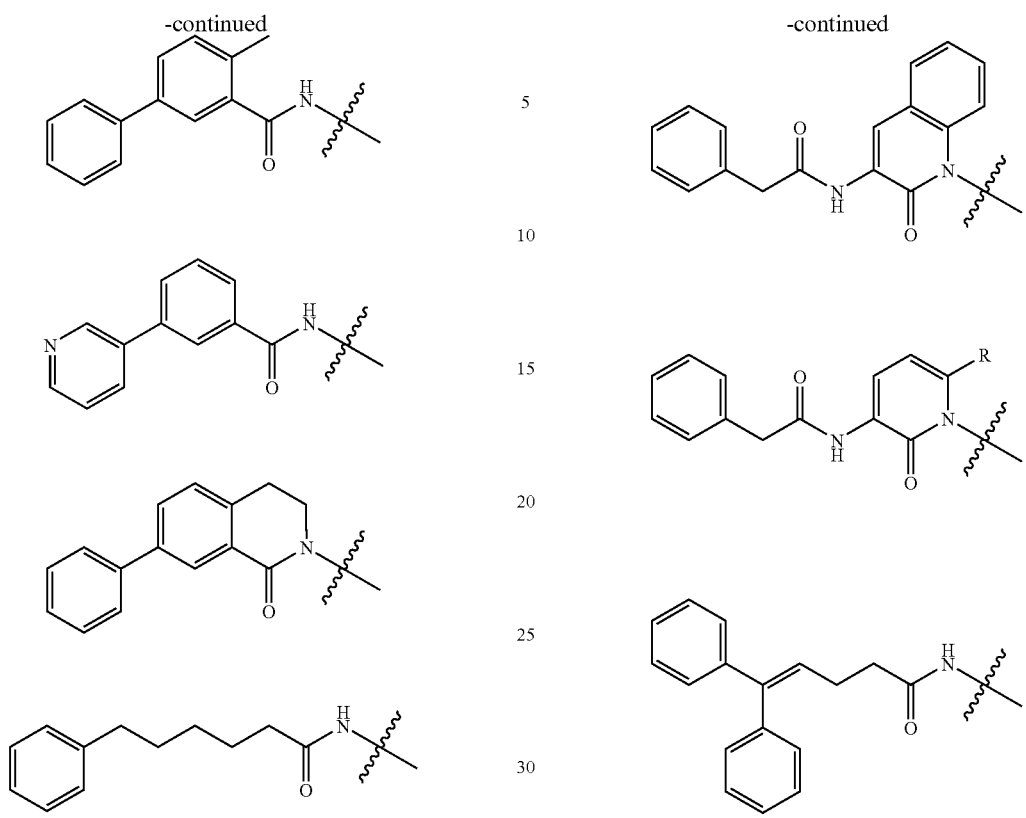
Scheme 5: P3 modification continued:
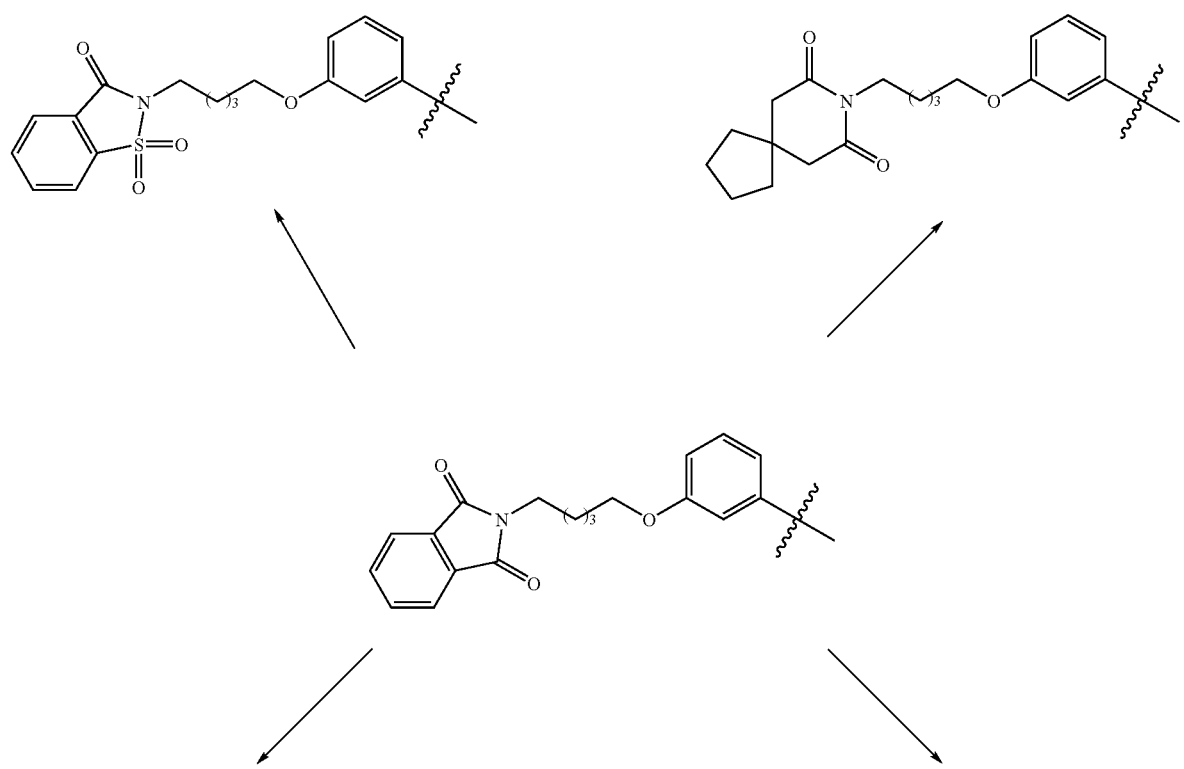

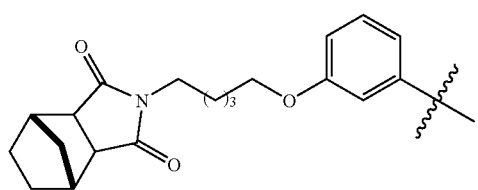
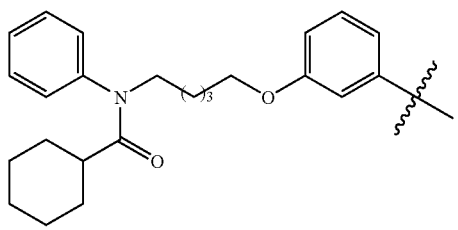
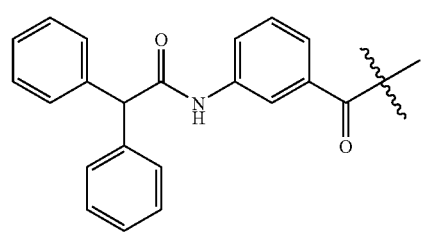
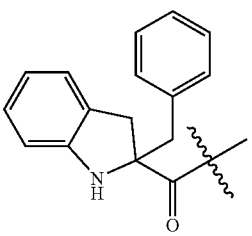
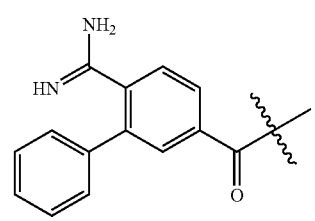
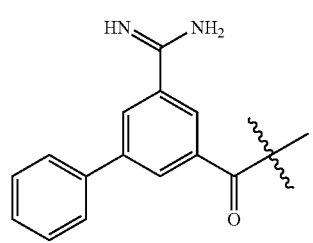
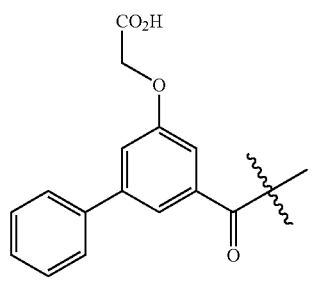
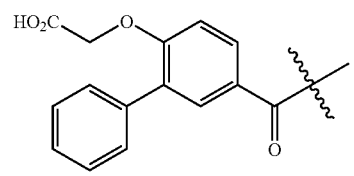
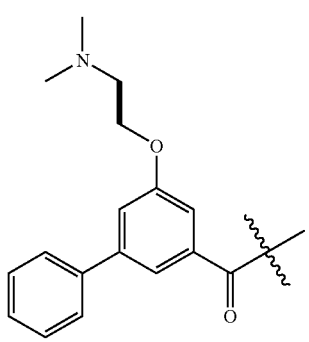
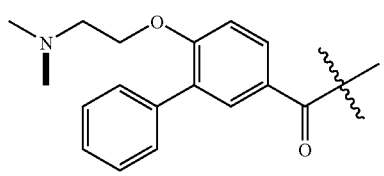
As discussed above, in certain embodiments of the invention, P1 and held constant while P3 is varied. One exemplary embodiment is depicted Certain other embodiments are described generally in the experimentals Scheme 6: Synthesis of certain exemplary compounds where P1 and P2 are each constant as depicted:
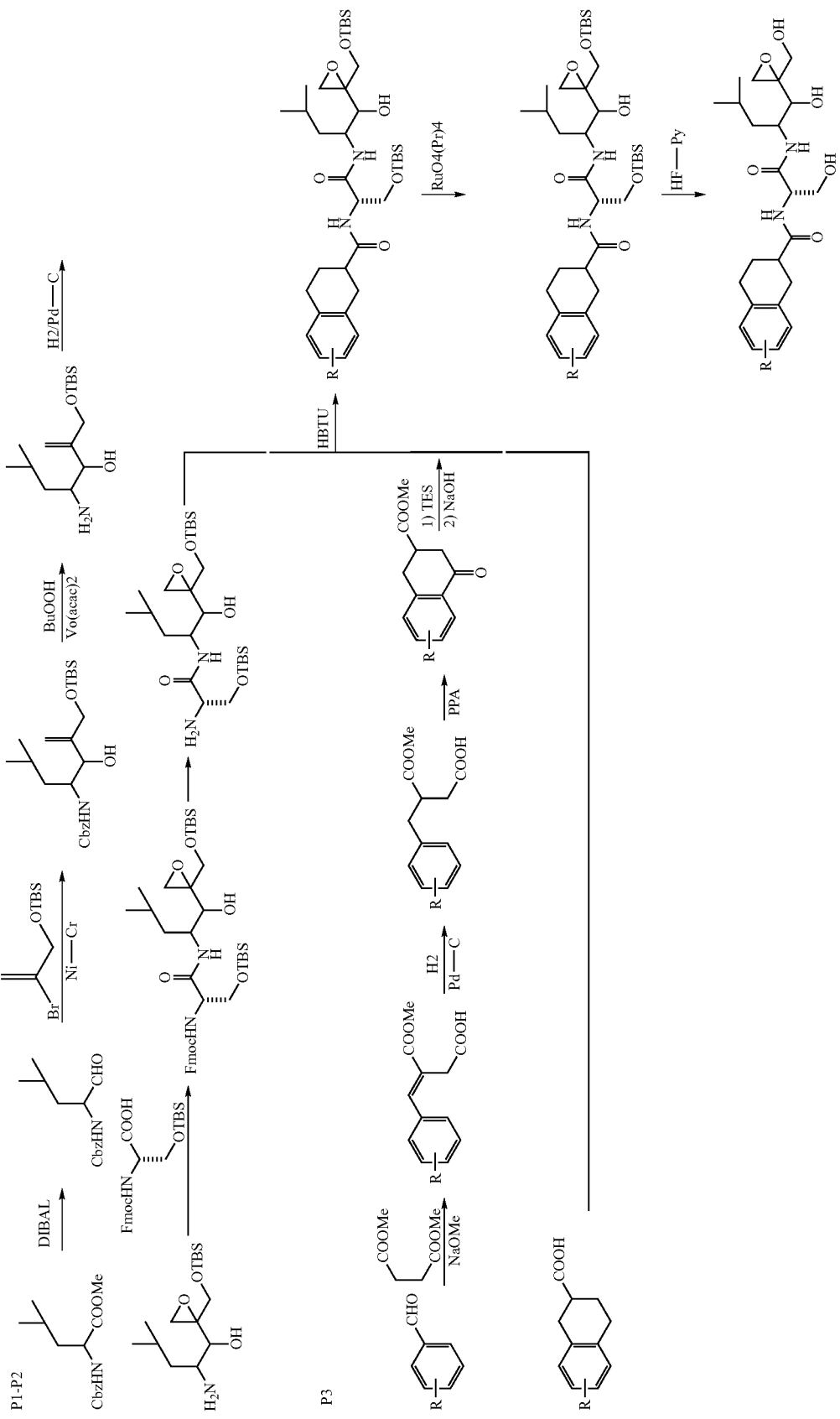

As depicted above in Scheme 6, in general, the components P1 and P2 are prepared and coupled to yield the epoxyalcohol. Scheme 6 also depicts one exemplary embodiment where P3 represents a bicyclic carboxylic acid which is then coupled via amide coupling to the P1-P2 component. Subsequent oxidation of the alcohol and deprotection yields the subclass of compounds depicted above. It will be appreciated, however, that a variety of P3 components can be utilized to generate inventive compounds, many of which are depicted herein. Furthermore, although the preparation of the P1-P2 component as an epoxyalcohol is depicted above, it will be appreciated that this component can also be prepared as the epoxyketone, as detailed in the exemplification herein.

A) General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, or by proton nuclear magnetic resonance, of a suitably worked up sample of the reaction mixture.

B) General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, then filtered. The crude products were then isolated by removal of solvent(s) by rotary evaporation under reduced pressure, at an appropriate temperature (generally less than 45° C.).

C) General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum beore submission for biological testing.

D) Experimentals for Certain Exemplary Compounds:

All commercial solvent was used without any purification. Flush column chromatography was performed on Merck silica gel 60 (230-400 mesh) using hexane-ethyl acetate solvent.

According to the general procedure below mentioned, and referring to the listing of compounds following these procedures, compounds A are synthesized with the modification of P3 part, compounds J are synthesized with the modification of P2, compounds C are synthesized with the modification of P1, and compounds D are synthesized with the modification of P1, P2 and P3.

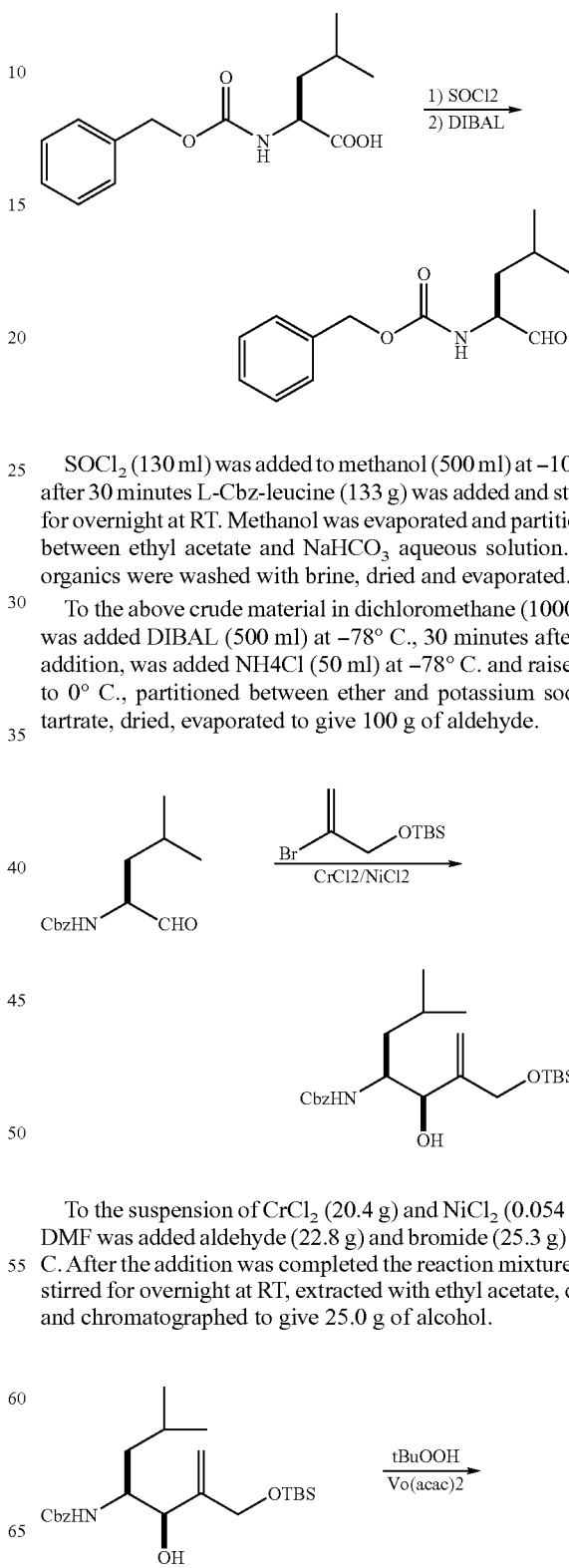

$SOCl_2$ (130 ml) was added to methanol (500 ml) at −10° C., after 30 minutes L-Cbz-leucine (133 g) was added and stirred for overnight at RT. Methanol was evaporated and partitioned between ethyl acetate and $NaHCO_3$ aqueous solution. The organics were washed with brine, dried and evaporated.

To the above crude material in dichloromethane (1000 ml) was added DIBAL (500 ml) at −78° C., 30 minutes after the addition, was added NH4Cl (50 ml) at −78° C. and raised up to 0° C., partitioned between ether and potassium sodium tartrate, dried, evaporated to give 100 g of aldehyde.

To the suspension of $CrCl_2$ (20.4 g) and $NiCl_2$ (0.054 g) in DMF was added aldehyde (22.8 g) and bromide (25.3 g) at 0° C. After the addition was completed the reaction mixture was stirred for overnight at RT, extracted with ethyl acetate, dried and chromatographed to give 25.0 g of alcohol.

-continued

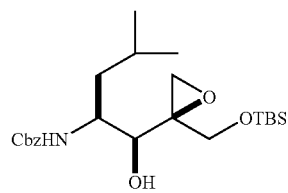

Allyl alcohol (16.5 g) was dissolved into 150 ml of toluene. VO(acac)$_2$ (0.42 g) was added followed by tBuOOH (15.6 ml of a 5-6M solution). The resulting solution was stirred for 3 hours at room temperature, extracted with ethyl acetate, dried and chromatographed to give 15.4 g of epoxide.

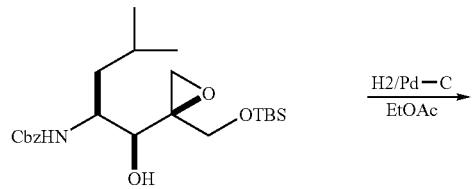

Epoxide (10 g) was dissolved in 100 ml of ethyl acetate, followed by the addition of catalytic 5% Pd—C, and the mixture was stirred for 4 hours at RT in hydrogen atmosphere.

The reaction mixture was then filtered through Celite and the organics concentrated to obtain 6.9 g of amine. The crude material was used without further purification.

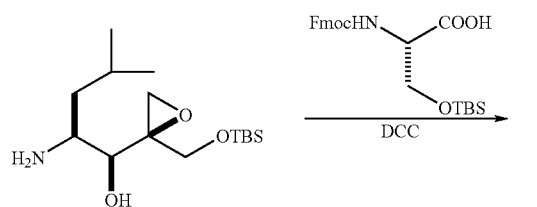

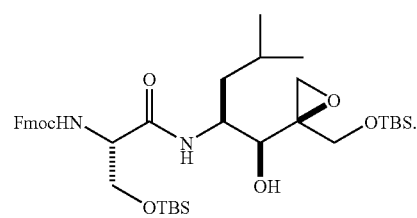

The solution of amine (16.43 g), carboxylic acid (25 g), DCC (22.8 g) and N-hydroxy-succinimide (12.6 g) in dichloromethane (400 ml) was stirred at −20° C. for overnight and the reaction mixture was loaded on chromatography to give 24.8 g of desired compound.

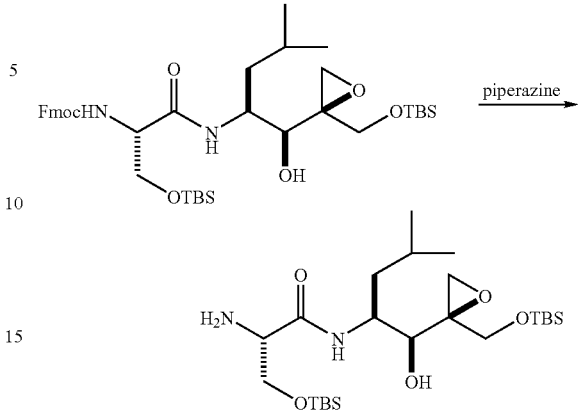

To the solution of starting material (24.7 g) in DMF (130 ml) was added piperazine (29 g) at 0° C. and stirred for 1 hour. The reaction mixture was partitioned between water and ethyl acetate, dried and chromatographed to give 16.7 g of desired amine.

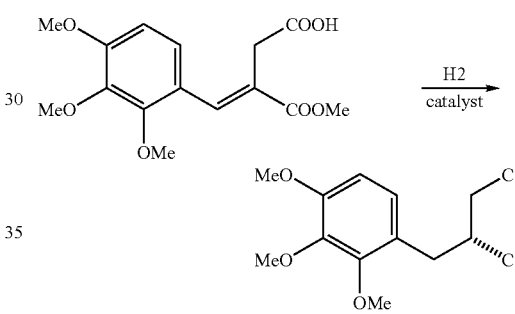

A solution of unsaturated ester (17.5 g) in 80 ml of methanol were added to the (R,R)-(−)-1,2-bis[(o-methoxyphenyl)(phenyl)phosphino]ethane(1,5-cyclooctadiene)rhodium(I) tetrafluoroborate (100 mg) and triethylamine (4.3 g). The reaction mixture was stirred at room temperature for 24 hours in the hydrogen atmosphere. After removing solvent, the residue was partitioned between 0.1 M NaOH and dichloromethane. The aqueous layer was acidified and extracted with ethyl acetate, dried to give 10 g of pure product.

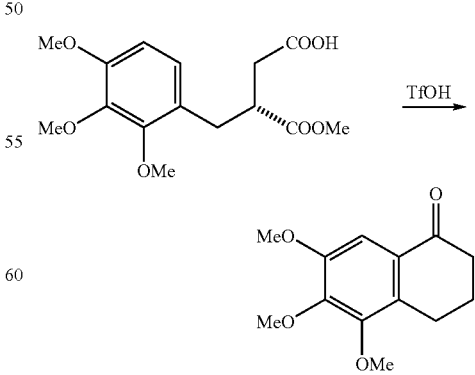

Starting acid (5 g) was dissolved in trifluoromethane sulfonic acid (20 ml) at 0° C., stirred for 2 hours, partitioned between ethyl acetate and sodium bicarbonate solution. Organic layer was dried to give 4.5 g of ketone.

for overnight at RT. Then the mixture was partitioned between ethyl acetate and water, the organics was dried and chromatographed to give 525 mg of desired amide.

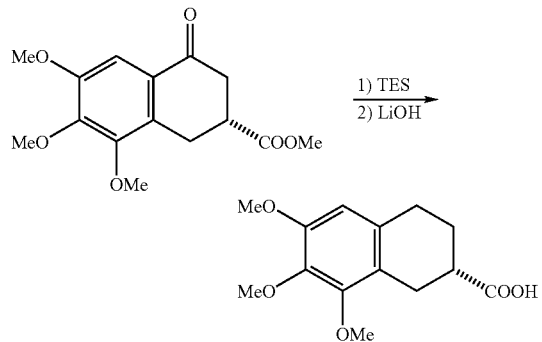

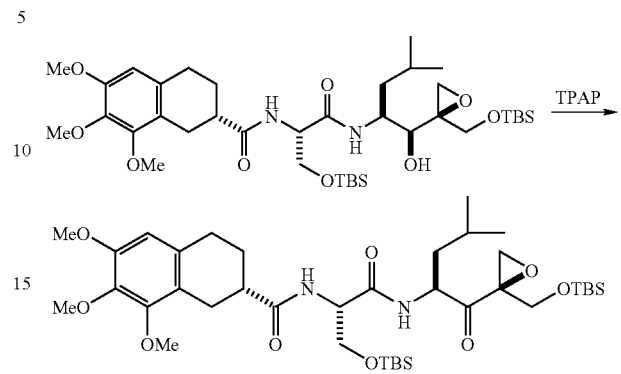

To the ketone (4.5 g) in trifluoro acetic acid (20 ml) was added triethyl silane (15 ml) at 0° C. After stirring for 4 hours at RT, the reaction mixture was partitioned between ethyl acetate and sodium bicarbonate solution, the organic layer was dried, evaporated to give 4 g of eater. This ester was To the solution of alcohol (525 mg) in dichloromethane (20 ml) was added tetrapropylammonium perruthenate (10 mg) and 4-methyl morpholine oxide (408 mg). After stirred for 5 hours at RT, the mixture was chromatographed to give ketone (500 mg).

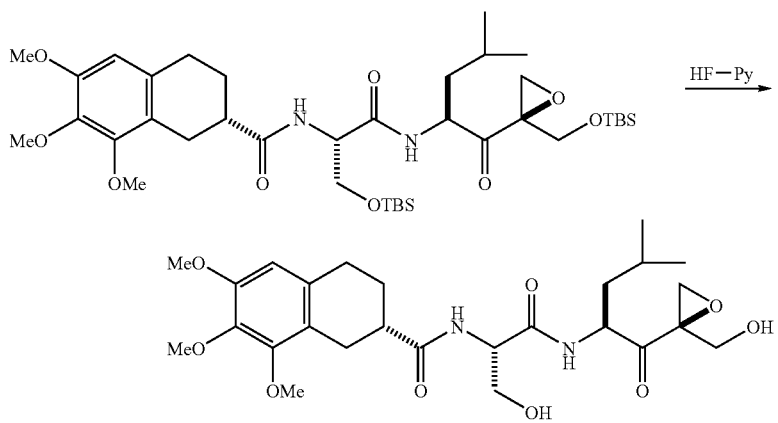

hydlyzed with lithium hydroxide in THF:MeOH:H2O (3:1:1) at RT for 2 hours to give 3.5 g of acid.

To the solution of ketone (500 mg) in THF (30 ml) was added hydrogen fluoride-pyridine (4 ml) at RT. After 2 hours, the mixture was partitioned between ethyl acetate and sodium bicarbonate solution, the organics was dried, chromatographed to give alcohol (312 mg).

E) Alternative Procedure to Prepare Oxidized P1-P2 Component:

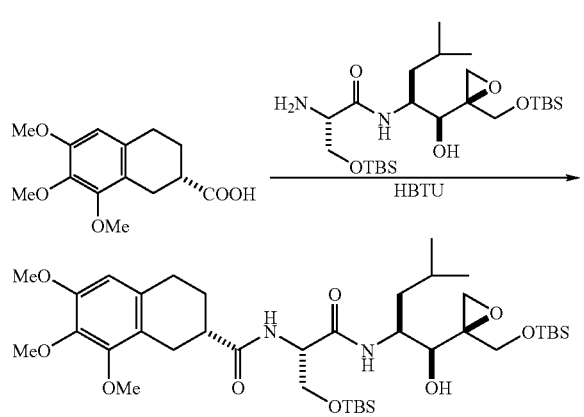

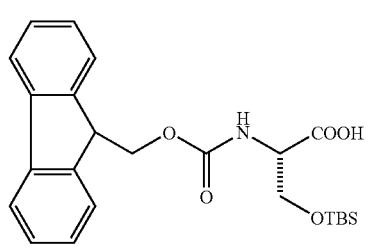

The solution of carboxylic acid (266 mg), amine (502 mg) and HBTU (760 mg) in dichloromethane (10 ml) was stirred (1)

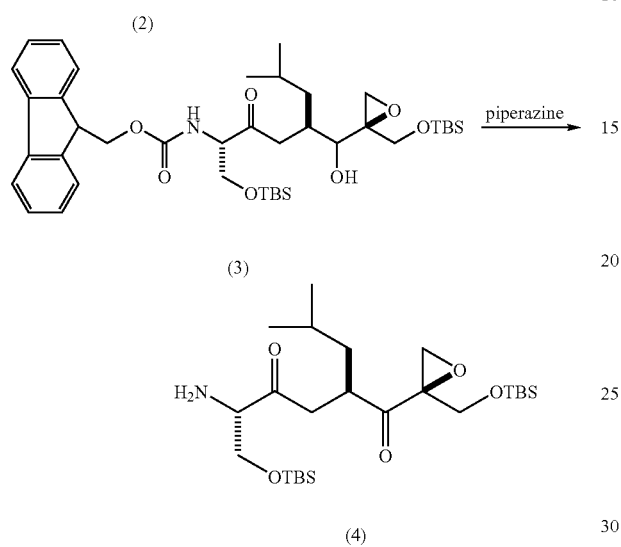

Synthesis of (3)

To the 25 g (0.0566 mol) of (1), 12.66 g (0.11 mol) of N-hydroxysuccinimide and 22.8 g (0.11 mol) of DCC were dissolved in 300 ml of dichloromethane at −78° C. After stirring for 1 hour 16.43 g (0.0541 mol) of (2) in 20 ml of dichloromethane was added and stirred at −20° C. for overnight. The reaction mixture was evaporated and the crude material was purified on silica gel chromatography to afford 24.8 g (63% yield) of (3) as pale yellow foam.

Synthesis of (4)

24.8 g (0.034 mol) of (3) was dissolved in 136 ml of anhydrous DMF at 0° C. To this solution was added 29 g (0.344 mol) of piperazine and stirred at 0° C. for 2 hours and then the reaction mixture was poured into ethylacetate. The organic layer was washed successively water and brine and dried over MgSO$_4$. The crude material laws purified on silica gel chromatography to afford 16.72 g (97%) of (4) as colorless oil.

F) Synthesis of ER-804191:

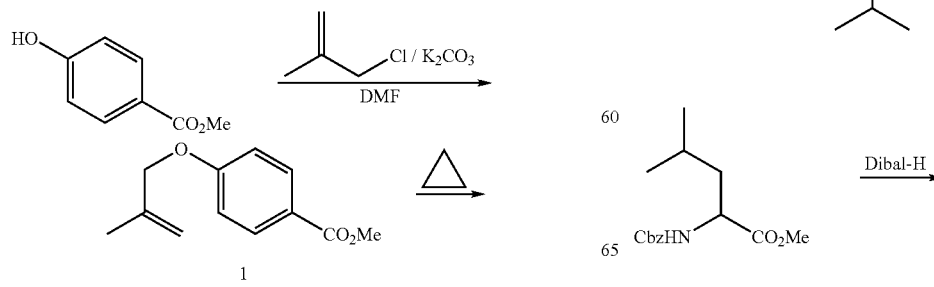

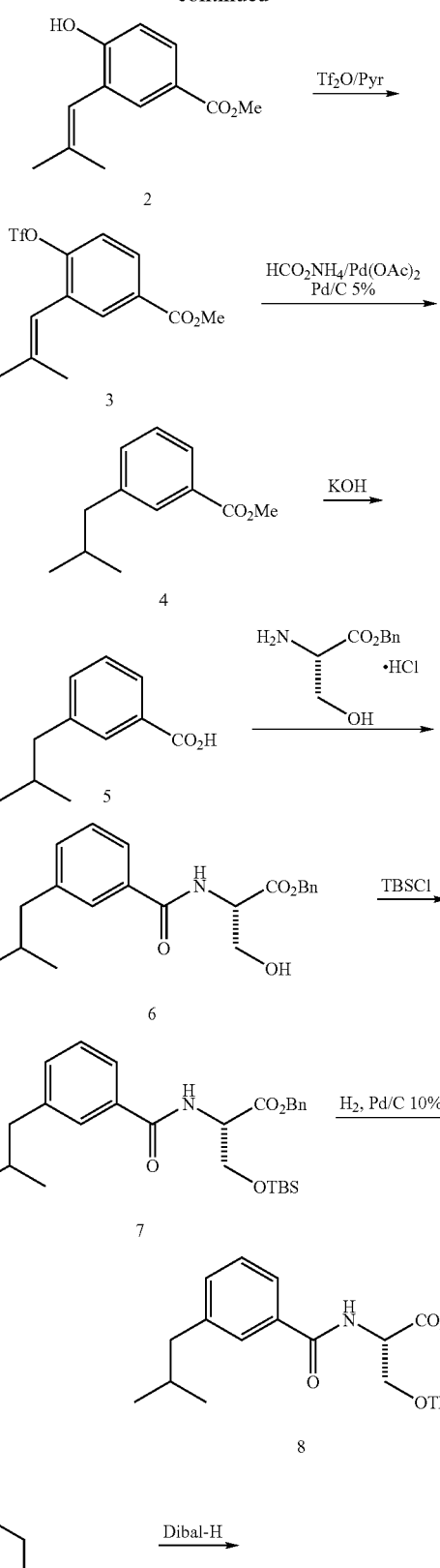

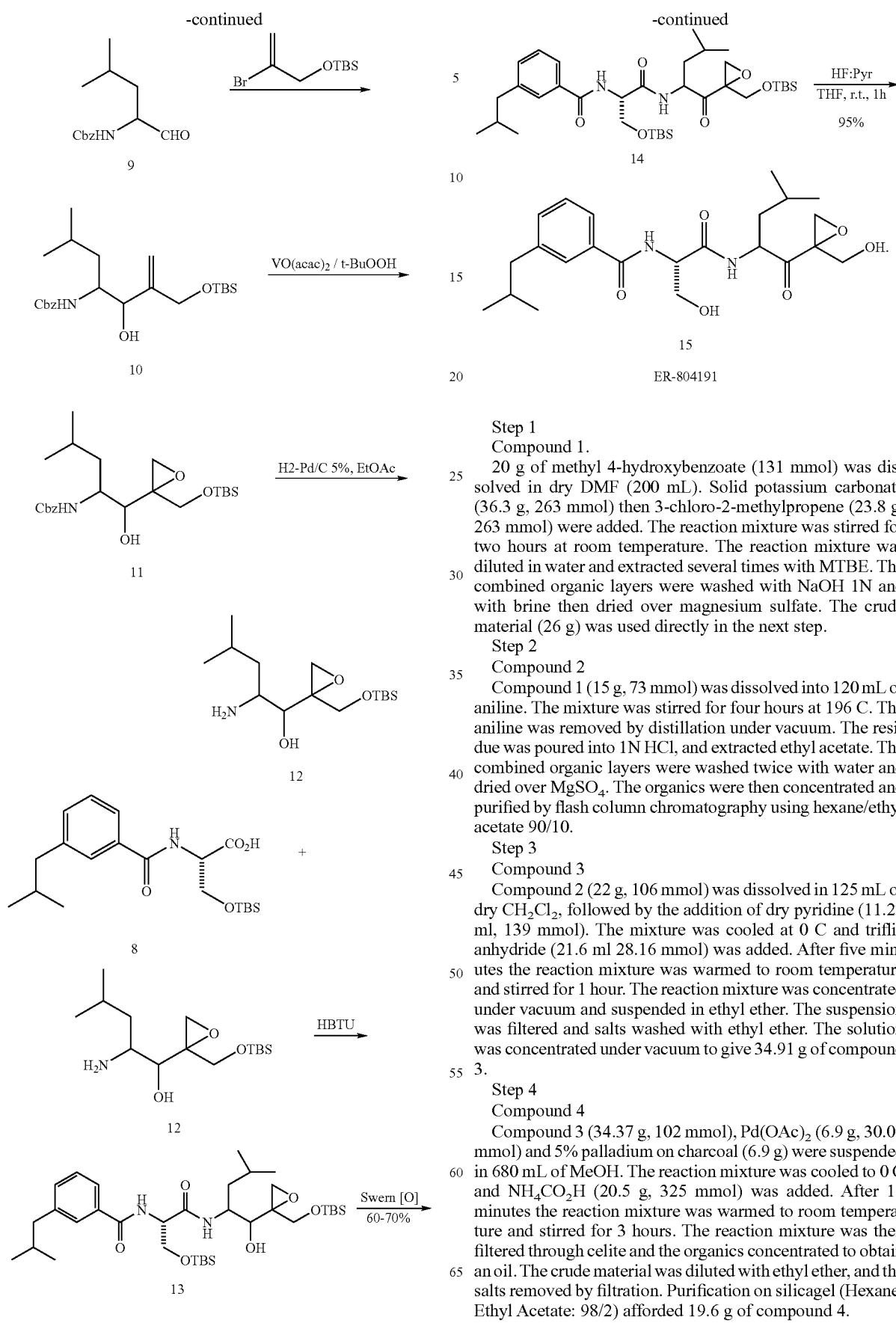

Step 1
Compound 1.
20 g of methyl 4-hydroxybenzoate (131 mmol) was dissolved in dry DMF (200 mL). Solid potassium carbonate (36.3 g, 263 mmol) then 3-chloro-2-methylpropene (23.8 g, 263 mmol) were added. The reaction mixture was stirred for two hours at room temperature. The reaction mixture was diluted in water and extracted several times with MTBE. The combined organic layers were washed with NaOH 1N and with brine then dried over magnesium sulfate. The crude material (26 g) was used directly in the next step.

Step 2
Compound 2
Compound 1 (15 g, 73 mmol) was dissolved into 120 mL of aniline. The mixture was stirred for four hours at 196 C. The aniline was removed by distillation under vacuum. The residue was poured into 1N HCl, and extracted ethyl acetate. The combined organic layers were washed twice with water and dried over MgSO$_4$. The organics were then concentrated and purified by flash column chromatography using hexane/ethyl acetate 90/10.

Step 3
Compound 3
Compound 2 (22 g, 106 mmol) was dissolved in 125 mL of dry CH$_2$Cl$_2$, followed by the addition of dry pyridine (11.23 ml, 139 mmol). The mixture was cooled at 0 C and triflic anhydride (21.6 ml 28.16 mmol) was added. After five minutes the reaction mixture was warmed to room temperature and stirred for 1 hour. The reaction mixture was concentrated under vacuum and suspended in ethyl ether. The suspension was filtered and salts washed with ethyl ether. The solution was concentrated under vacuum to give 34.91 g of compound 3.

Step 4
Compound 4
Compound 3 (34.37 g, 102 mmol), Pd(OAc)$_2$ (6.9 g, 30.06 mmol) and 5% palladium on charcoal (6.9 g) were suspended in 680 mL of MeOH. The reaction mixture was cooled to 0 C and NH$_4$CO$_2$H (20.5 g, 325 mmol) was added. After 15 minutes the reaction mixture was warmed to room temperature and stirred for 3 hours. The reaction mixture was then filtered through celite and the organics concentrated to obtain an oil. The crude material was diluted with ethyl ether, and the salts removed by filtration. Purification on silicagel (Hexane/Ethyl Acetate: 98/2) afforded 19.6 g of compound 4.

Step 5

Compound 5

Compound 4 (3 g, 15.6 mmol) was dissolved in ethanol (32 ml) and a solution of potassium hydroxide (4.4 g, 78.1 mmol) in water (16 ml) was added. The reaction mixture was stirred overnight at room temperature. The reaction mixture was poured into 1N HCL and extracted with MTBE. The combined organic layers were washed once with 1N sodium hydroxide and brine. The crude material (compound 4, 28 g) was used in the next step without further purification.

Step 6

Compound 6

L-Serine Benzylester HCl (14.14 g, 61 mmol) was dissolved into 170 mL of $CH_2Cl_2$ followed by the addition of HBTU (22.36 g, 72.14 mmol), $Et_3N$ (29 mL, 166.47 mmol), and compound 4 (2.8 g, 11.93 mmol). The reaction mixture was stirred at room temperature for 18 hours and quenched by pouring into 1N HCl. The mixture was extracted four times with $CH_2Cl_2$. The combined organic layers were dried over $MgSO_4$ and then concentrated. Purification of the crude material by flash column chromatography using Hexane/Ethyl acetate: 70/30 afforded 18.9 g of compound 6.

Step 7

Compound 7

Compound 6 (18.33 g, 51.57 mmol) was dissolved in 50 mL of DMF and TBSCl (8.16 g, 54.14 mmol) and imidizole (8.78 mg, 128.93 mmol) were added and stirred overnight at room temperature. The reaction mixture was poured into water and extracted three times with MTBE. The combined organic layers were washed with 1N HCl, water and with a saturated solution of sodium bicarbonate. The crude material was purified by flash column chromatography with Hexane/Ethyl Acetate: 80/20 to give 23.8 g of compound 7.

Step 8.

Compound 8.

Compound 7 (2.0 g, 4.3 mmol) was dissolved in 20 mL of MeOH, followed by the addition of Pd/C 10%/wt (20 mg). The solution was then flushed with hydrogen and stirred for 2 hours under hydrogen at room temperature. The reaction mixture was then filtered through celite and the organics concentrated to obtain 1.60 g of compound 8. The crude material is used without further purification.

Step 9.

Compound 9.

N-benzyloxycarbonyl leucine methyl ester (79 g, 285 mmol) was dissolved in 3000 ml of dry toluene. The solution was cooled at −78 C and a 1M solution of DIBAl-H (598 ml, 598 mmol) was added dropwise. After 1 hour at −78 C, 108 ml of a saturated aqueous solution of NH4Cl were added at −78 C. The reaction mixture was warmed to 0 C and poured into 3000 ml of Ethyl Ether. The resulting slurry was vigorously stirred for 1 hour, and then the aluminum salts were filtered out and washed several times with ethyl ether. The combined organic layers were concentrated to give 75 g of crude compound 9. The crude material is used in the next step without further purification.

Step 10.

Compound 10.

Compound 9 (285 mmol) and 3-tert-buthyldimethylsilyloxy-2-bromopropen (71.3 g, 64 mmol) were then dissolved in dry DMF (1600 mL) under nitrogen. The mixture was cooled at 0 C and $CrCl_2$ (64 g) and $NiCl_2$ (0.64 g) were added. The reaction was stirred overnight. The reaction mixture was poured into 4000 ml of water and extracted five times with MTBE. Combined organic layers were washed three times with water and once with a saturated solution of sodium bicarbonate then dried over $MgSO_4$ and concentrated. The crude green oil was then purified by column chromatography using Hexane/MTBE/i-PrOH (90/10/1) to afford 16.5 g of compound 10.

Step 11.

Compound 11.

Compound 10 (16.5 g mmol) was dissolved into 156 mL of toluene. VO(acac)$_2$ (0.42 g, 0.1.9 mmol) was added followed by tBuOOH (15.6 mL of a 5-6M solution). The resulting deep red solution was stirred for 3 hours at room temperature. The reaction was quenched with sat. sodium sulfite, washed with MTBE, and dried with $MgSO_4$. Crude was purified by flash column chromatography using hexanes:EtOAc (80/20) to give 14 g of compound 11.

Step 12.

Compound 12.

Compound 11 (1 g, 2.3 mmol) was dissolved in 25 mL of ethyl acetate, followed by the addition of Pd/C 5%/wt (160 mg). The solution was then flushed with hydrogen and stirred for 2 hours under hydrogen at room temperature. The reaction mixture was then filtered through celite and the organics concentrated to obtain 0.82 g of compound 12. The crude material was used without further purification.

Step 13

Compound 13

Compound 8 (1.02 g, 2.7 mmol) was dissolved into 10 mL of dry THF, DEDBT (1.02 g, 3.4 mmol), diisopropylethylamine (0.48 mL, 3.4 mmol) were added at room temperature. The reaction mixture was stirred 15 minutes and a solution of compound 12 (0.82 g, 2.2 mmol) in 10 ml of dry THF was added. The reaction mixture was stirred at room temperature overnight. The reaction was concentrated under vacuum and the crude material purified by flash column chromatography using Hexane/MTBE/EtOH (80/19/1) to give 0.69 g of compound 13.

Step 14.

Compound 14.

DMSO (0.084 mL, 1.1 mmol) was dissolved in 5 mL of dry $CH_2Cl_2$ and the solution was cooled to −78° C. A 2M solution of $(COCl)_2$ in methylene cloride (0.4 mL, 0.68 mmol) was then added dropwise, followed by the addition of compound 13 (0.34 g, 0.52 mmol) in 5 mL of $CH_2Cl_2$. The reaction mixture was stirred at −78 C for 45 minutes and triethylamine (0.36 ml, 2.3 mmol) was added dropwise and then reaction allowed to warm to 0 C. The reaction was quenched with a saturated aqueous solution of ammonium chloride and extracted with MTBE. The combined organic layers were washed with 1N HCl, water and with a saturated aqueous solution of sodium bicarbonate. The crude material was purified by flash column chromatography using Hexane:EtOAc, (80/20) to afford 0.2 g of compound 14.

Step 15.

Compound 15.

Compound 14 (0.25 g, 0.38 mmol) was dissolved in THF then 3 ml of HF:pyridine complex were added at room temperature. After 105 minutes the reaction mixture was poured into a saturated solution of sodium bicarbonate. The resulting solution was extracted several times with MTBE. Combined organic layers were washed once with 1N HCl, twice with water and once with a saturated solution of sodium bicarbonate. The crude material was purified by flash column chromatography using $CH_2Cl_2$/EtOH (95/5) to give 0.156 g of compound 15 (ER-804191).

2) Exemplary Compounds:
| ER-# | Structure | |
|---|---|---|
| ER-804191 | 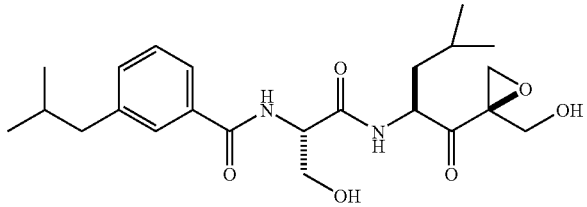 | A |
| ER-803894 | 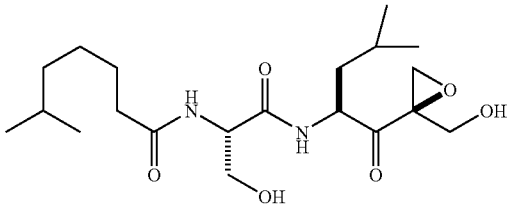 | A |
| ER-804146 | 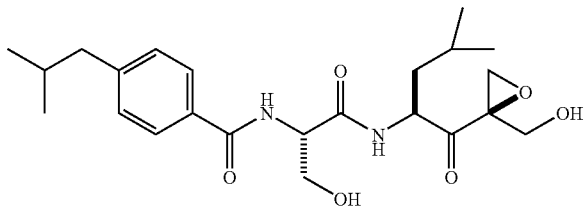 | A |
| ER-804384 | 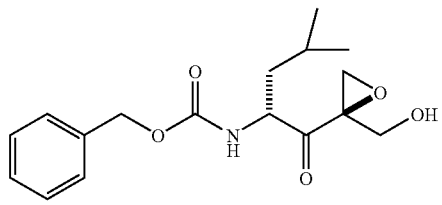 | A |
| ER-804385 | 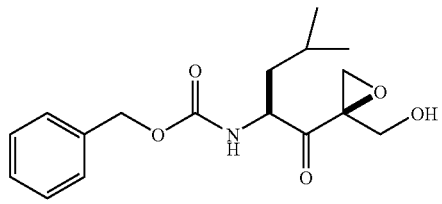 | A |
| ER-804445 | 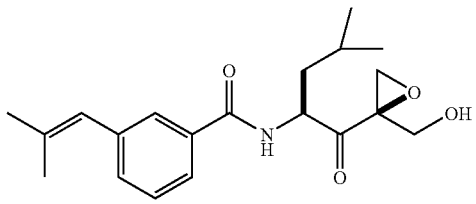 | B |
| ER-804486 | 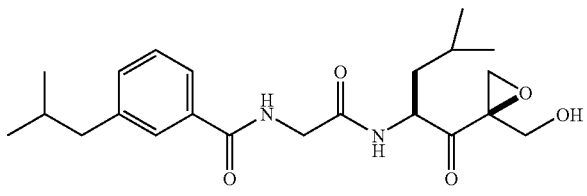 | B |

-continued
| | | |
|---|---|---|
| ER-805319 | 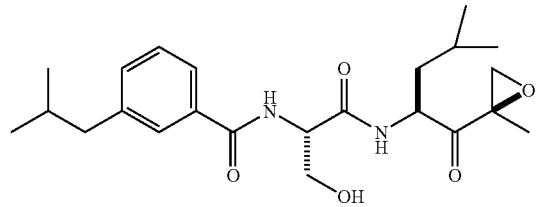 | A |
| ER-805320 | 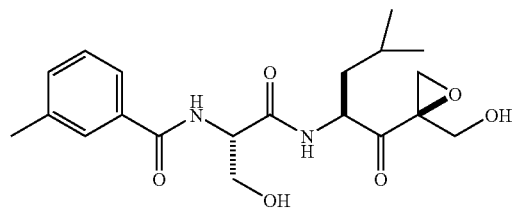 | A |
| ER-805321 | 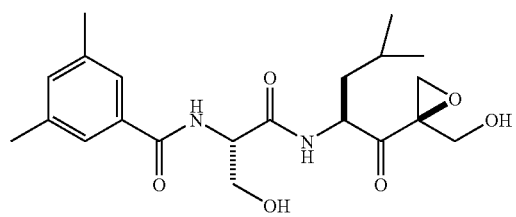 | A |
| ER-805322 | 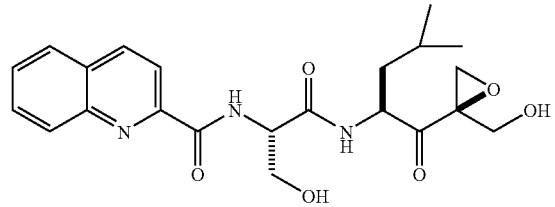 | A |
| ER-805323 | 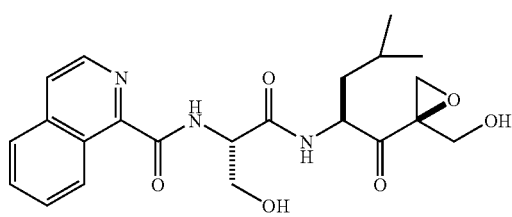 | A |
| ER-805516 | 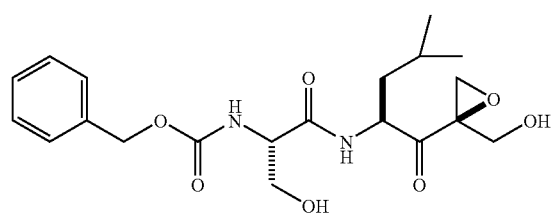 | A |
| ER-805555 | 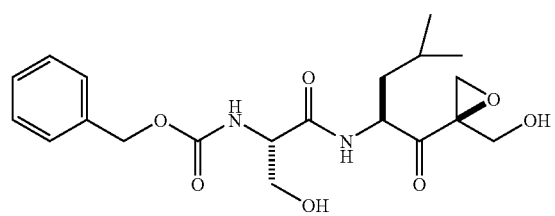 | A |

| | | |
|---|---|---|
| ER-805556 | 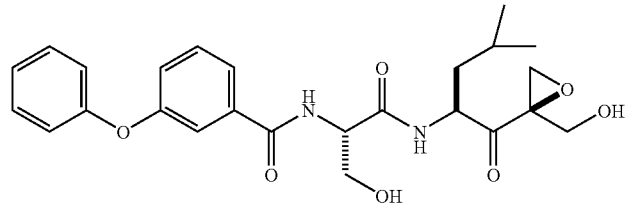 | A |
| ER-805557 | 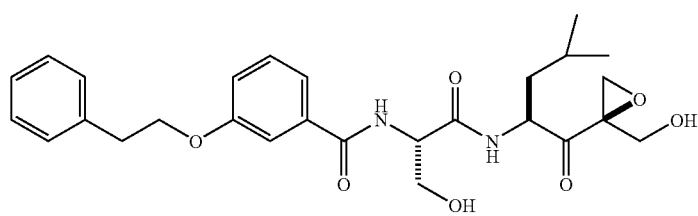 | A |
| ER-805558 | 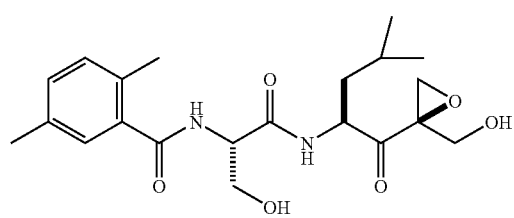 | A |
| ER-805591 | 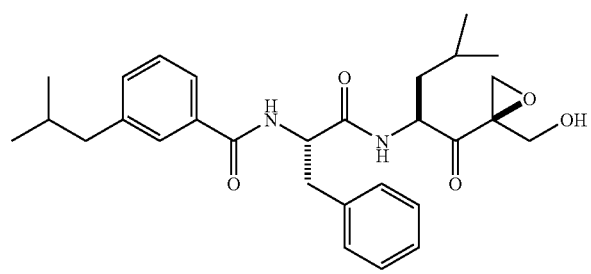 | B |
| ER-805592 | 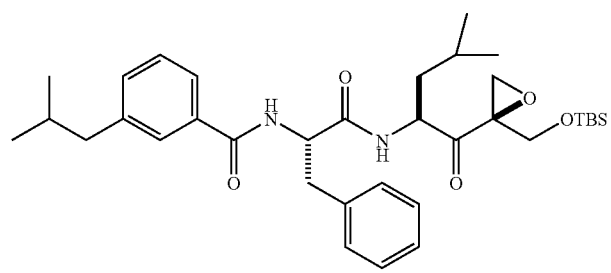 | B |
| ER-805617 | 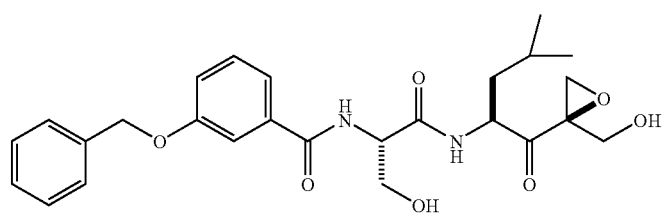 | A |

-continued
| | | |
|---|---|---|
| ER-805642 | 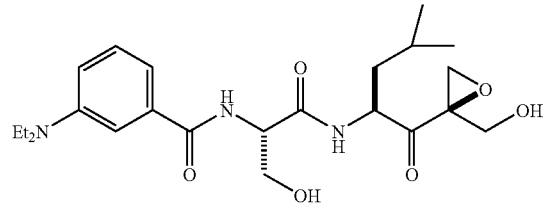 | A |
| ER-805643 | 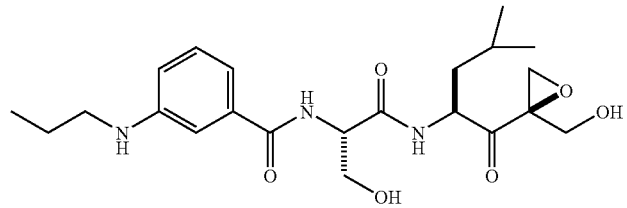 | A |
| ER-805644 | 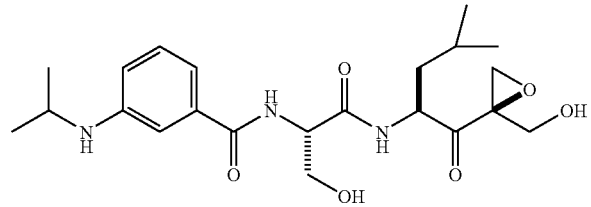 | A |
| ER-805646 | 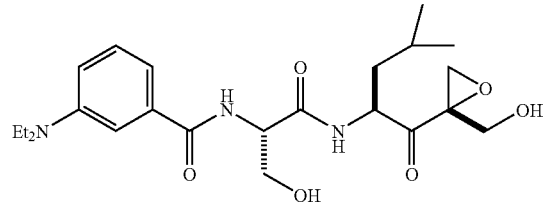 | A |
| ER-805647 | 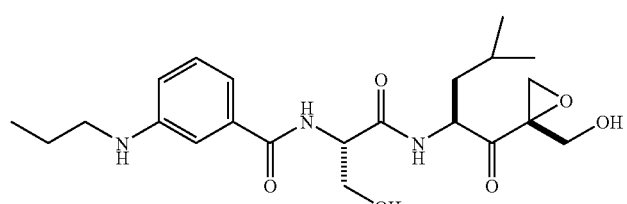 | A |
| ER-805648 | 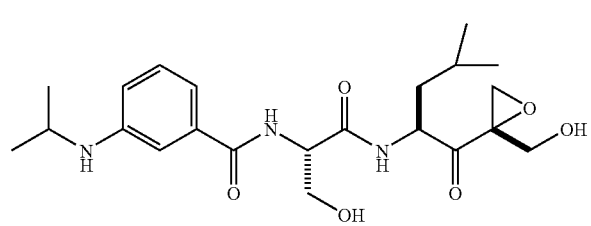 | A |
| ER-805704 | 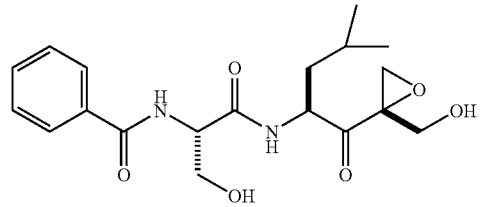 | A |

| | | |
|---|---|---|
| ER-805705 | 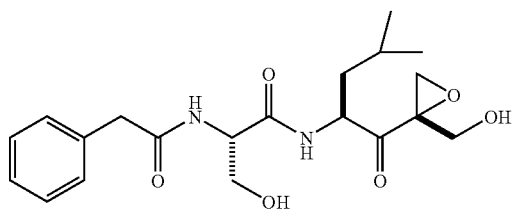 | A |
| ER-805706 | 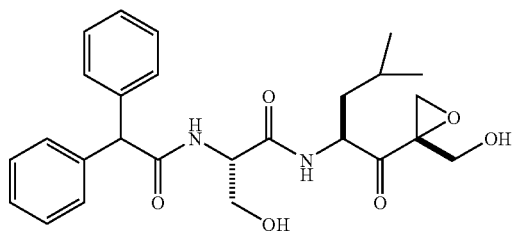 | A |
| ER-805707 | 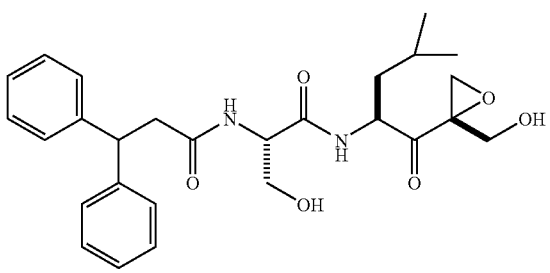 | A |
| ER-805708 | 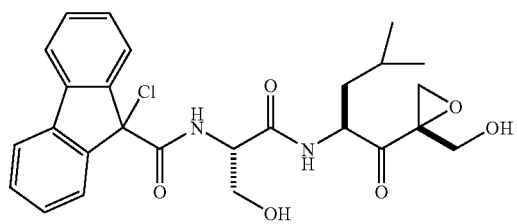 | A |
| ER-805714 | 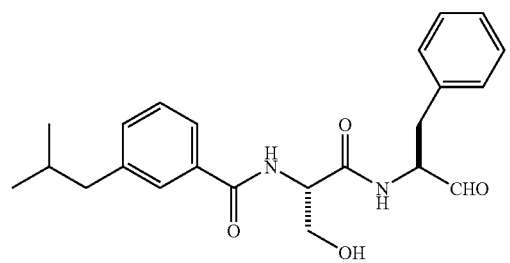 | A |
| ER-805716 | 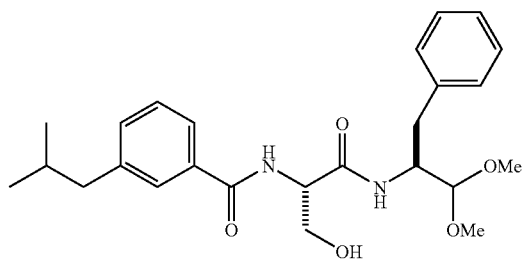 | C |

-continued
ER-805741 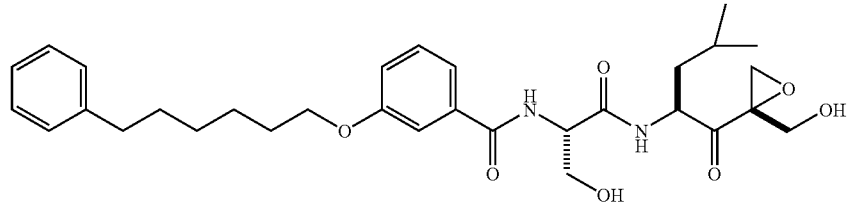 A
ER-805742 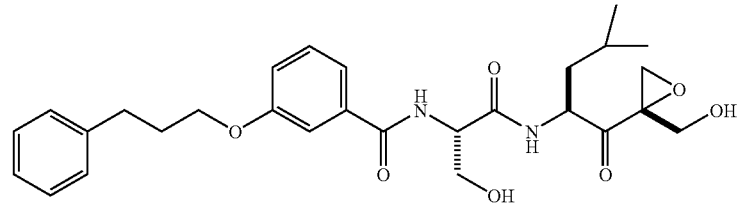 A
ER-805743 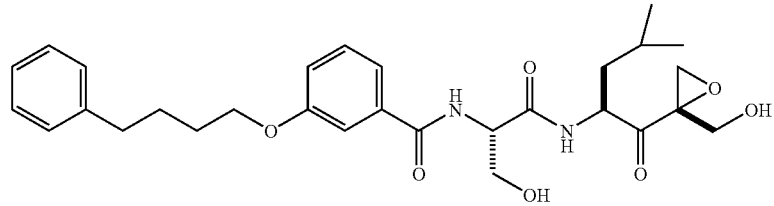 A
ER-805744 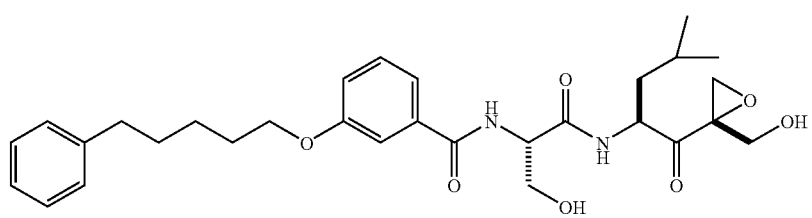 A
ER-805746 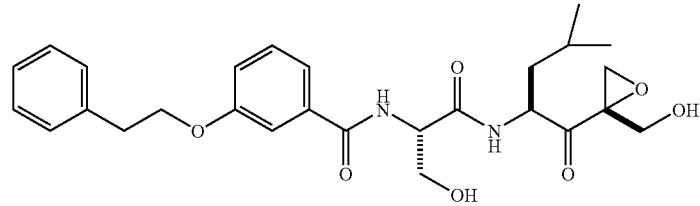 A
ER-805747 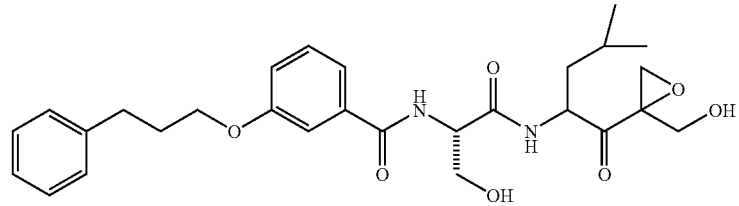 A
ER-805748 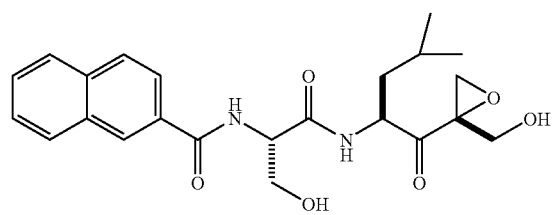 A

| | | |
|---|---|---|
| ER-805749 | 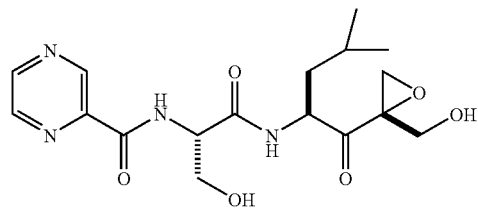 | A |
| ER-805750 | 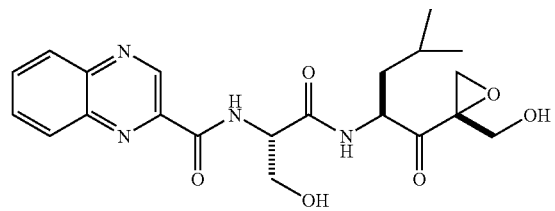 | A |
| ER-805751 | 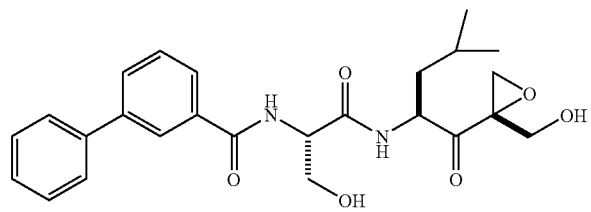 | A |
| ER-805752 | 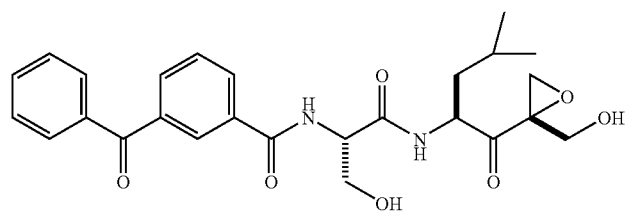 | A |
| ER-805753 | 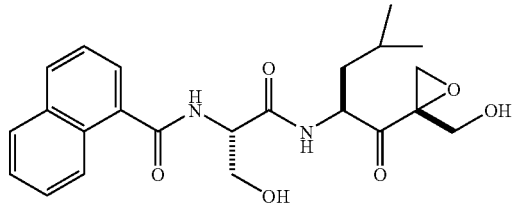 | A |
| ER-805960 | 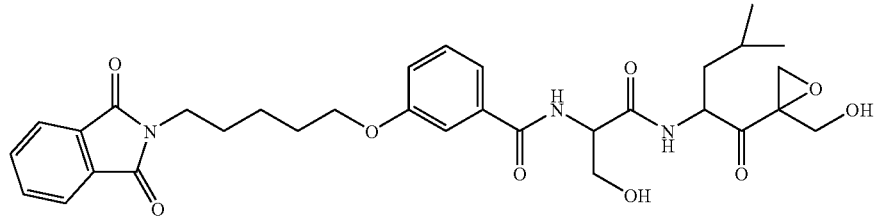 | A |
| ER-805961 | 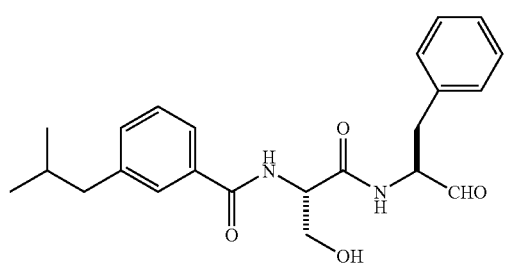 | C |

-continued
ER-805978     C
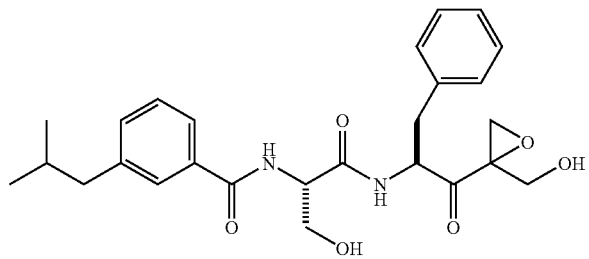
ER-805979     A
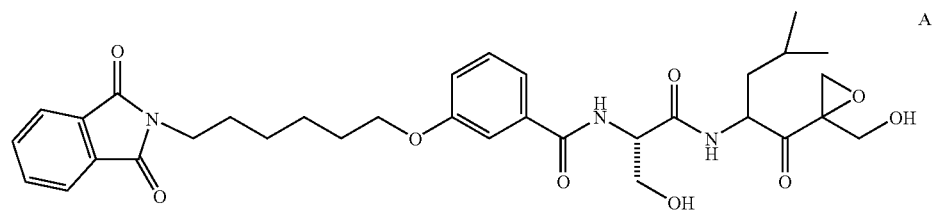
ER-805981     A
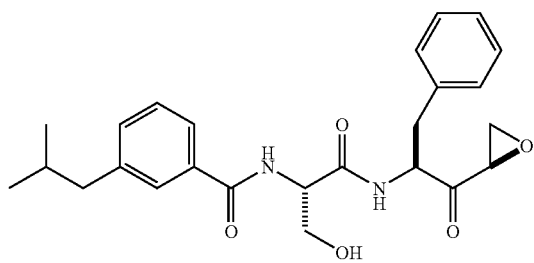
ER-805982     A
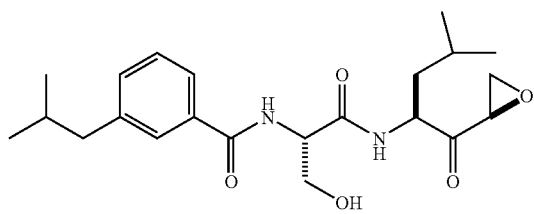
ER-806017     B
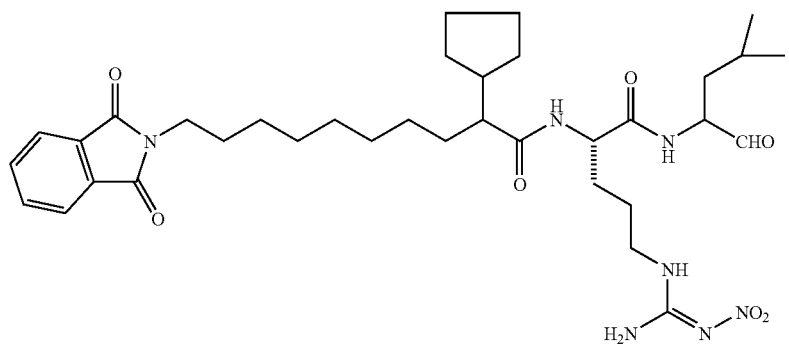

-continued
ER-806018 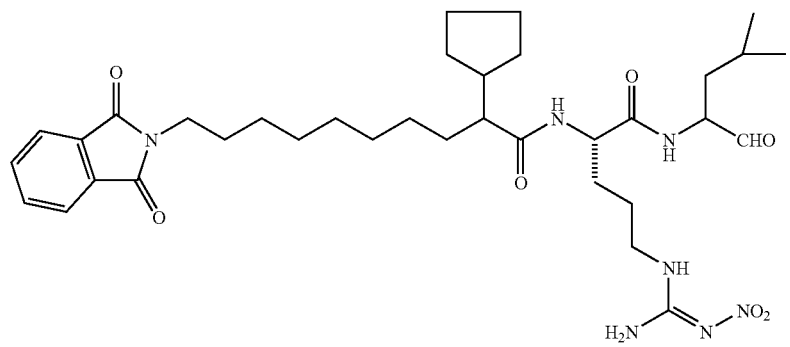 B
ER-806082 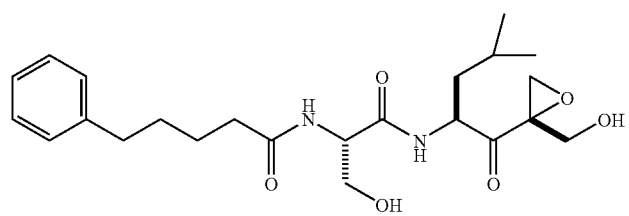 A
ER-806121 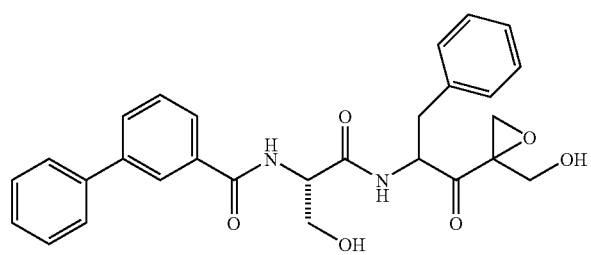 C
ER-806156 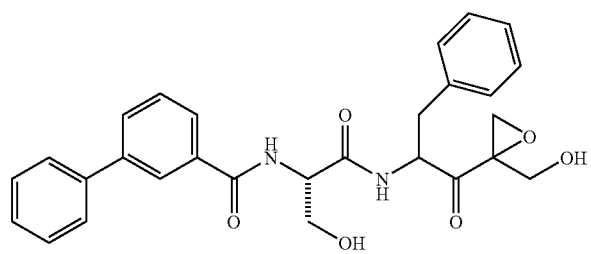 C
ER-806334 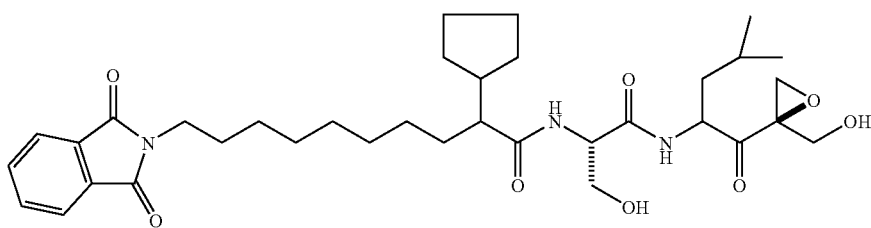 A
ER-806335 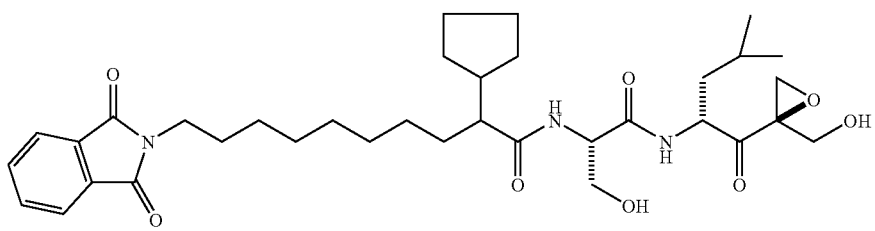 A -continued
| | | |
|---|---|---|
| ER-806337 | 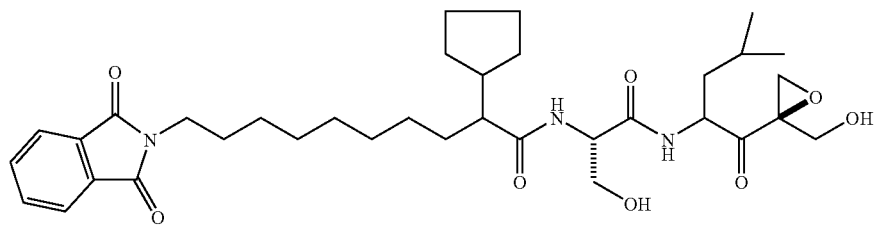 | A |
| ER-806338 | 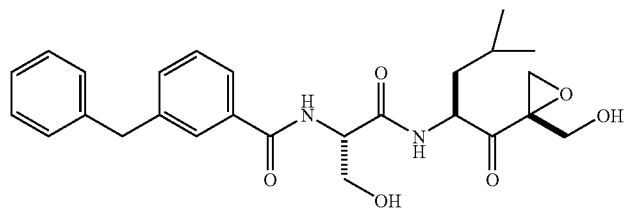 | A |
| ER-806339 | 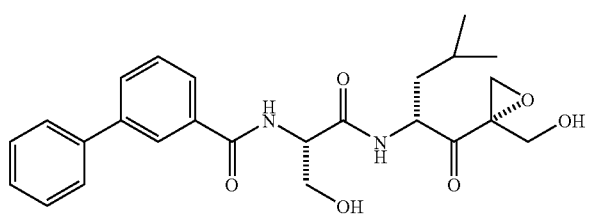 | A |
| ER-806408 | 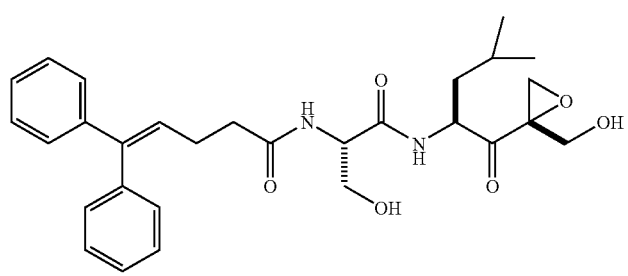 | A |
| ER-806561 | 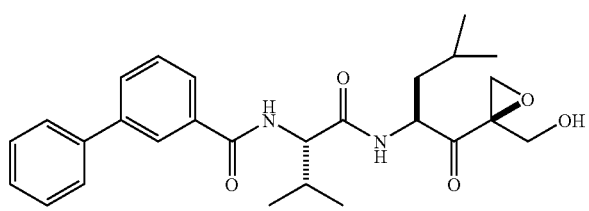 | B |
| ER-806562 | 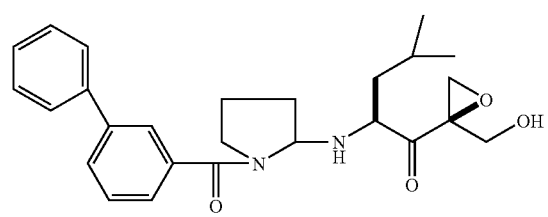 | B |
| ER-806564 | 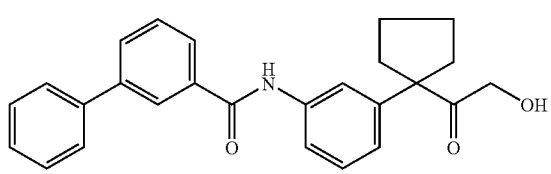 | D |

-continued
| | | |
|---|---|---|
| ER-806565 | 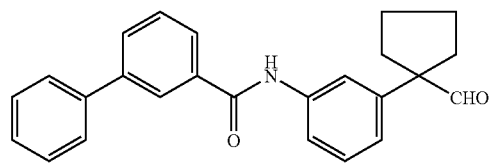 | D |
| ER-806566 | 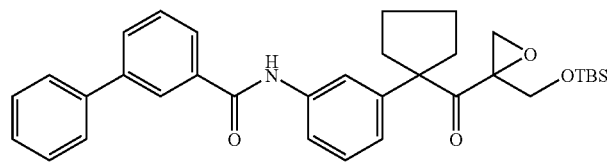 | D |
| ER-806567 | 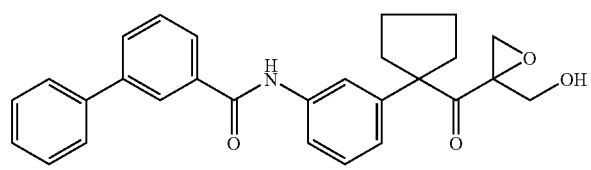 | D |
| ER-806581 | 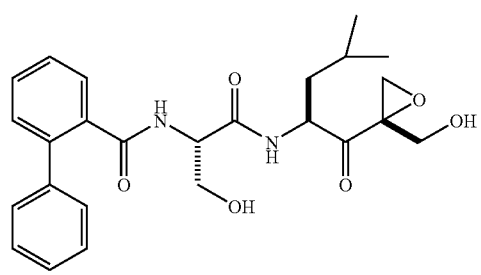 | A |
| ER-806612 | 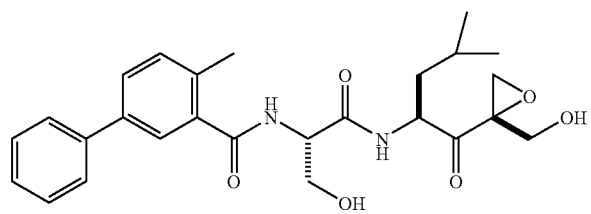 | A |
| ER-806613 | 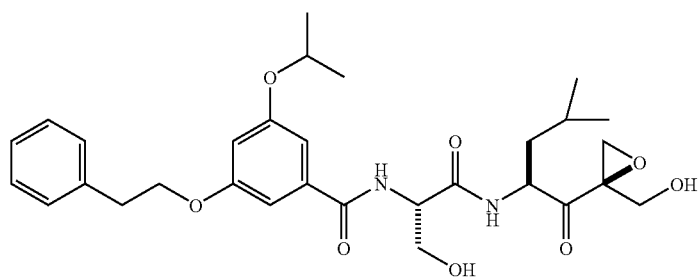 | A |
| Er-806614 | 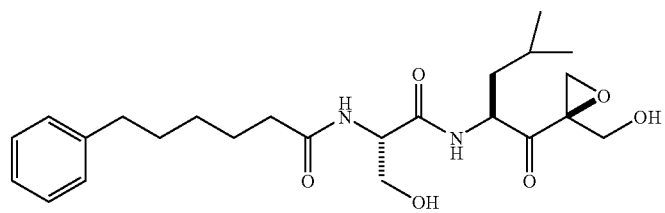 | A |

-continued
| | | |
|---|---|---|
| ER-806615 | 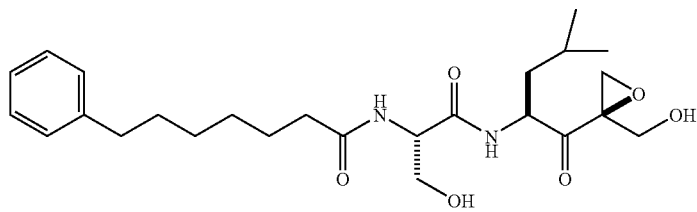 | A |
| ER-806616 | 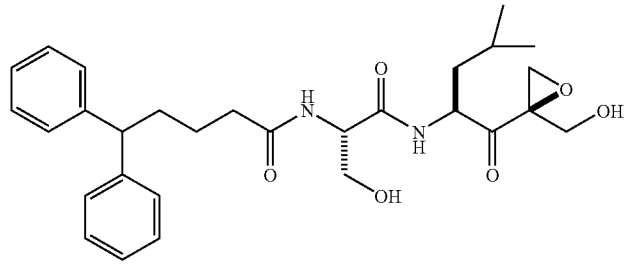 | A |
| ER-806622 | 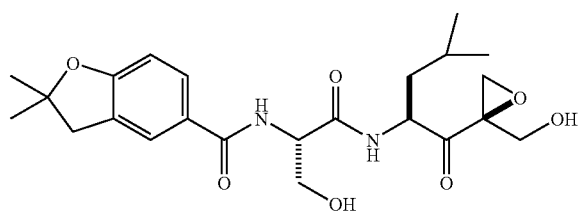 | A |
| ER-806627 | 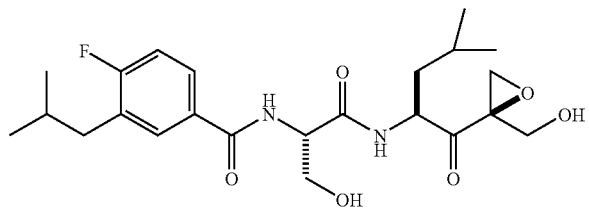 | A |
| ER-806631 | 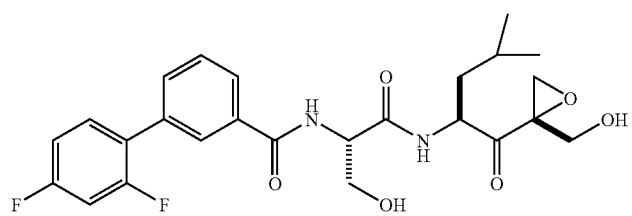 | A |
| ER-806642 | 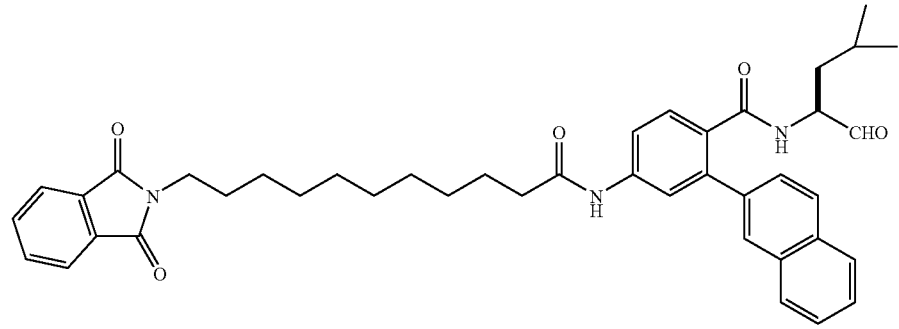 | B |

| | | |
|---|---|---|
| ER-806649 | 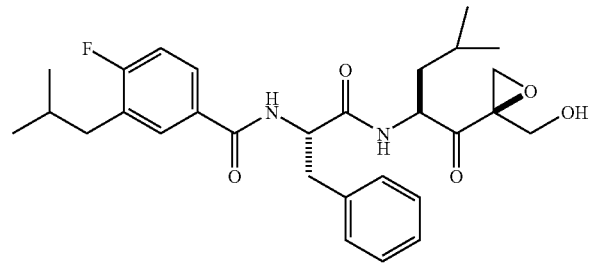 | B |
| ER-806650 | 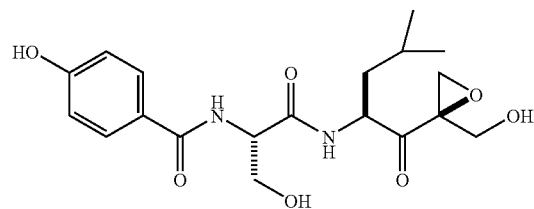 | A |
| ER-806664 | 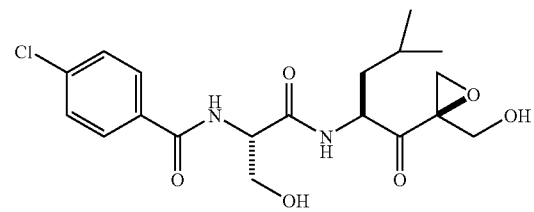 | A |
| ER-806665 | 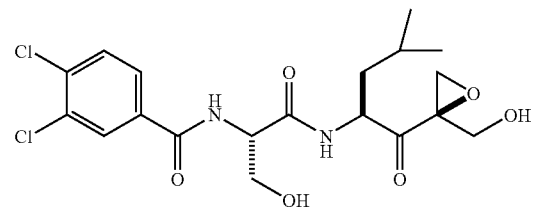 | A |
| ER-806696 | 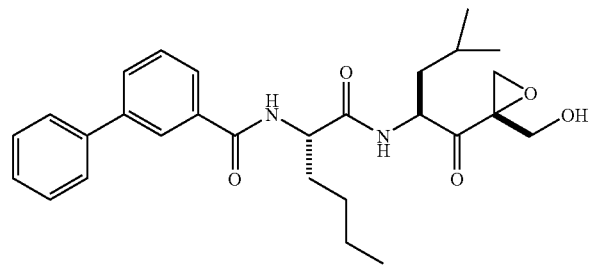 | B |
| ER-806697 | 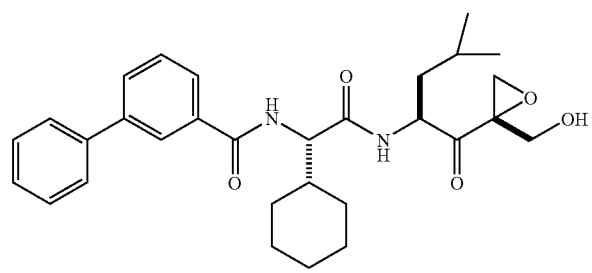 | B |

-continued
ER-806698 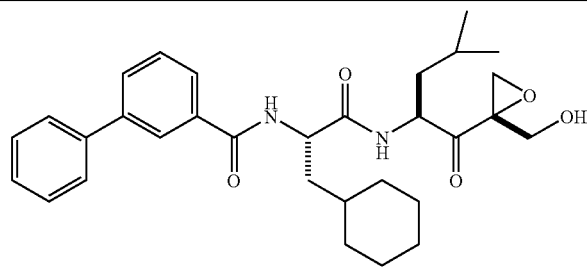 B
ER-806699 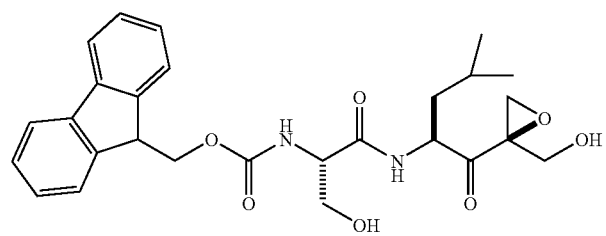 A
ER-806700 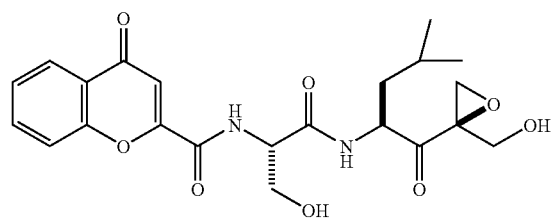 A
ER-806701 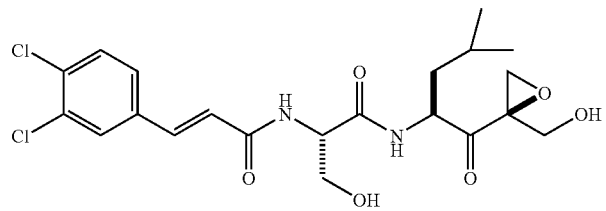 A
ER-806709 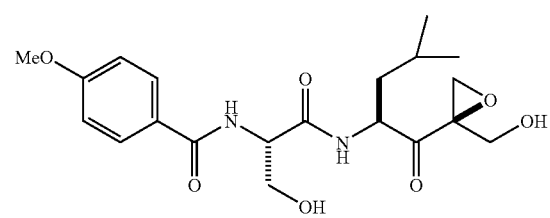 A
ER-806750 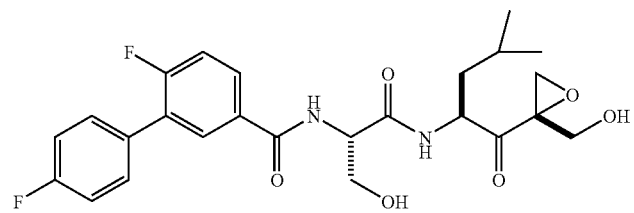 A
ER-806751 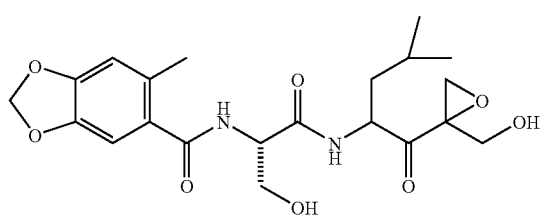 A -continued
ER-806771 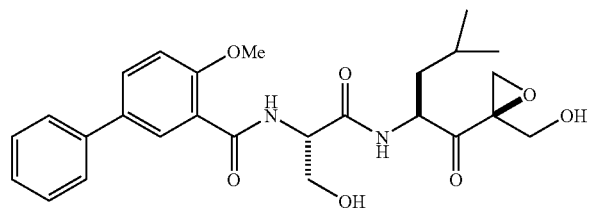 A
ER-806779 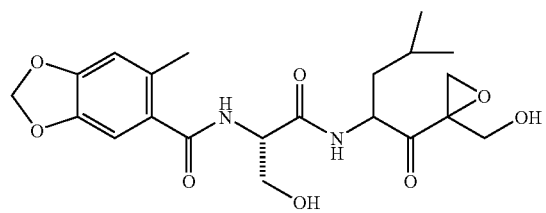 A
ER-806780 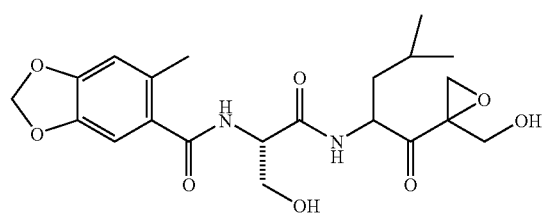 A
ER-806783 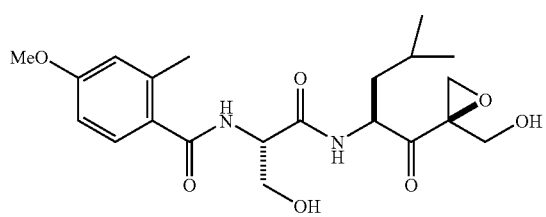 A
ER-806784 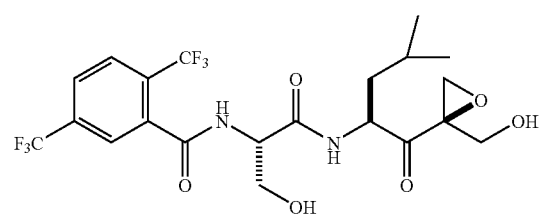 A
ER-806785 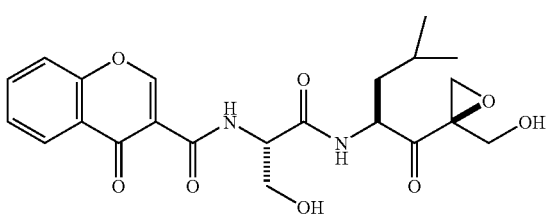 A
ER-806786 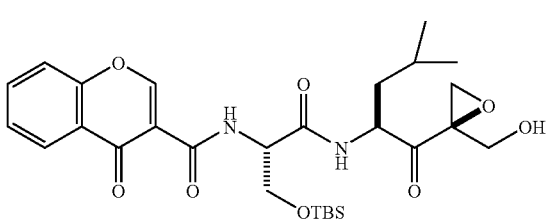 A -continued
| | | |
|---|---|---|
| ER-806787 | 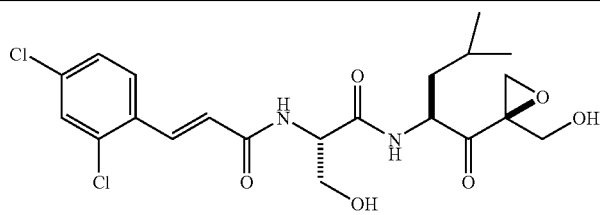 | A |
| ER-806788 | 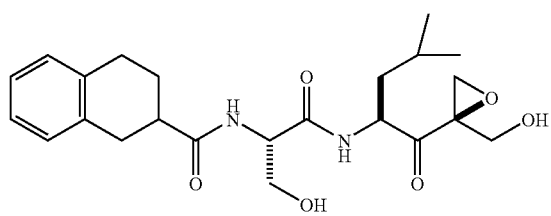 | A |
| ER-806789 | 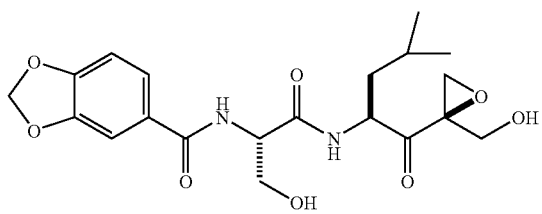 | A |
| ER-806805 | 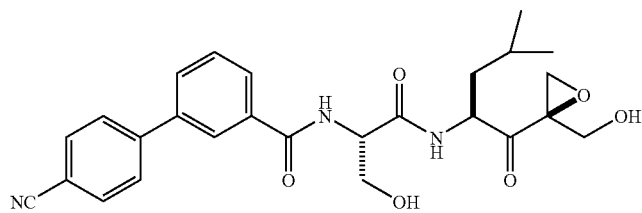 | A |
| ER-806807 | 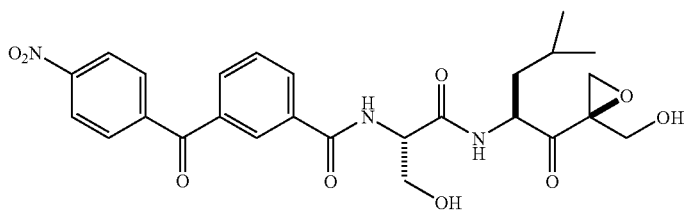 | A |
| ER-806808 | 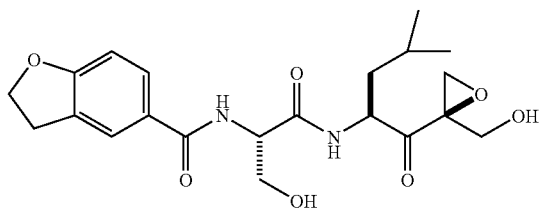 | A |
| ER-806811 | 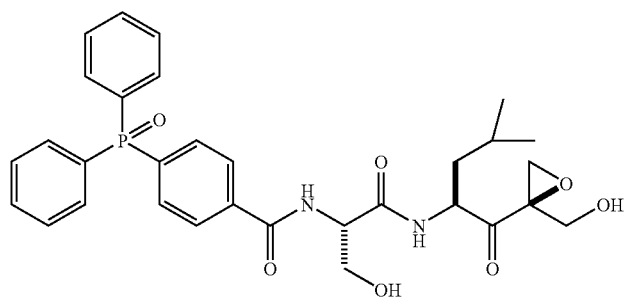 | A |

-continued
| | | |
|---|---|---|
| ER-806812 | 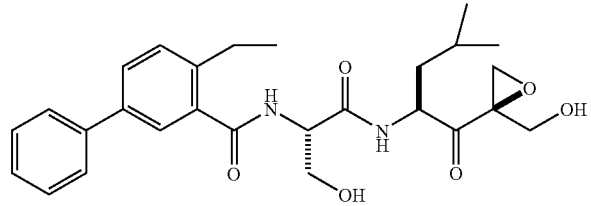 | A |
| ER-806813 | 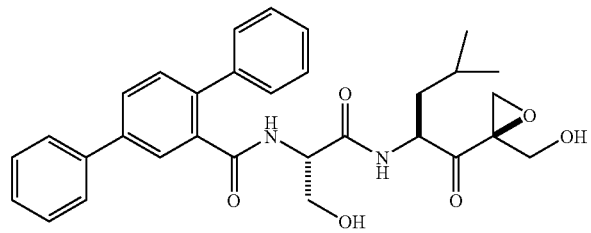 | A |
| ER-806814 | 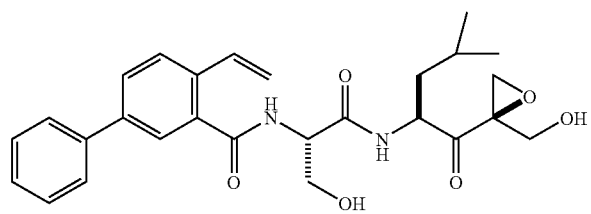 | A |
| ER-806815 | 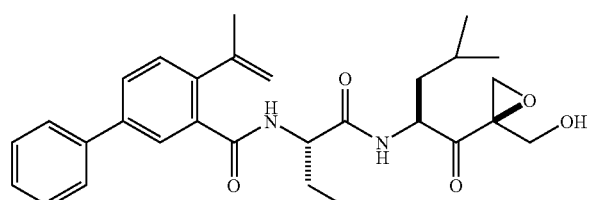 | A |
| ER-806816 | 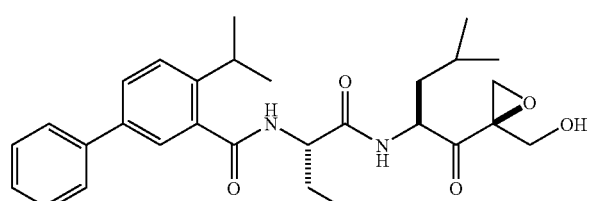 | A |
| ER-806817 | 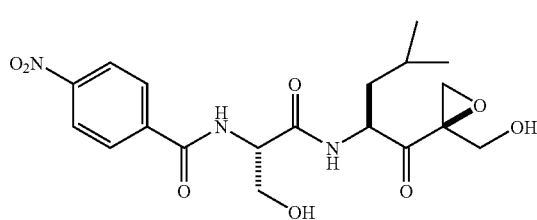 | A |
| ER-806845 | 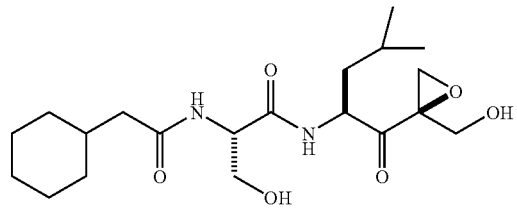 | A |

-continued
ER-806846 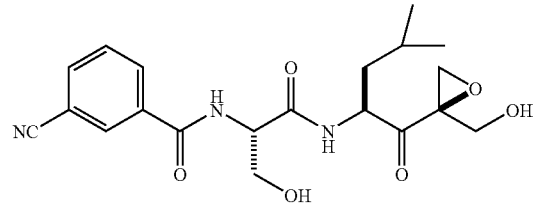 A
ER-806857 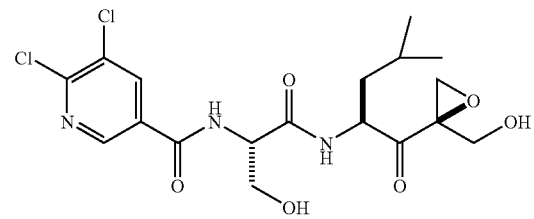 A
ER-806859 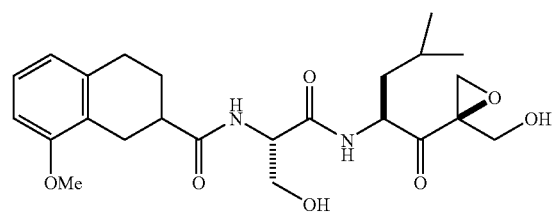 A
ER-806872 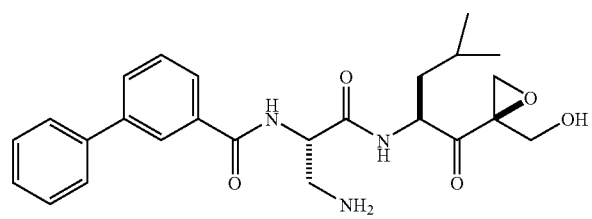 B
ER-806873 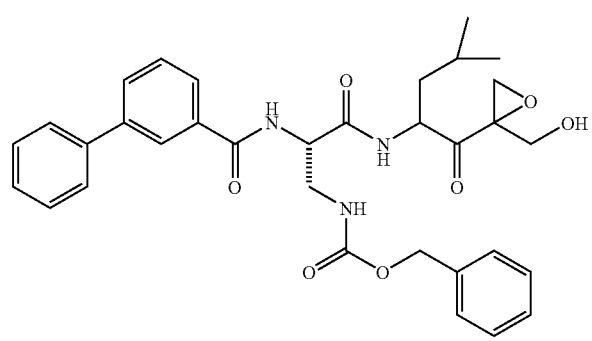 B
ER-806883 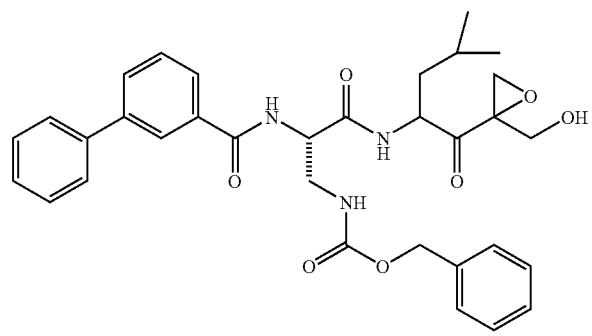 B -continued
| | | |
|---|---|---|
| ER-806884 | 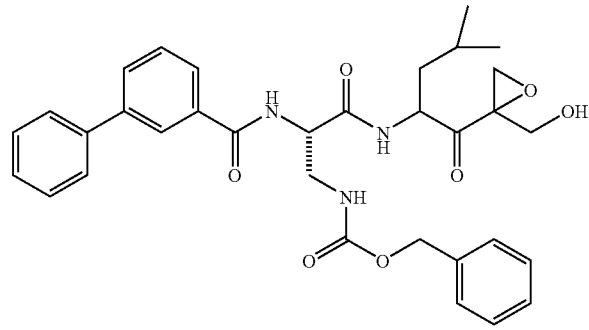 | B |
| ER-806910 | 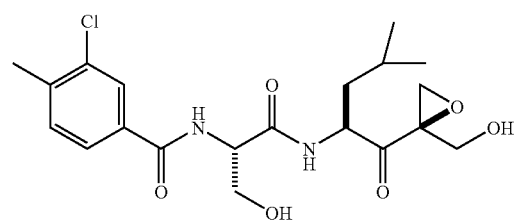 | A |
| ER-806911 | 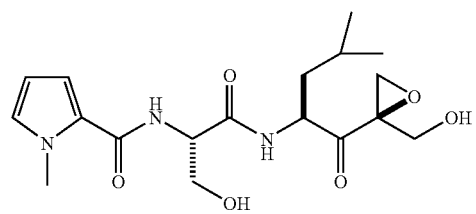 | A |
| ER-806913 | 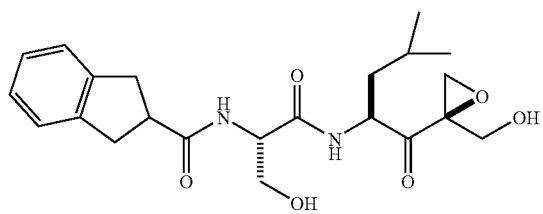 | A |
| ER-806914 | 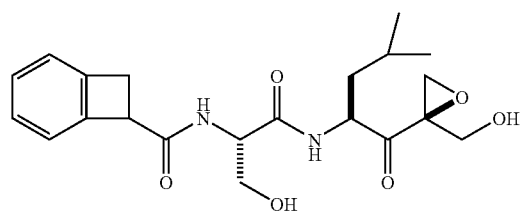 | A |
| ER-806915 | 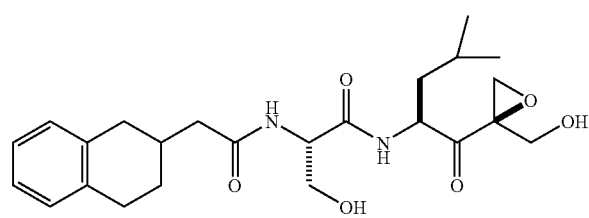 | A |

-continued
ER-806916 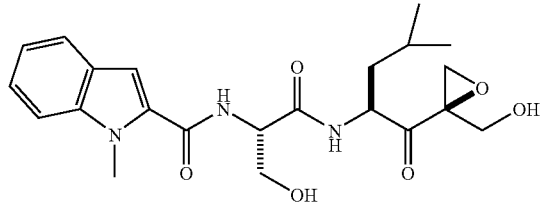 A
ER-806917 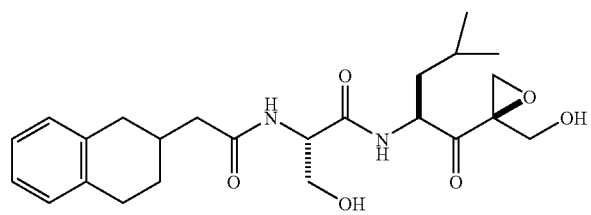 A
ER-806918 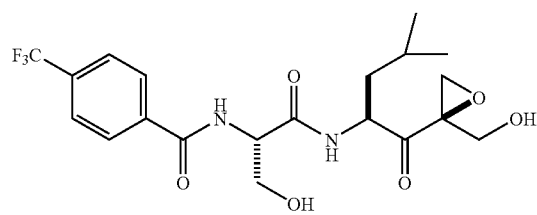 A
ER-806919 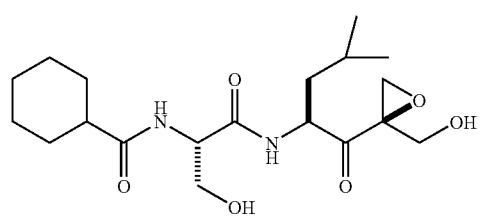 A
ER-806988 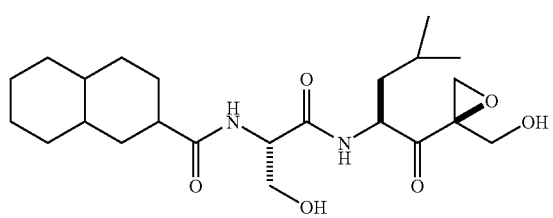 A
ER-806989 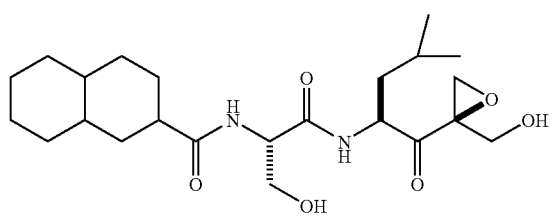 A
ER-806990 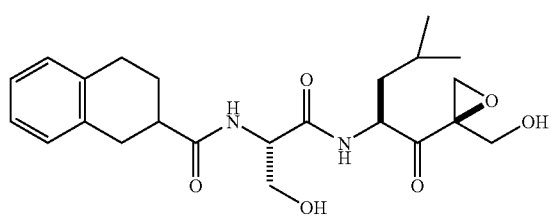 A

| | | |
|---|---|---|
| ER-806991 | 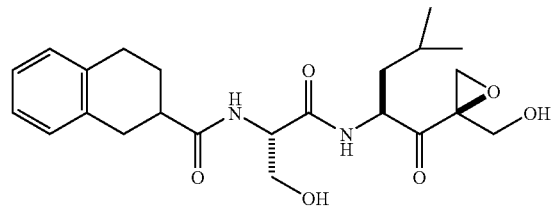 | A |
| ER-806994 | 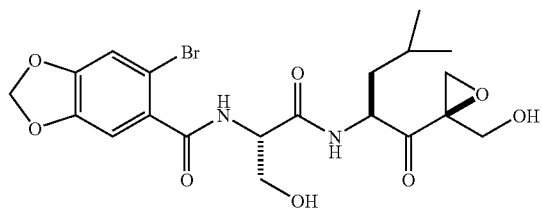 | A |
| ER-806995 | 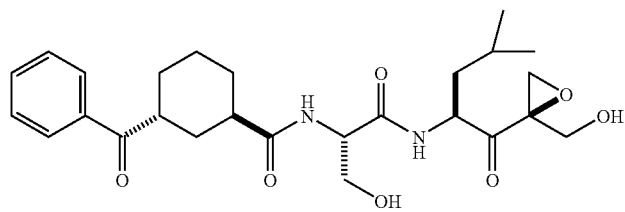 | A |
| ER-806996 | 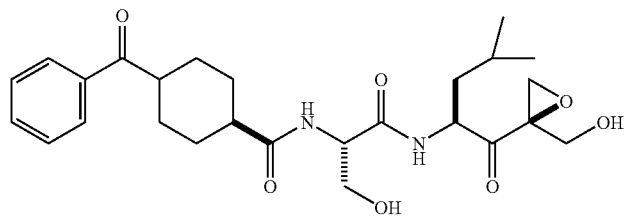 | A |
| ER-806997 | 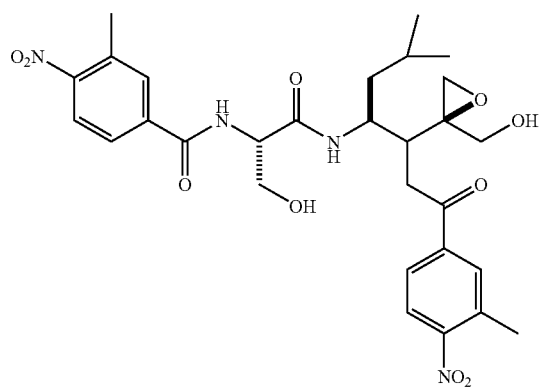 | D |
| ER-806998 | 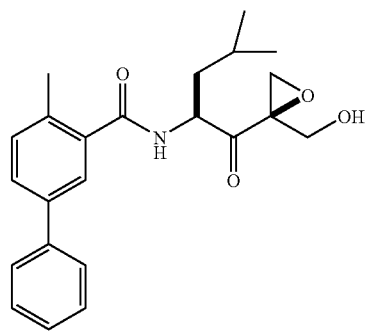 | D |

| | | |
|---|---|---|
| ER-807005 | 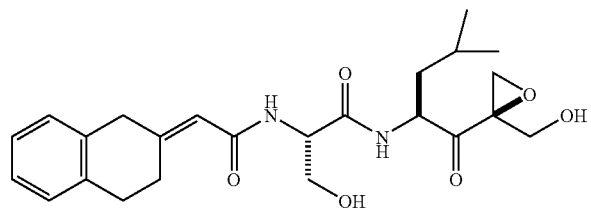 | A |
| ER-806706 | 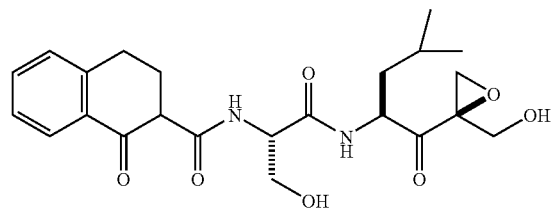 | A |
| ER-807007 | 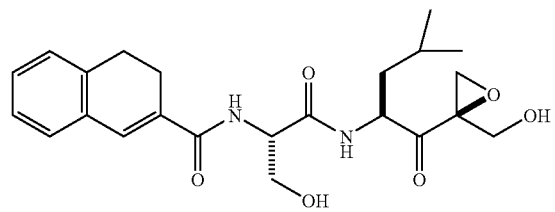 | A |
| ER-807009 | 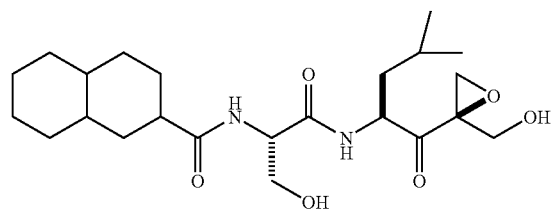 | A |
| ER-807042 | 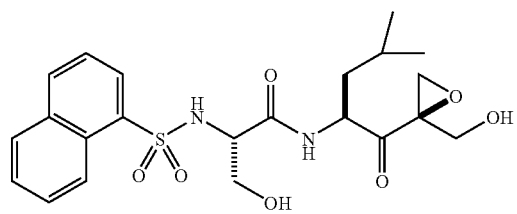 | A |
| ER-807043 | 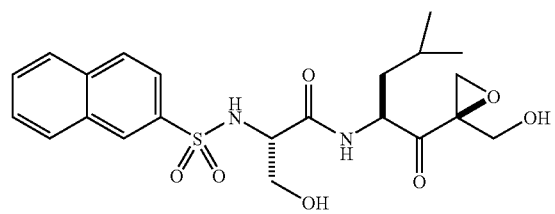 | A |
| ER-807048 | 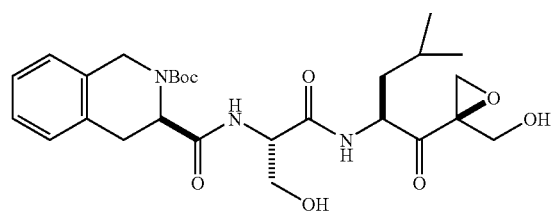 | A |

-continued
| | | |
|---|---|---|
| ER-807049 | 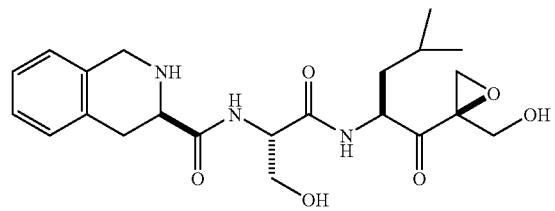 | A |
| ER-807050 | 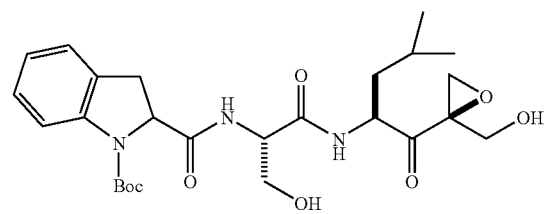 | A |
| ER-807051 | 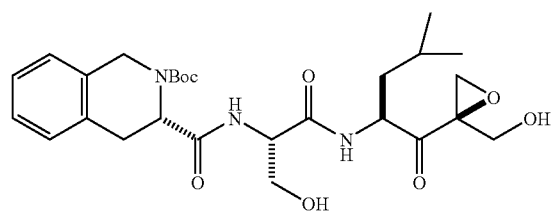 | A |
| ER-807052 | 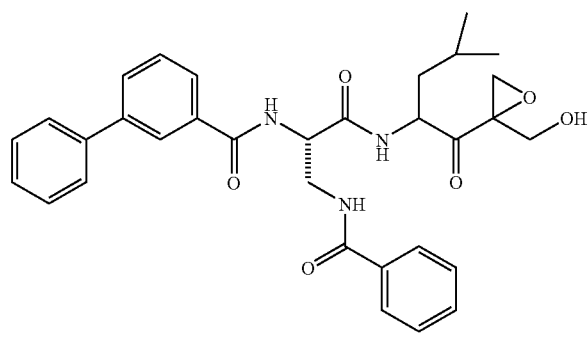 | B |
| ER-807053 | 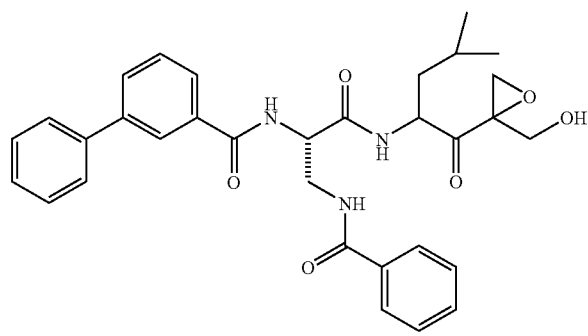 | B |

ER-807054 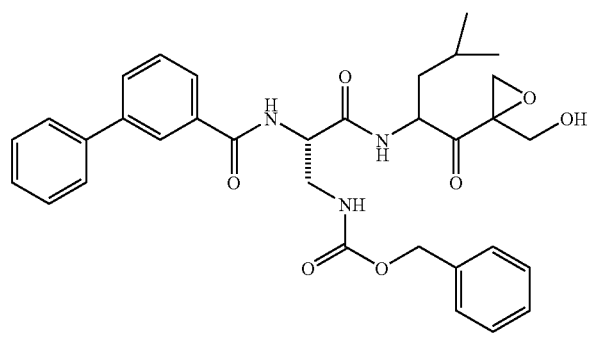 B
ER-807055 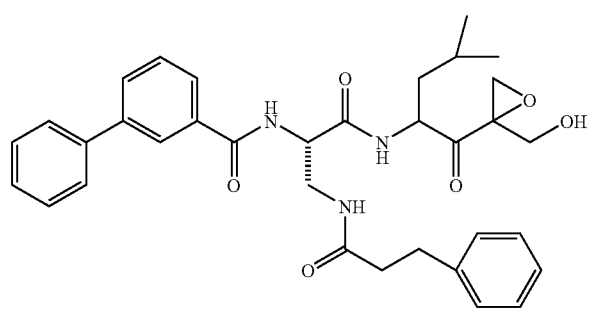 B
ER-807056 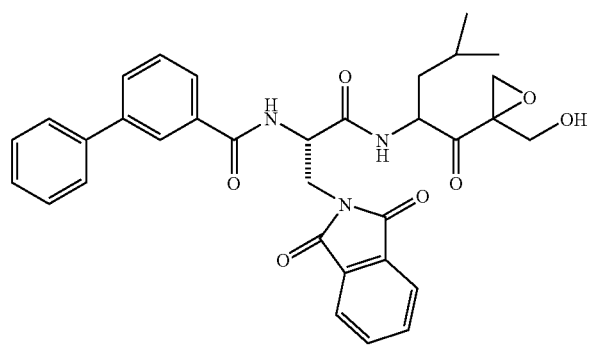 B
ER-807057 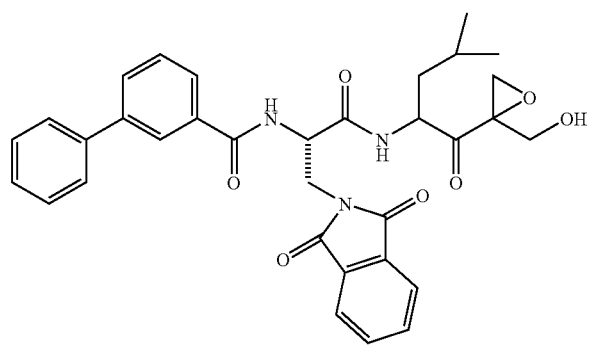 B -continued
ER-807058 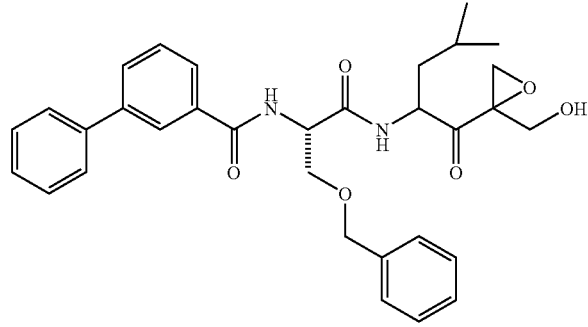 B
ER-807059 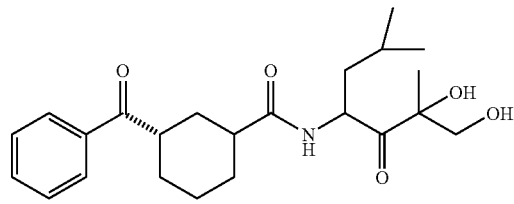 B
ER-807060 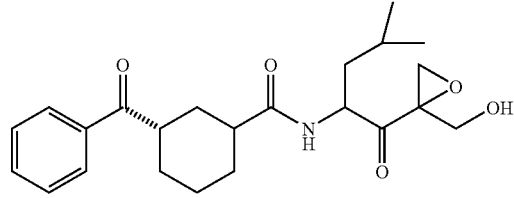 B
ER-807061 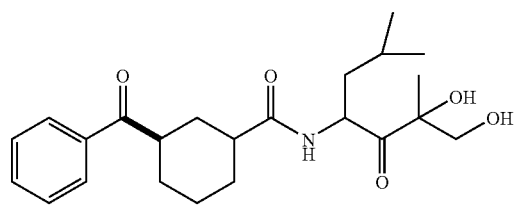 B
ER-807062 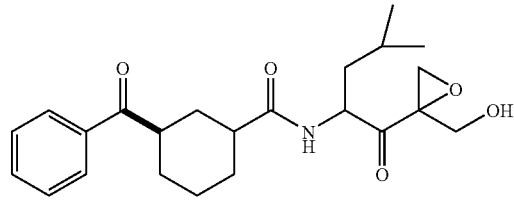 B
ER-807063 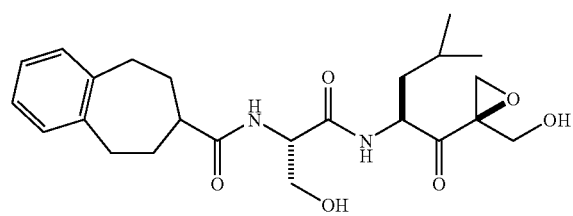 A
ER-807064 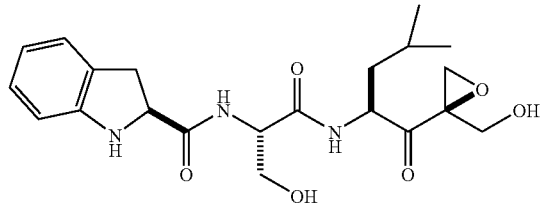 A -continued
| | | |
|---|---|---|
| ER-807065 | 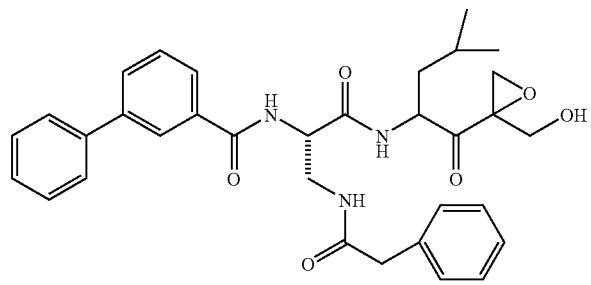 | B |
| ER-807066 | 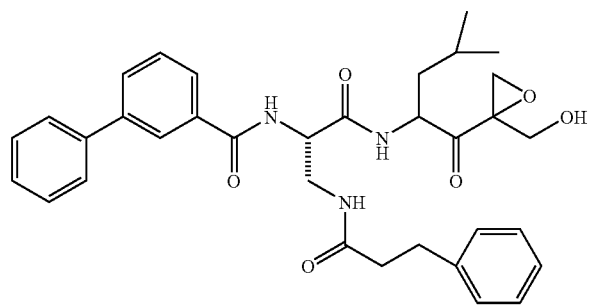 | B |
| ER-807067 | 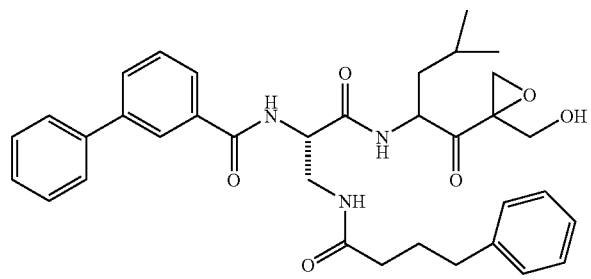 | B |
| ER-807068 | 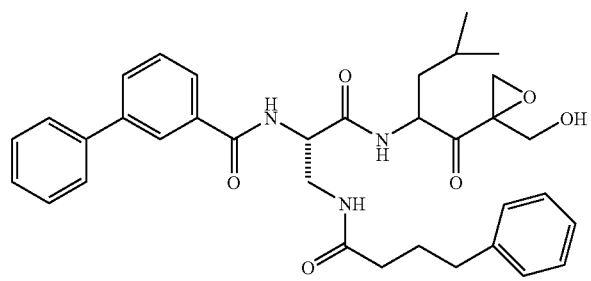 | B |
| ER-807069 | 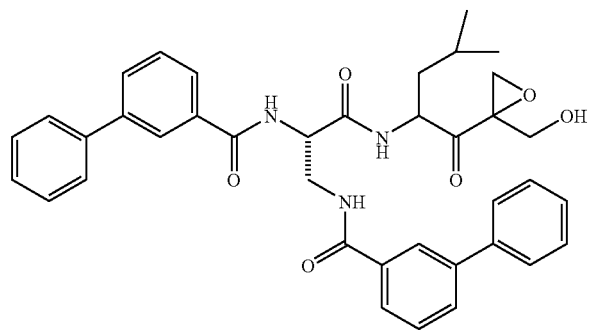 | B |

| | | |
|---|---|---|
| ER-807070 | 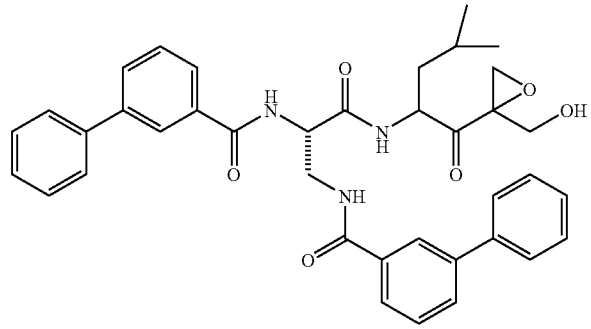 | B |
| ER-807071 | 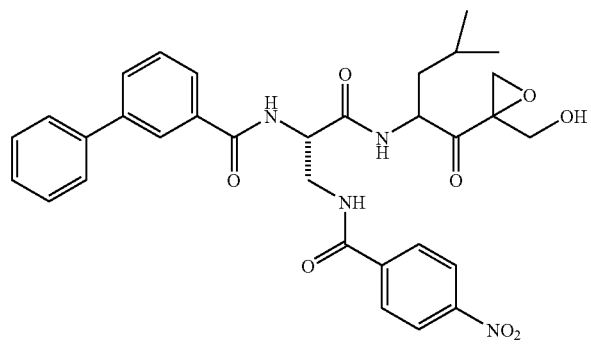 | B |
| ER-807072 | 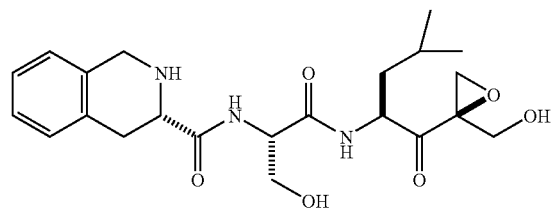 | A |
| ER-807073 | 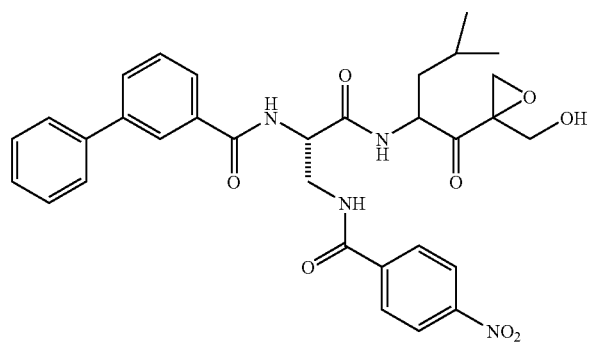 | B |
| ER-807074 | 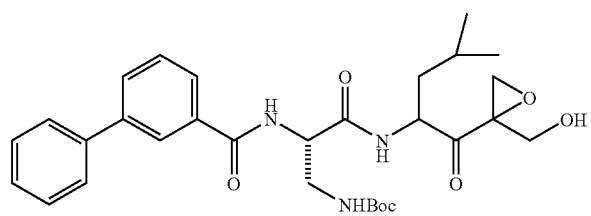 | B |

-continued
ER-807075 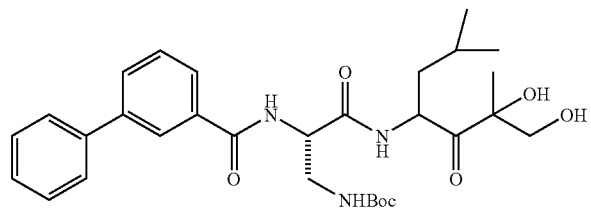 B
ER-807076 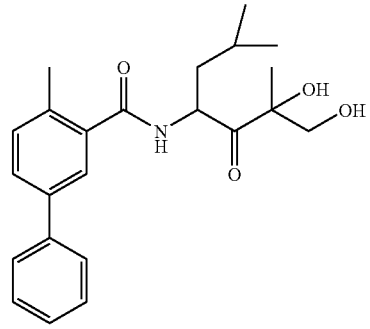 B
ER-807105 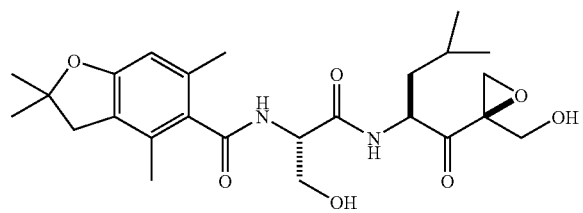 A
ER-807106 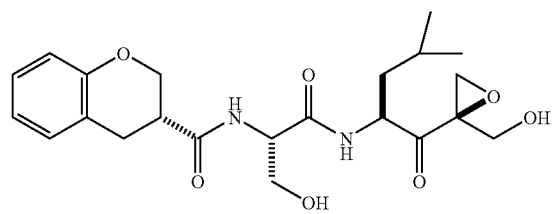 A
ER-807107 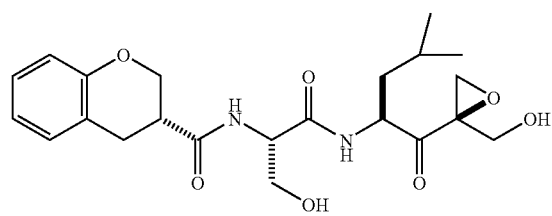 A
ER-807109 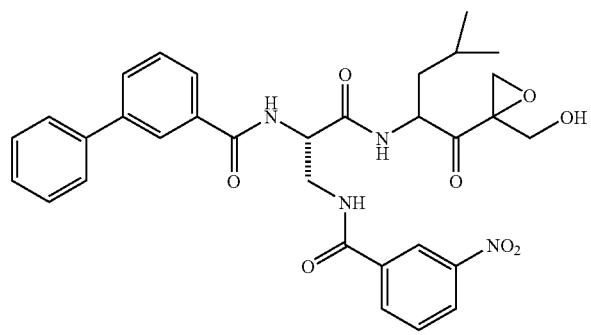 B

| | | |
|---|---|---|
| ER-807110 | 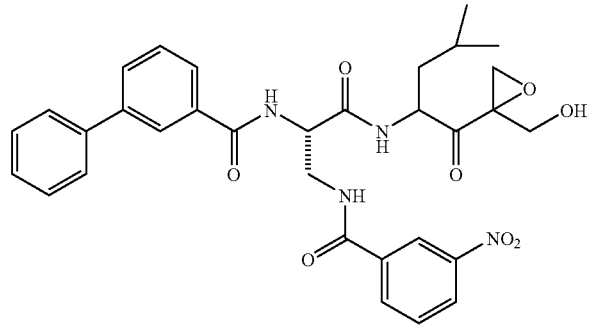 | B |
| ER-807111 | 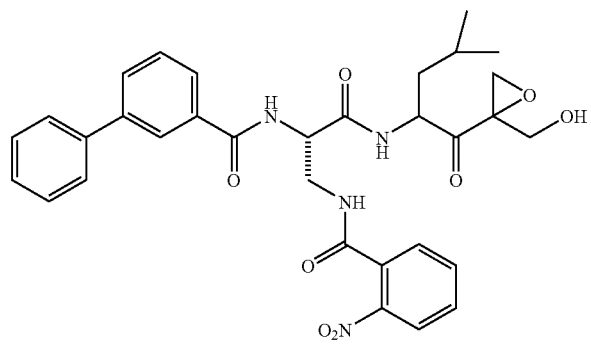 | B |
| ER-807112 | 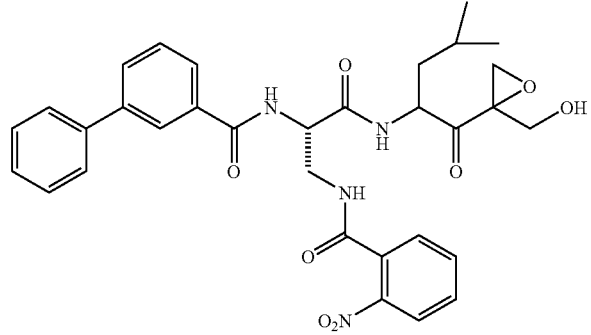 | B |
| ER-807117 | 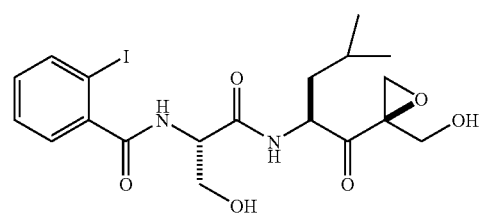 | A |
| ER-807118 | 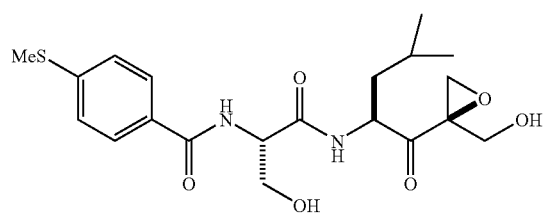 | A |

-continued
| | | |
|---|---|---|
| ER-807119 | 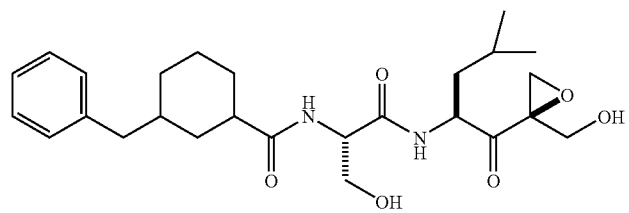 | A |
| ER-807120 | 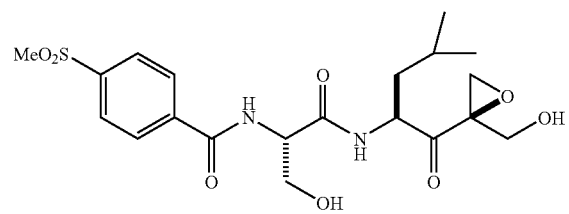 | A |
| ER-807121 | 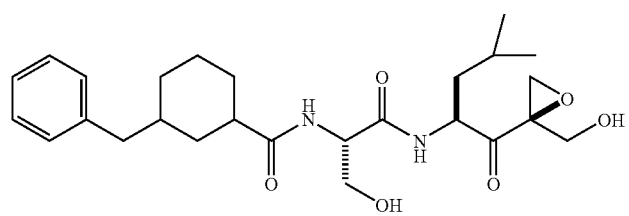 | A |
| ER-807122 | 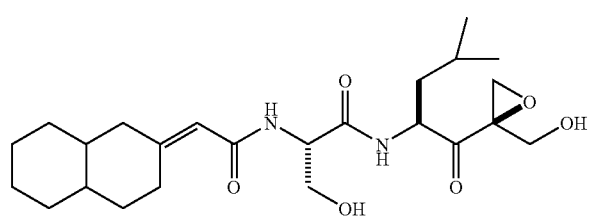 | A |
| ER-807124 | 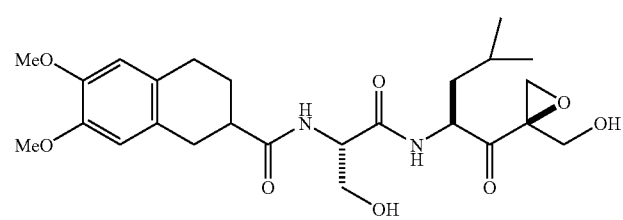 | A |
| ER-807125 | 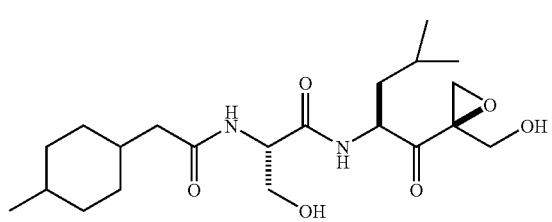 | A |
| ER-807126 | 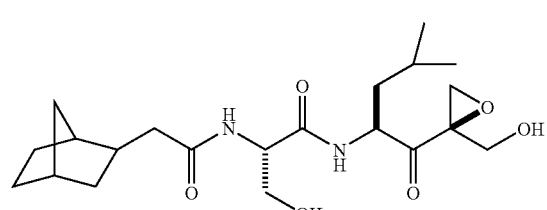 | A |

-continued
| | | |
|---|---|---|
| ER-807130 | 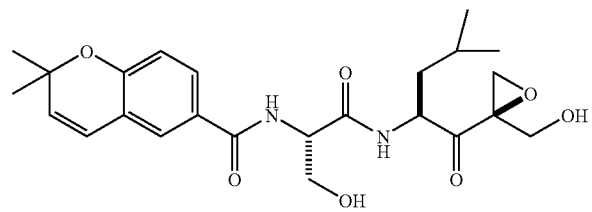 | A |
| ER-807131 | 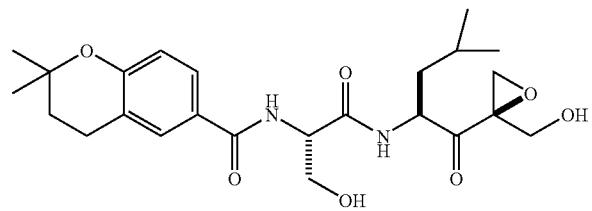 | A |
| ER-807136 | 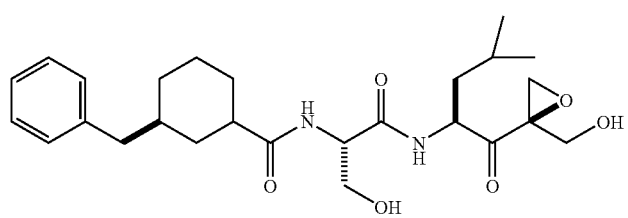 | A |
| ER-807137 | 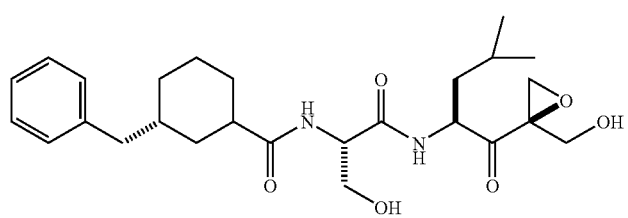 | A |
| ER-807149 | 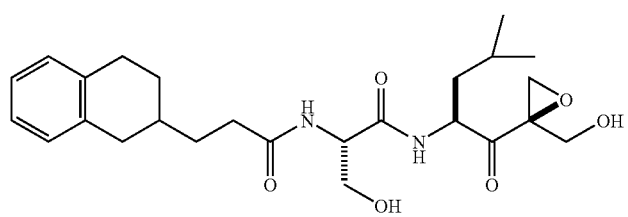 | A |
| ER-807150 | 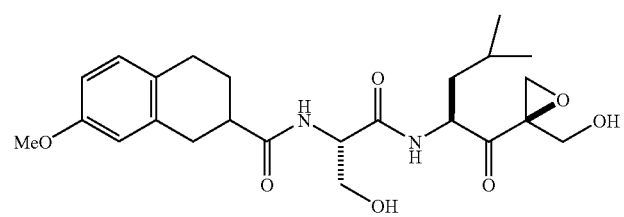 | A |
| ER-807151 | 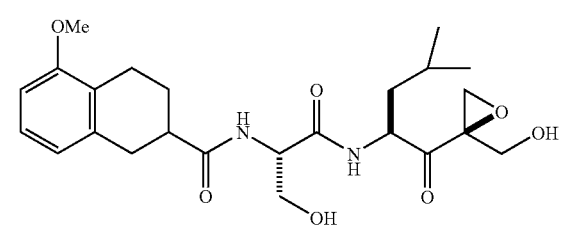 | A |

-continued
| | | |
|---|---|---|
| ER-807152 | 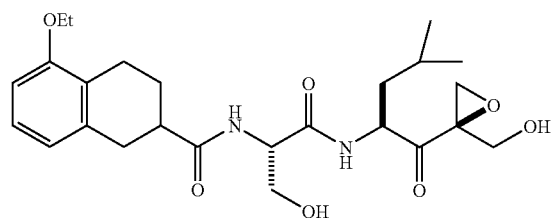 | A |
| ER-807153 | 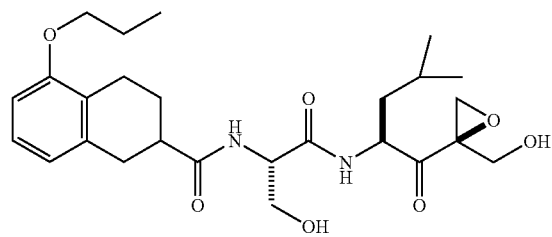 | A |
| ER-807154 | 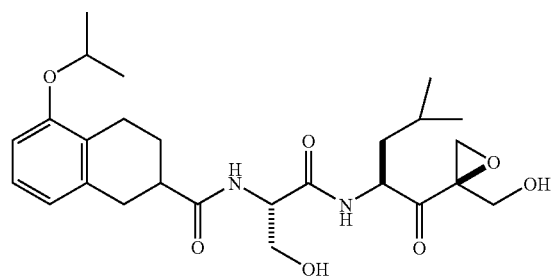 | A |
| ER-807155 | 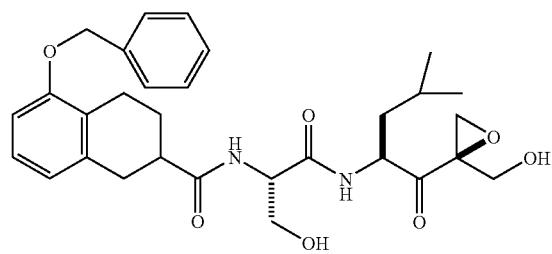 | A |
| ER-807156 | 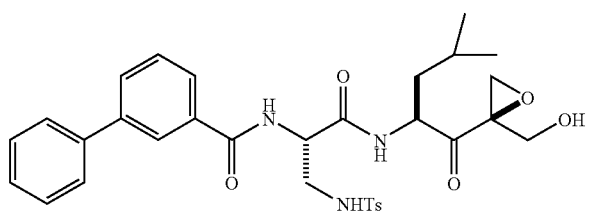 | A |
| Er-807159 | 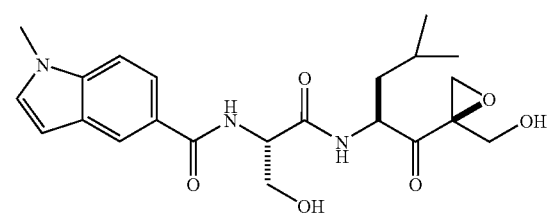 | A |

-continued
| | | |
|---|---|---|
| ER-807162 | 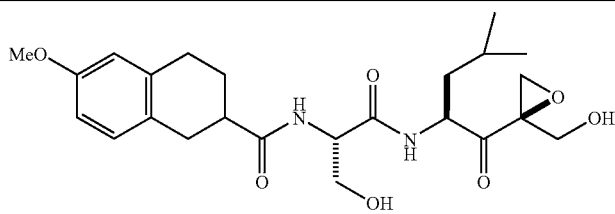 | A |
| ER-807163 | 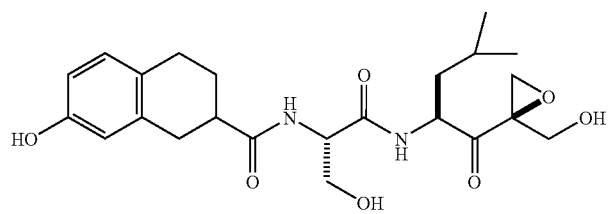 | A |
| ER-807165 | 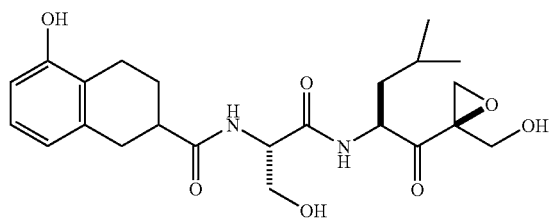 | A |
| ER-807167 | 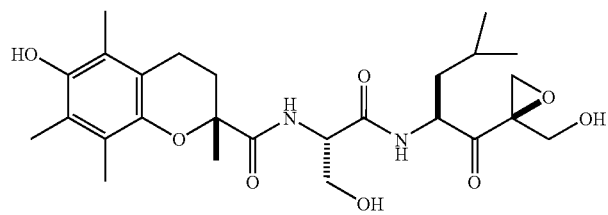 | A |
| ER-807181 | 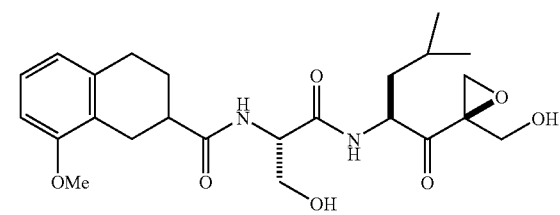 | A |
| ER-807189 | 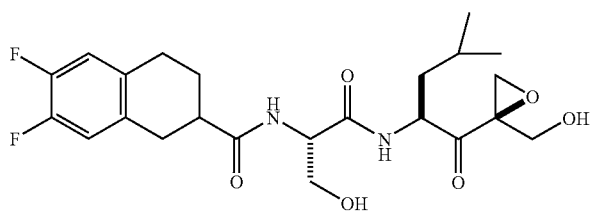 | A |
| ER-807190 | 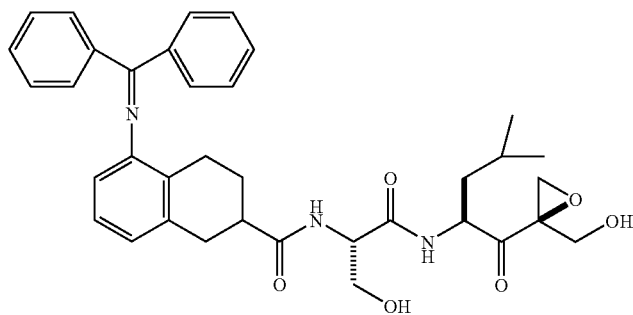 | A |

-continued
| | | |
|---|---|---|
| ER-807191 | 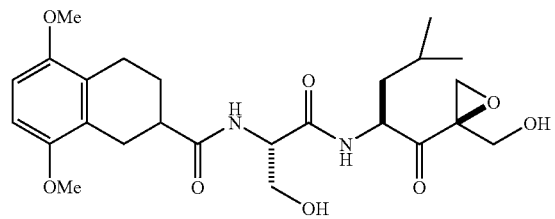 | A |
| ER-807207 | 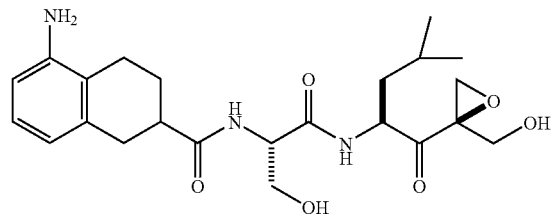 | A |
| ER-807208 | 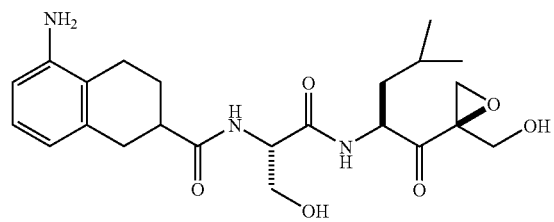 | A |
| ER-807220 | 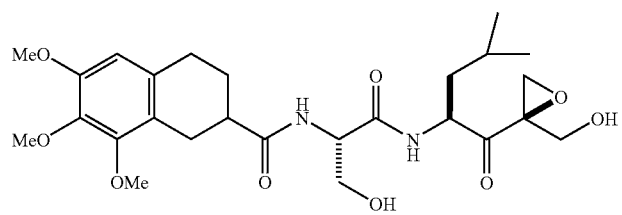 | A |
| ER-807221 | 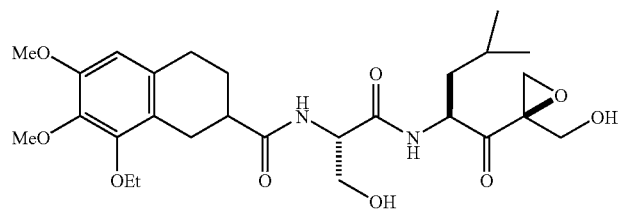 | A |
| ER-807223 | 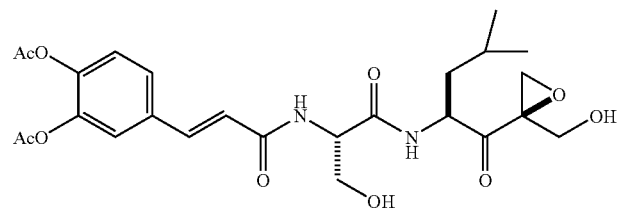 | A |
| ER-807224 | 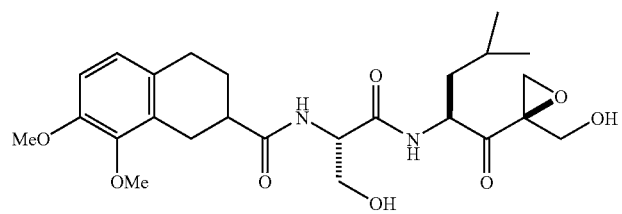 | A |

-continued
| | | |
|---|---|---|
| ER-807241 | 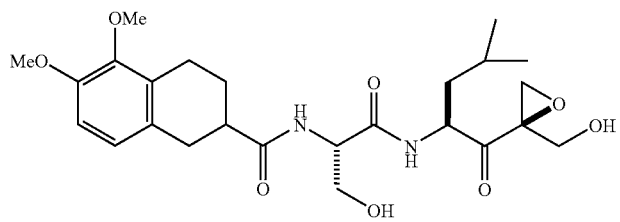 | A |
| ER-807268 | 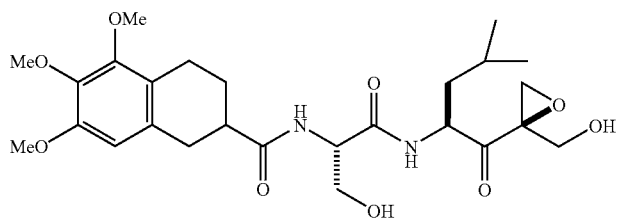 | A |
| ER-807325 | 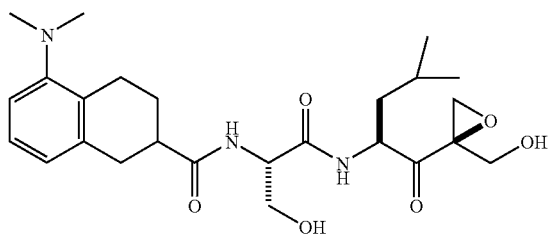 | A |
| ER-807359 | 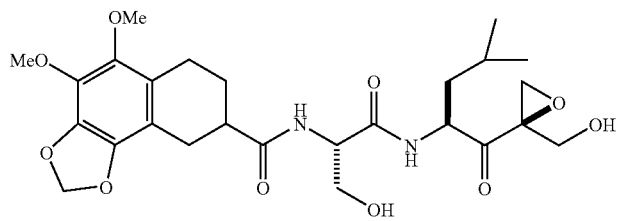 | A |
| ER-807395 | 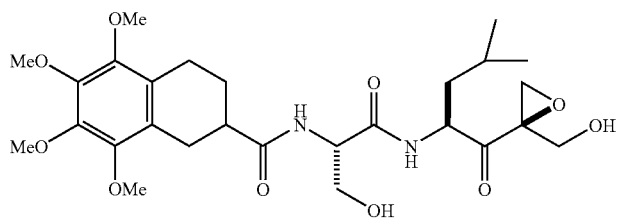 | A |
| ER-807396 | 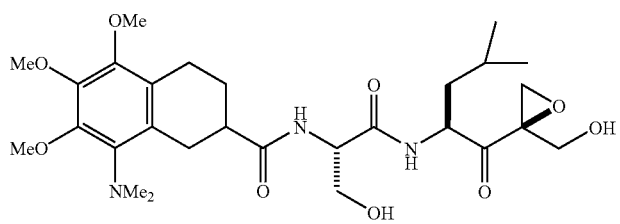 | A |
| ER-807415 | 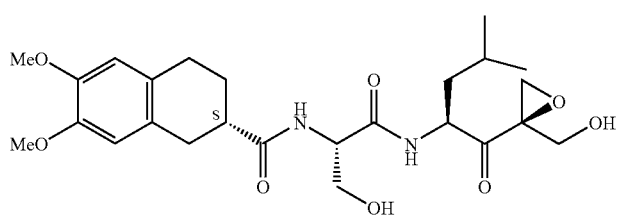 | A |

-continued
| | | |
|---|---|---|
| ER-807416 | 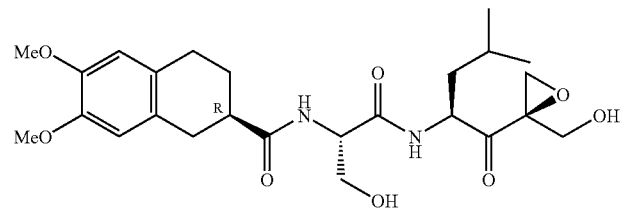 | A |
| ER-807455 | 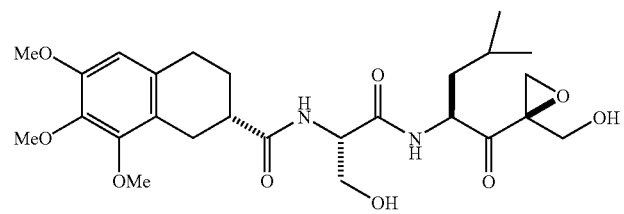 | A |
| ER-807456 | 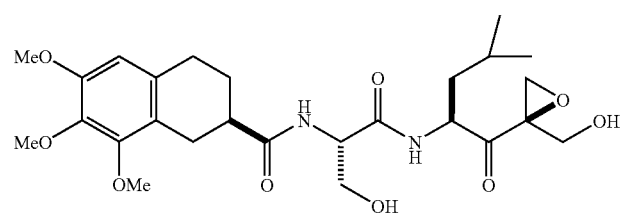 | A |
| ER-807446 | 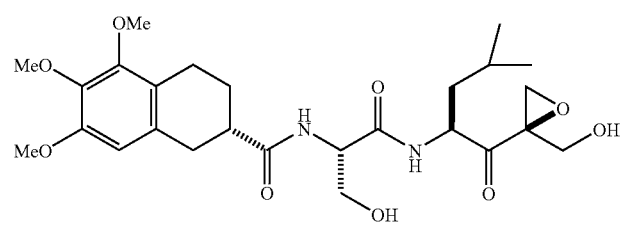 | A |
| | 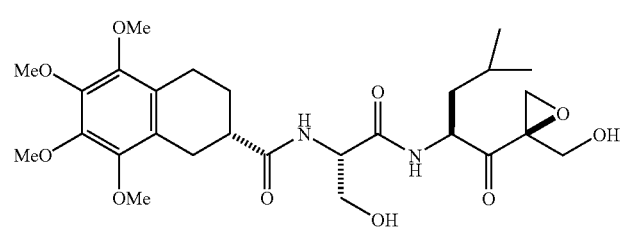 | |
| | 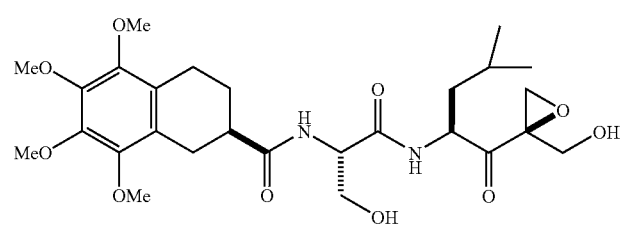 | |
| | 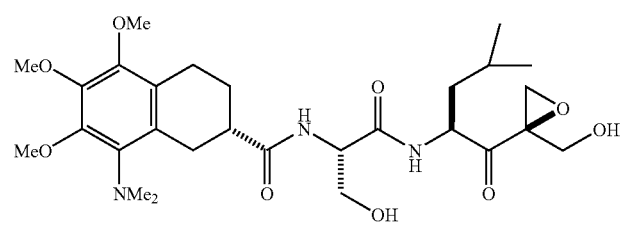 | |

-continued
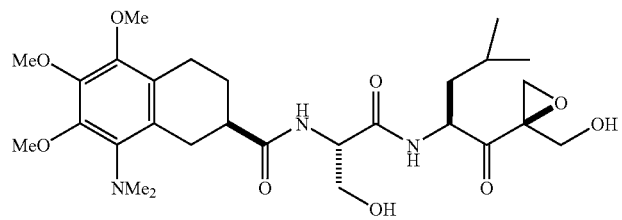
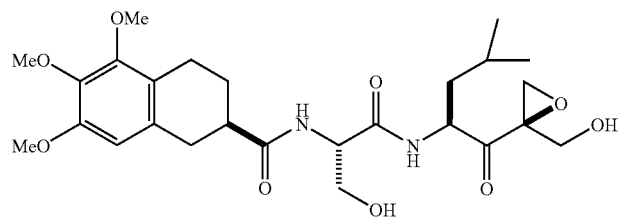
ER-807359
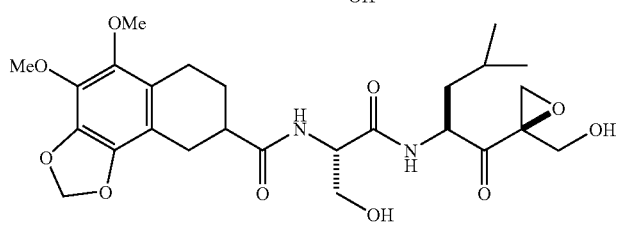
ER-807395
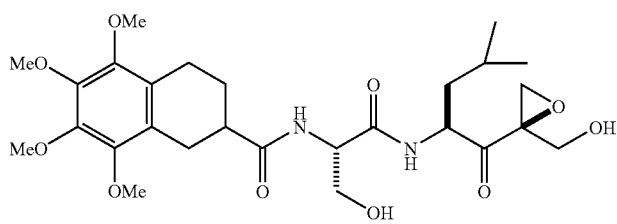
ER-807396
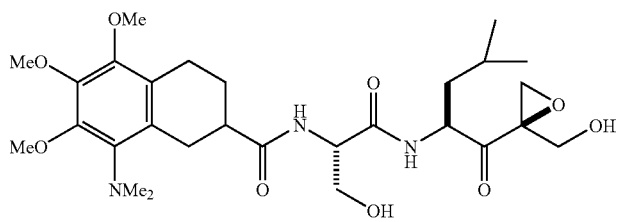
ER-807415
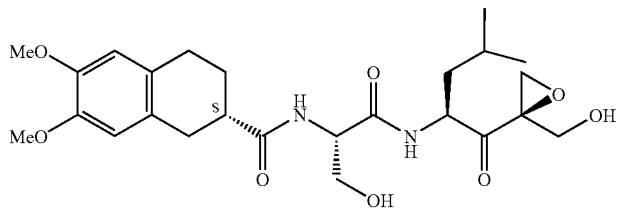
ER-807416
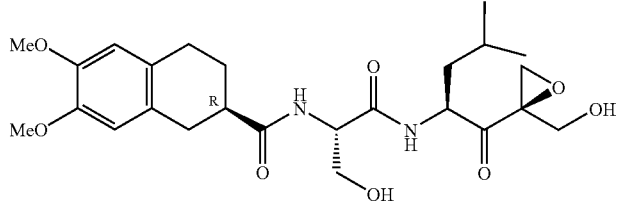

ER-807455 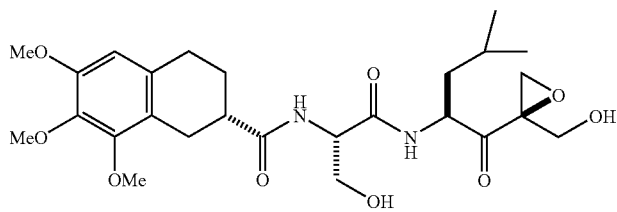
ER-807456 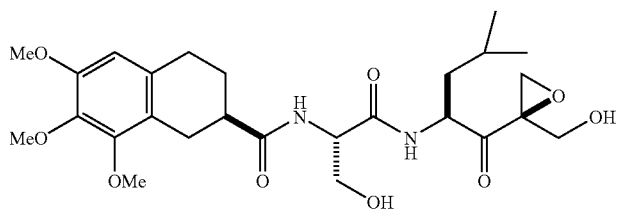
ER-807446 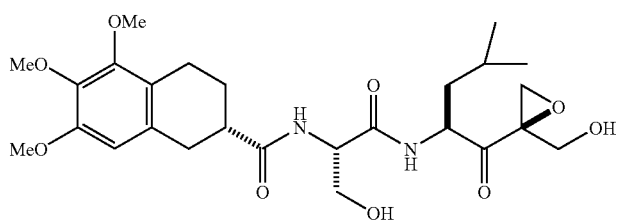
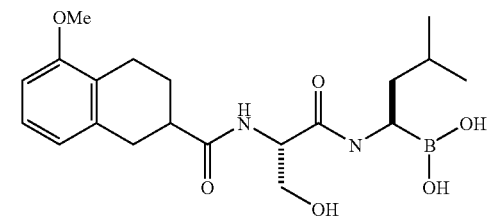
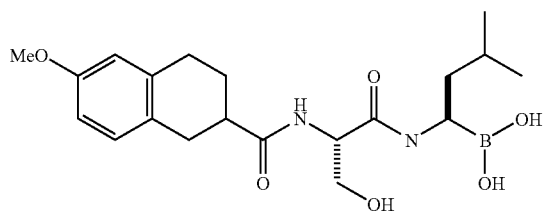
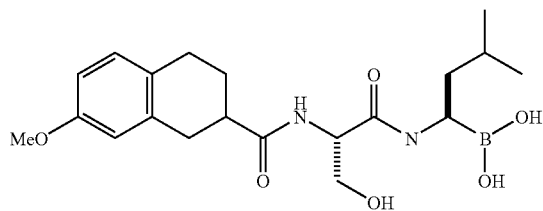
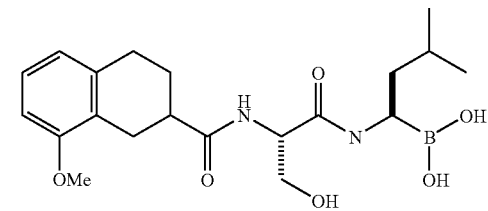

-continued
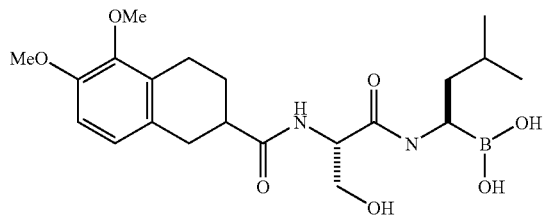
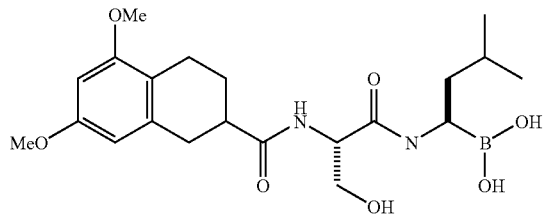
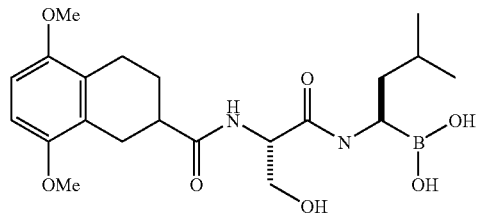
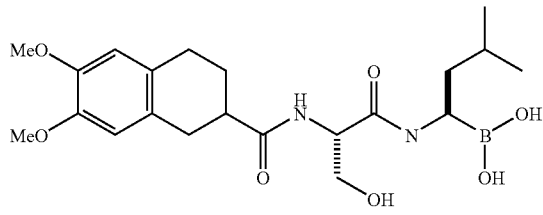
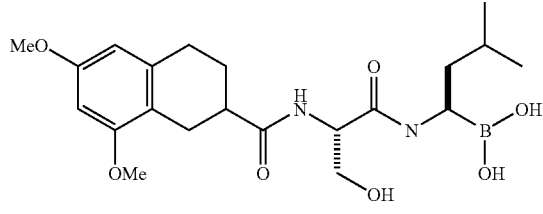
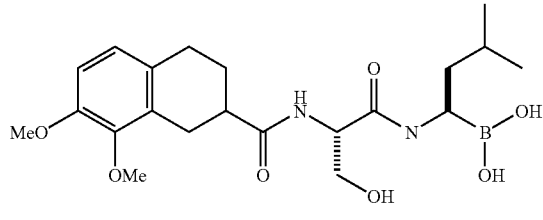
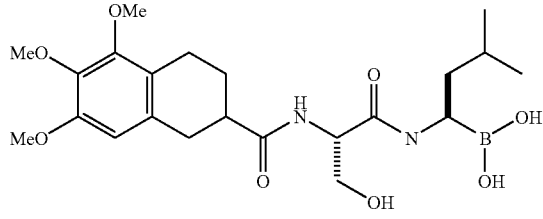

-continued
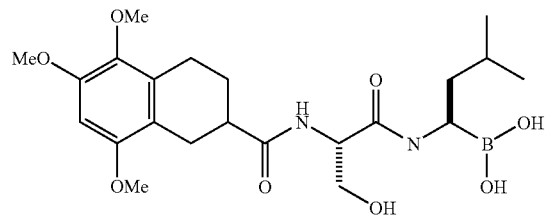
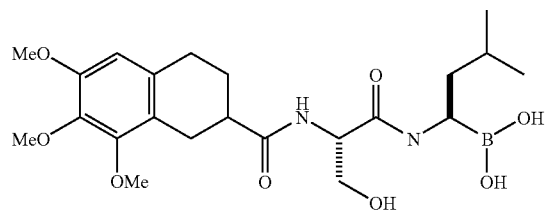
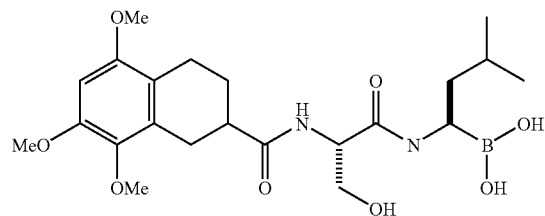
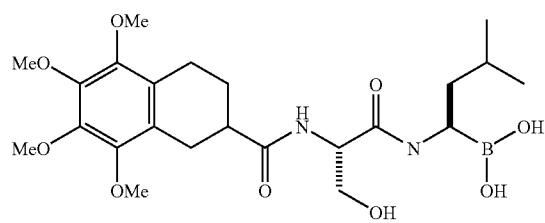
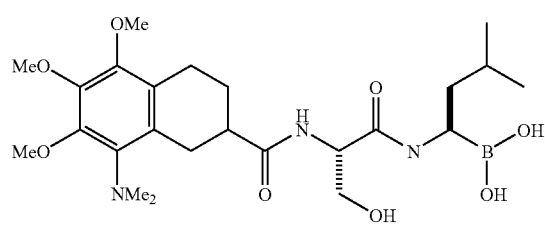
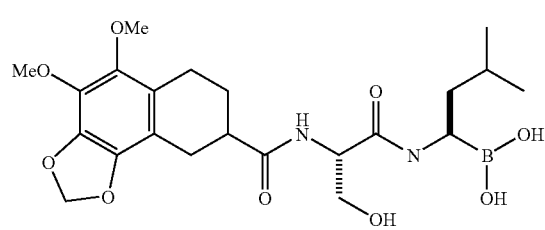
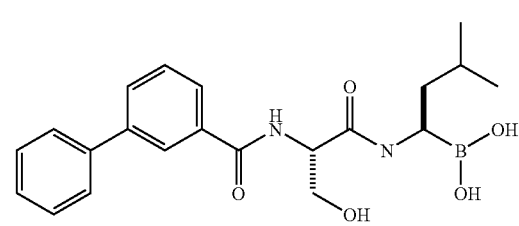

-continued
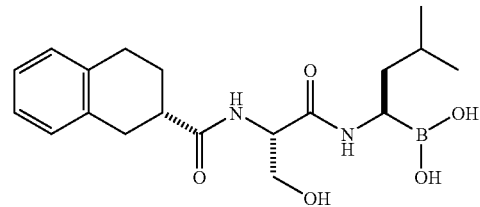
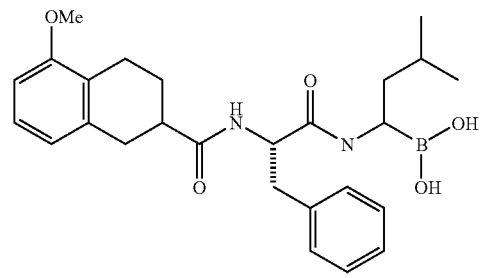
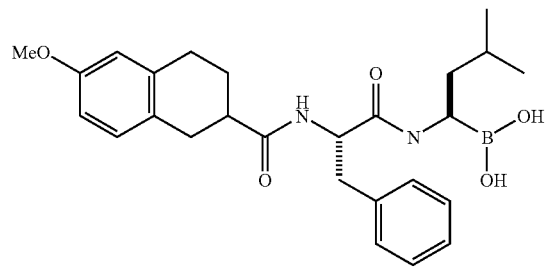
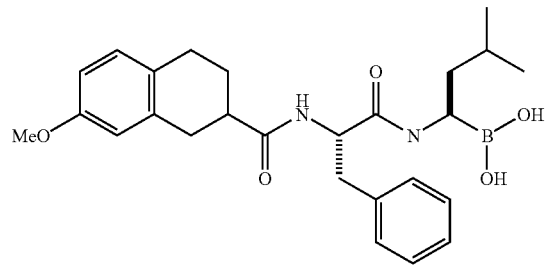
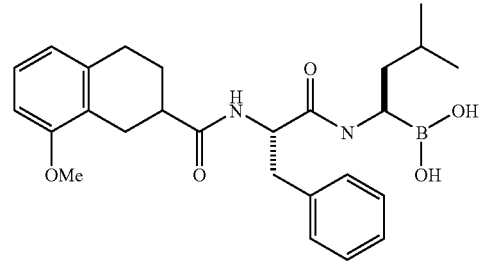
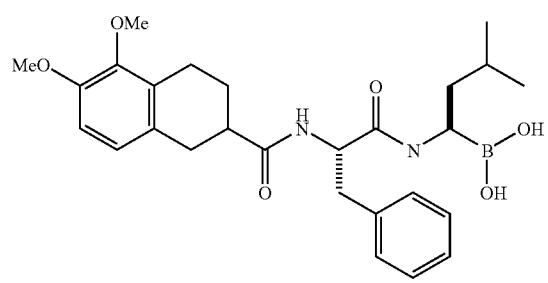

-continued
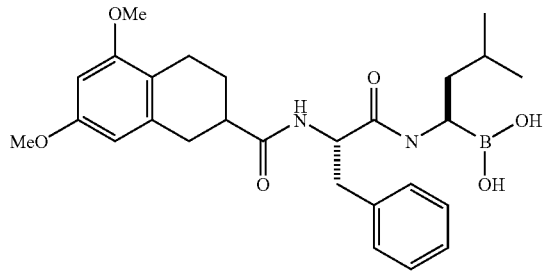
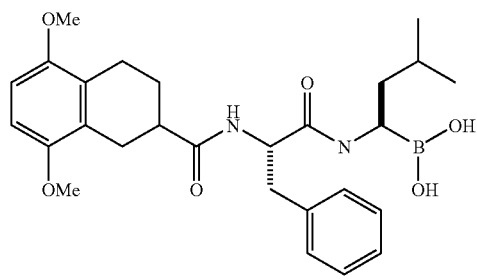
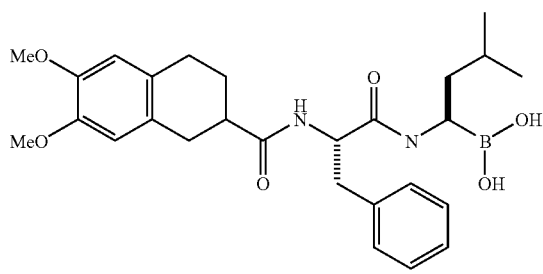
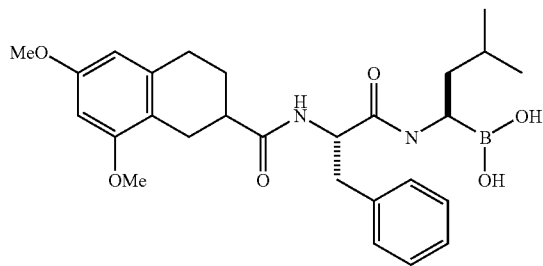
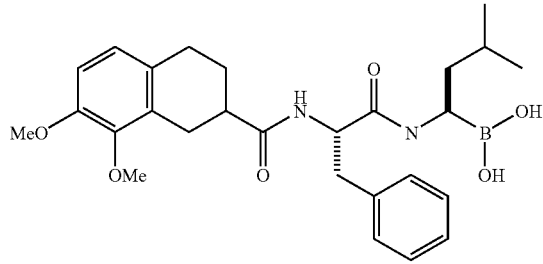

-continued
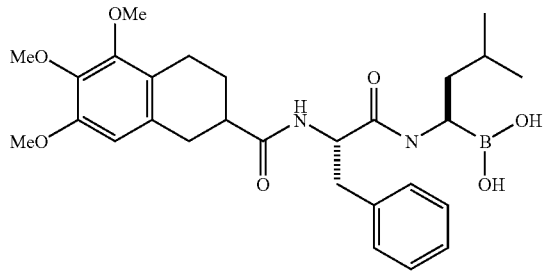
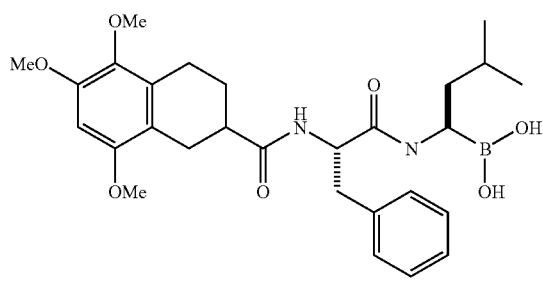
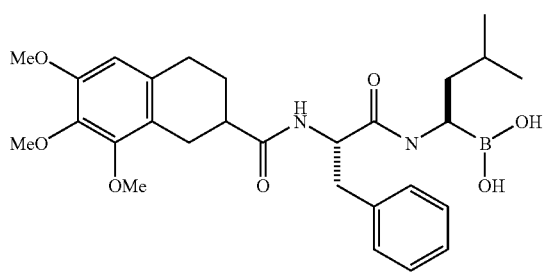
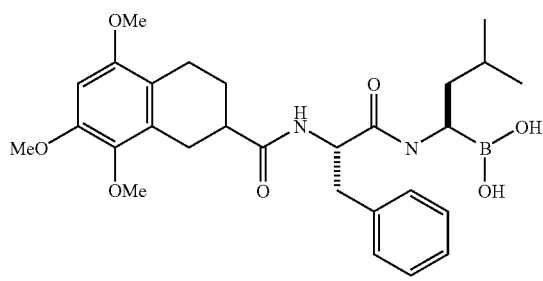
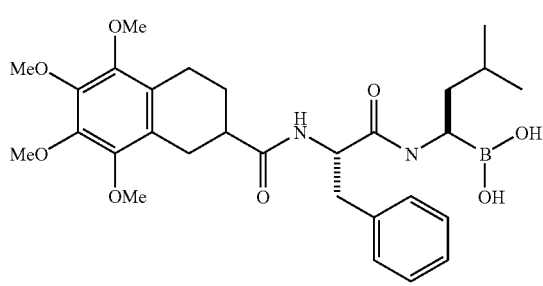

-continued
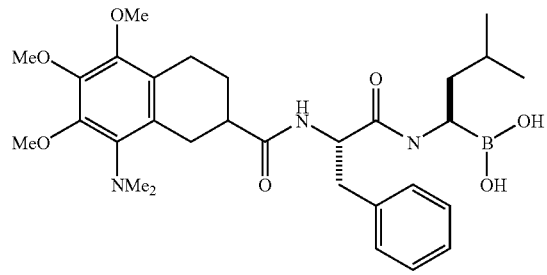
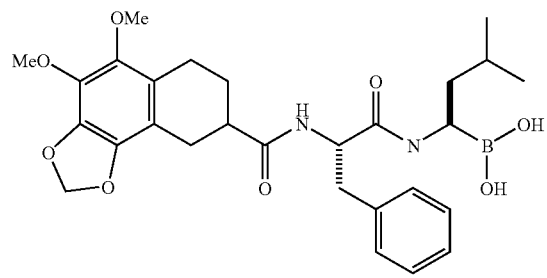
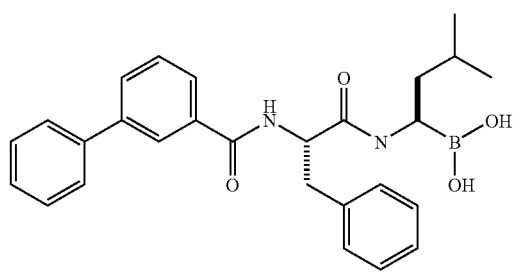
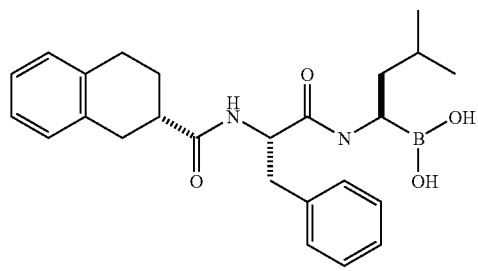
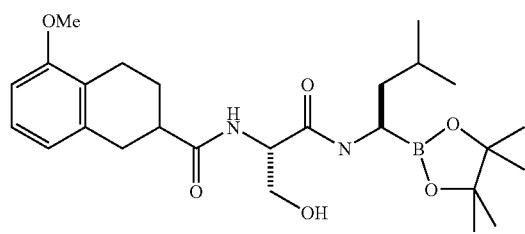
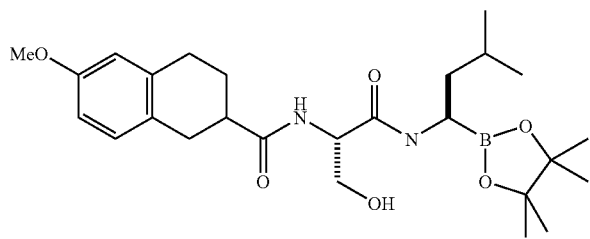

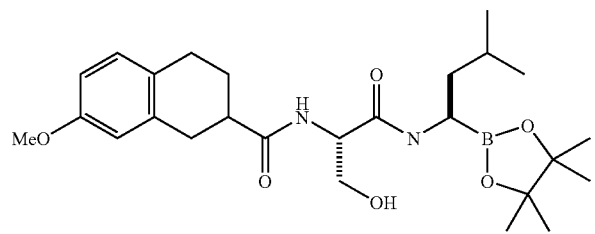
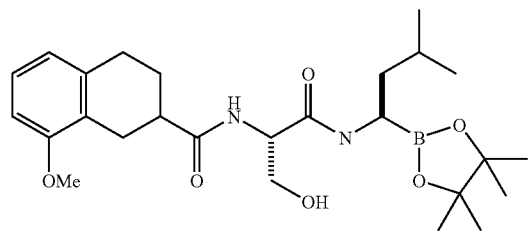
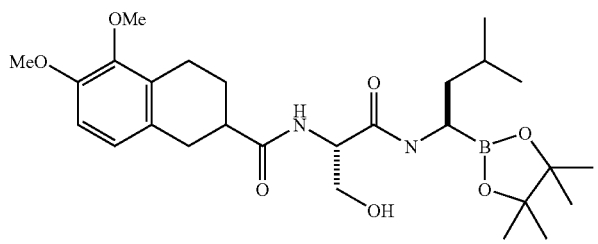
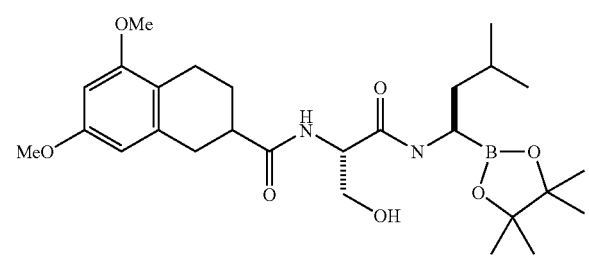
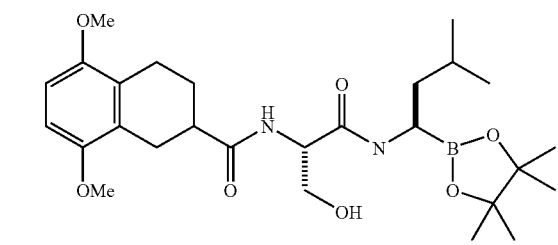
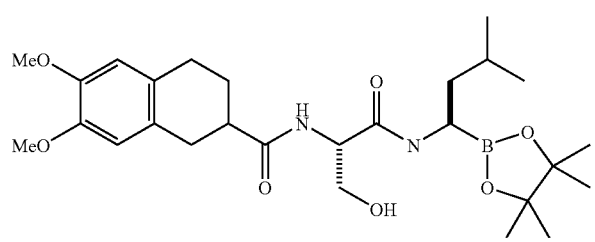

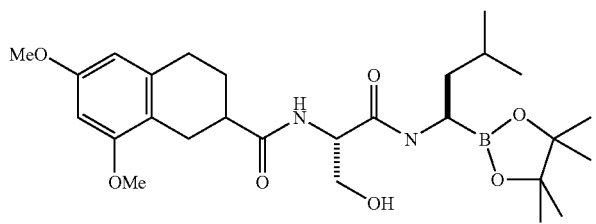
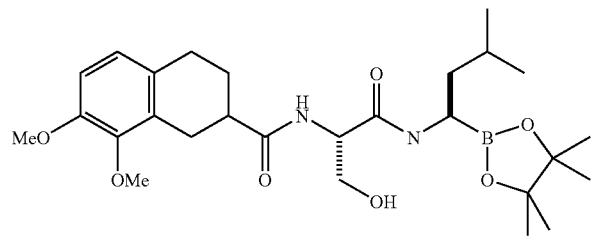
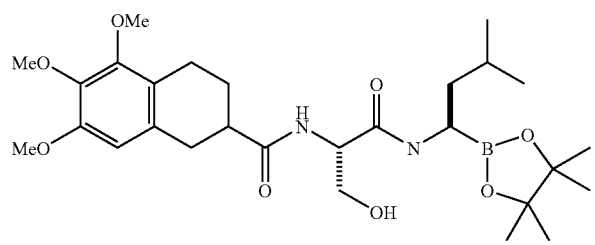
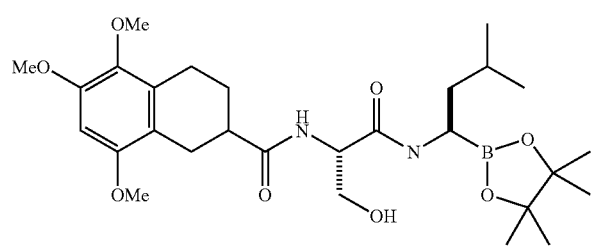
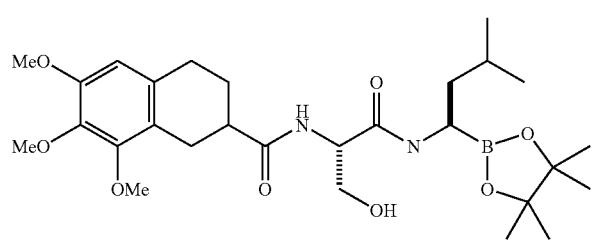
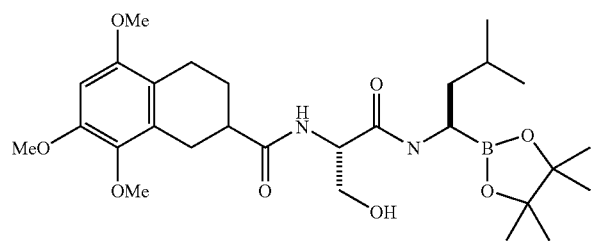

-continued
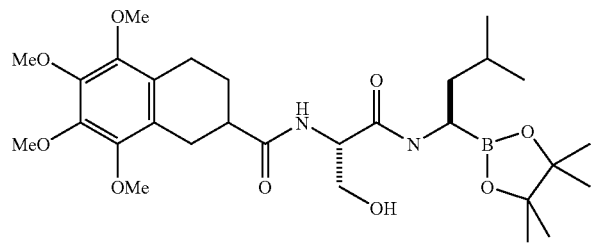
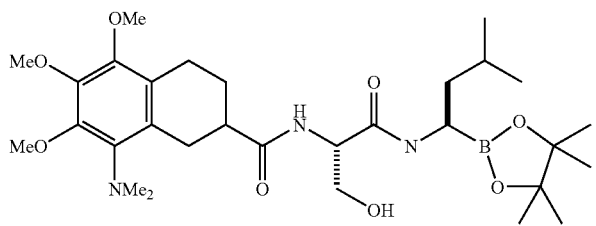
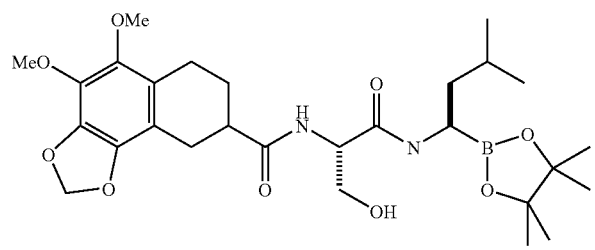
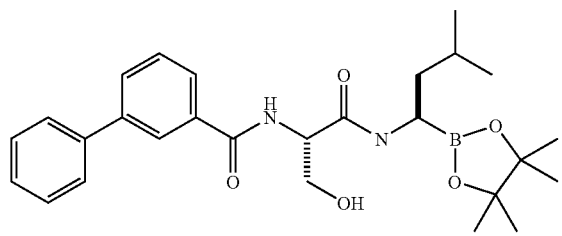
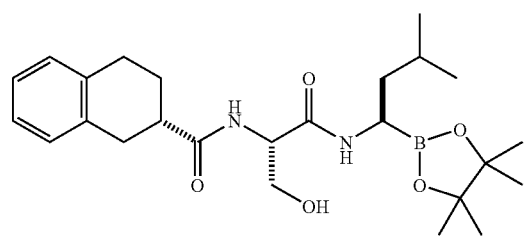
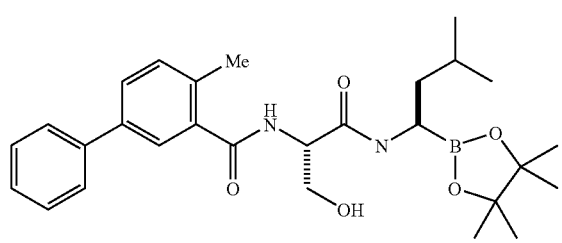

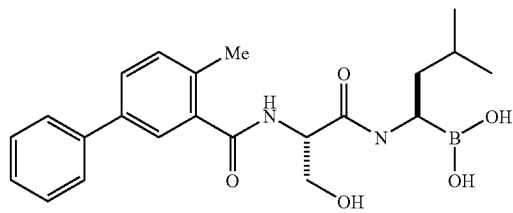
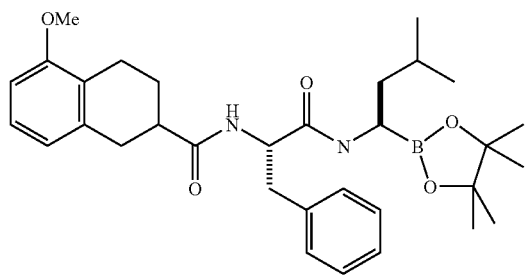
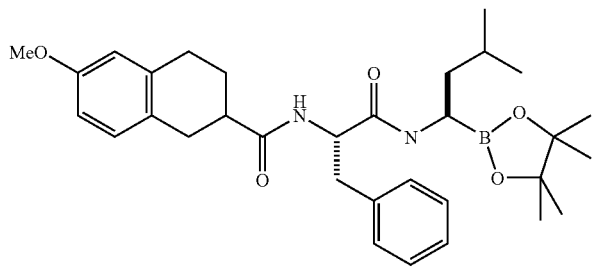
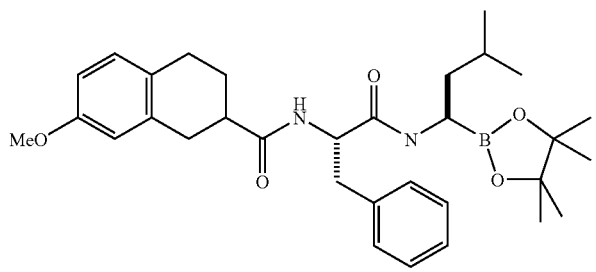
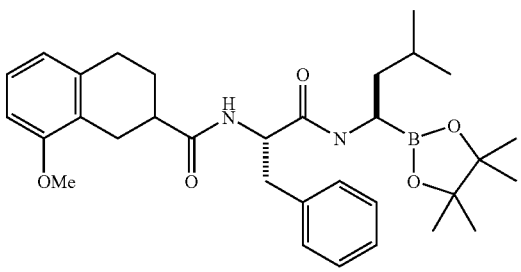
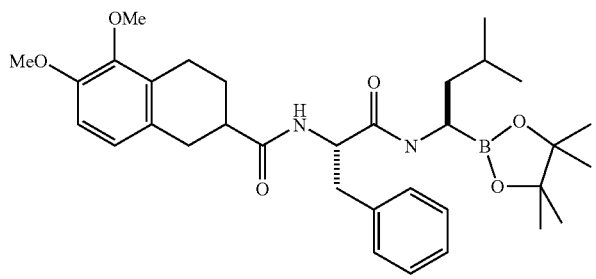

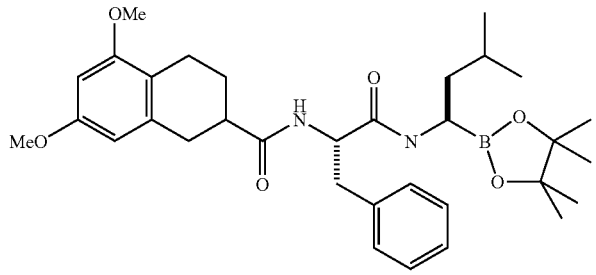
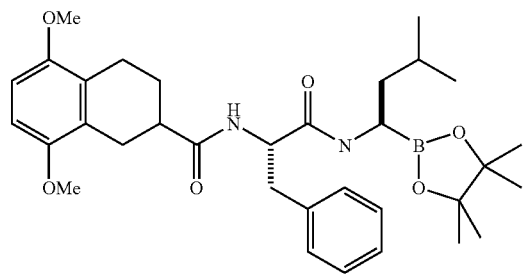
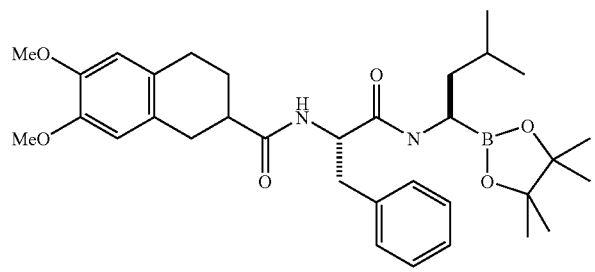
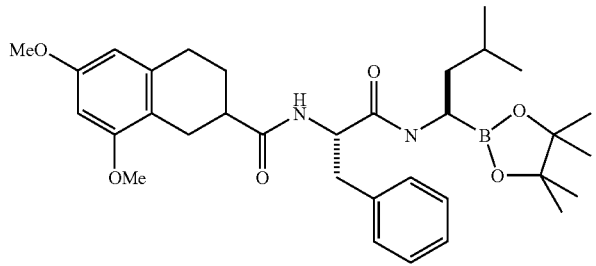
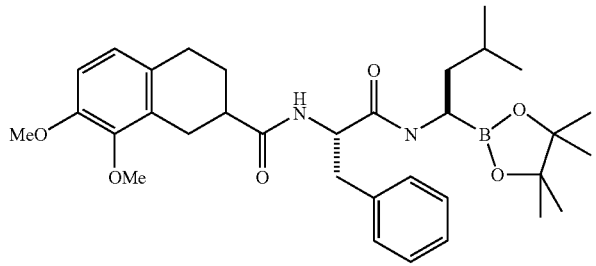

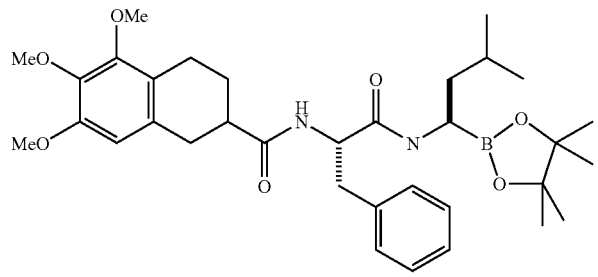
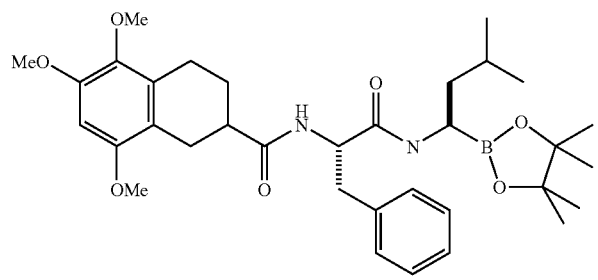
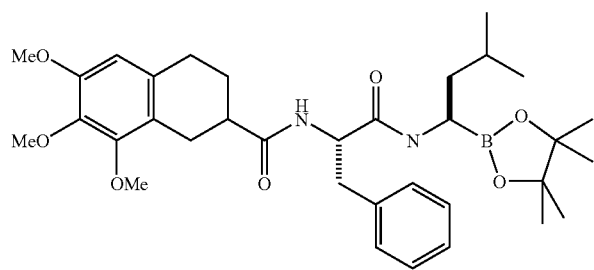
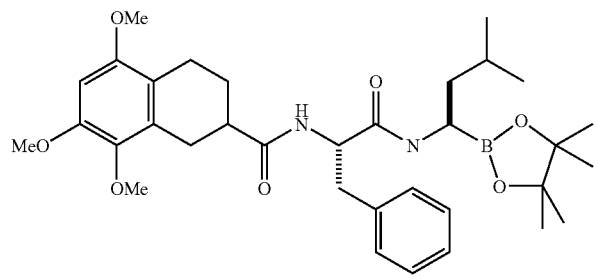
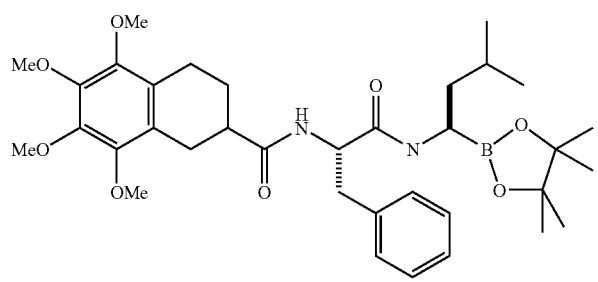

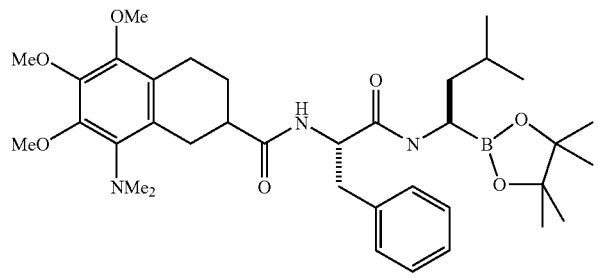
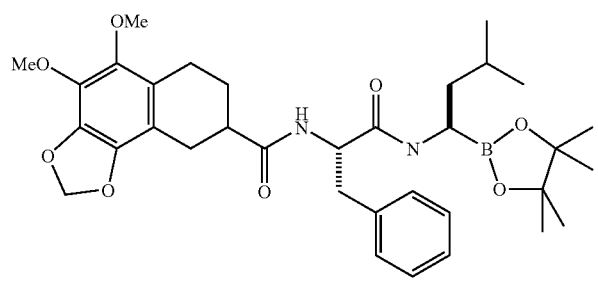
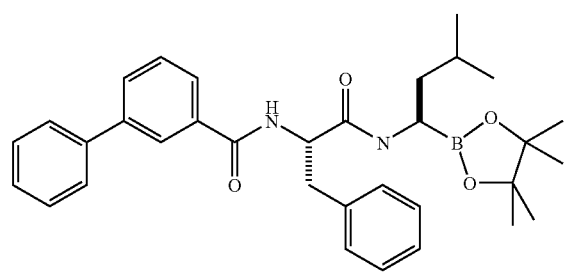
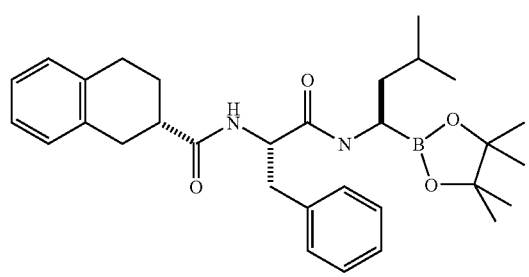
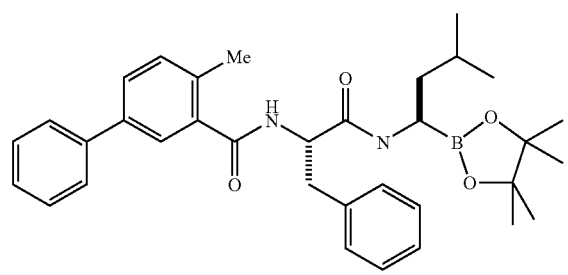

-continued

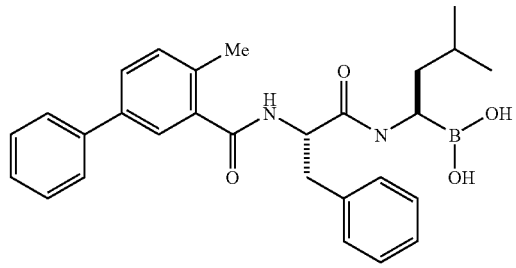

3) Biological Assays:

A) Growth Inhibition of Cultured Cancer Cell Lines

HT-29 human colon adenocarcinoma cells were grown in McCoy's 5A modified medium (GIBCO) supplemented with 10% fetal bovine serum (FBS) and antibiotics. Cells were seeded at $7.5 \times 10^3$ cells/well into 96-well plates, in 100 µl medium. After 3-4 hours at 37° C., 2×-concentrated compounds were added, and cells were incubated at 37° C. One plate was harvested after a 3-day incubation; the other after 4 days. At harvest, media were aspirated, and 100 µl methylene blue (5 mg/ml in 50% ethanol) added to each well. Incubation proceeded at room temperature for 30 minutes, after which the methylene blue is removed, and the wells were washed by immersion in water four times. After plates were air-dried, 100 µl of sarcosine (10 mg/ml in PBS) was added to each well, and plates were agitated for 1-2 hr at room temperature. Absorbance was then measured on a Titertek Multiscan plate-reader at 600 and 405 nm. Corrected data were graphed and compound $IC_{50}$ values calculated.

This procedure has also been extended to NIH:OVCAR-3 human ovarian adenocarcinoma cells, obtained from ATCC, and grown in RPMI-1640 supplemented with 20% FBS, 10 mM HEPES, 1 mM sodium pyruvate, and 10 µg/ml bovine insulin and antibiotics. The assay was modified by starting with $2.25 \times 10^4$ cells/well, since these cells grow less rapidly than the HT-29s.

MDA-MB-435 human breast carcinoma cells were also tested in an analogous assay. Cells were grown in DMEM medium with HEPES, supplemented with 10% FBS and antibiotics, and plated at $7.5 \times 10^3$ cells/well.

B) Cytotoxicity of Quiescent IMR-90 Human Fibroblasts:

As an indicator of undesirable cytotoxicity towards non-cancerous cells, compounds were tested on quiescent IMR-90 normal human fibroblasts. These cells were deprived of serum to halt replication, then treated with test compound for 24 hours. ATP, a marker of cell viability, was then measured in a luciferase-based luminescence assay.

Methods. IMR-90 cells were maintained in MEM medium supplemented with non-essential amino acids, 1 mM sodium pyruvate, glutamine, and 10% FBS, and antibiotics. At the start of the assay, 96-well plates were seeded with $8 \times 10^3$ cells/well in 200 µl medium, and incubated at 37° C. Four days later, cells were washed and medium was replaced with a low serum (0.1% FBS) version of the same medium. Three days later test compound was added, and incubation continues for another 24 hours. Finally, ATP concentration was measured following lysis of cells and addition of luminescent substrate (ATPLite kit, Packard).

C) Inhibition of Proteasome Enzymatic Activity

Assays have been established to measure peptide hydrolyzing enzymatic activities of mammalian proteasomes. These assays were originally adapted from published work (Dubiel et al., *J. Biol. Chem.* 1992; 267:22369; Gardner et al., *Biochem. J.* 2000;346: 447; Hough et al., *J. Biol. Chem.* 1987; 262:8303; Ma et al., *J. Biol. Chem.* 1992; 267:10515; Reidlinger et al., *J. Biol. Chem.* 1997;227: 24899; Rivett et al., *Met. Enzymol.* 1994;244:331; Stein et al., *Biochemistry.* 1996; 35: 3899).

Methods: Purified 20S proteasomes. Chymotrypsin-like proteasome activity employs commercially available 20S proteasomes purified from rabbit skeletal muscle (Calbiochem). The assay relies on the proteasome's intrinsic ability to cleave a conjugated fluorogenic peptide substrate (Suc-Leu-Leu-Val-Tyr-AMC; Calbiochem), releasing the fluorescent product AMC (amidomethylcoumarin). Inhibitor dilutions were first prepared at 4× concentrations in pre-warmed buffer (50 mM Hepes/KOH, 0.5 mM EDTA, pH 7.5; just prior to use, SDS was added to a final concentration of 0.035%, and DTT was added to 5 mM), and then 20S proteasomes were added, also at 4× final concentration, in a total volume of 50 µl per well. Inhibitor, buffer, and 20S proteasomes were pre-incubated together for 15 minutes at 37° C. A 4× solution of substrate was also made with pre-warmed buffer, and 25 µl/well of this substrate was added after the 15 minute incubation. Final reaction volume was 100 µl. The final reaction concentration of proteasomes was 0.5 nM; substrate was 50 µM. The plate was then placed in the fluorimeter, which was pre-equilibrated to 37° C. After 5 minutes, readings were collected every 5 minutes for an hour, using the excitation wavelength of 355 nm and emission wavelength of 460 nm, and kinetic curves were constructed.

Methods: proteasomes in human leukocyte lysates. The peptidyl-glutamyl peptide hydrolyzing (PGPH) activity of proteasomes was also measured. The method reported by Adams et al. (*Cancer Res.* 1999;59:2615) was utilized which relies upon simple cell lysates from human buffy coat leukocytes purified from whole blood. Briefly, washed cell pellets were aliquotted, then lysed with 5 mM EDTA, pH 8.0, frozen on ice, thawed, and centrifuged at 10,000×g. Resulting supernatants were stored at −80°. Titration experiments suggested that the lysate prepared from $7 \times 10^4$ leukocytes gave good activity. Substrate was again a conjugated fluorogenic peptide substrate (Z-Leu-Leu-Glu-AMC; Calbiochem), which also releases the fluorescent product AMC (amidomethylcoumarin) upon hydrolysis.

Methods: proteasomes in intact HT-29 colon carcinoma cells. This assay tests for inhibition of proteasome enzymatic activities in whole HT-29 cells, and uses a cell-permeable peptide substrate coupled to a fluorophore. Specifically, HT-29 cells were plated and grown to confluence overnight in a black 96-well plate with clear bottom. The following morning, media were replaced with 50 mM TRIS-HCl (pH 7.9) with or without proteasome inhibitors. Cells were treated with the inhibitors for 15 min at 37° C. The lipophilic fluorogenic substrate, MeOSuc-Phe-Leu-Phe-AFC (Enzyme Systems Products, Livermore Calif.), was added to a final concentration of 100 μM. Substrate hydrolysis was followed in a fluorimeter for 1 hr, detecting the product 7-amino-4-trifluoromethyl coumarin via its emission at 505 nm after excitation at 400 nm.

D) In Vivo Efficacy

To assess compound efficacy in vivo, MDA-MB-435, a human breast carcinoma, was grown subcutaneously in nude mice. In this model, compound was typically administered intravenously (i.p.), on a Mon-Weds-Fri schedule, for four weeks, beginning 10-13 days after implantation of $1 \times 10^6$ cells. Mice were weighed once weekly, and their tumors were measured by electronic calipers (BioMedic), with volumes calculated according to the formula: $V=0.5 \times 1.33 \pi r^3$, which assumes that xenografts grow as semi-spheres. Exemplary data for ER-805751 and ER-805616 in this model is shown in FIG. 1.

The invention claimed is:

1. A compound having the structure (I):

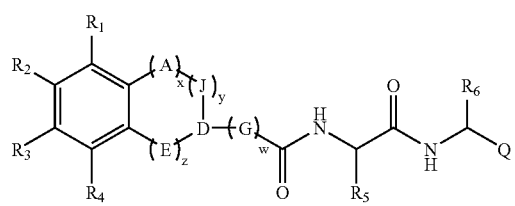

(I)

or pharmaceutically acceptable derivative thereof;
wherein each occurrence of A, J, E, D and G is independently $CR_A$, $CR_A R_B$, C=O, O, S, $NR_A$, or N, wherein each occurrence of $R_A$ and $R_B$ is independently hydrogen, a protecting group, or an aliphatic, alicyclic, heteroaliphatic, heteroalicyclic, aryl or heteroaryl moiety;
A and J, J and D, D and E, and D and G are each independently linked by a single or double bond as valency permits;
w, x, y and z are each independently 0, 1, 2, 3, 4, 5 or 6, but the sum of x, y and z is 2-6;
$R_1$, $R_2$, $R_3$ and $R_4$ are each independently hydrogen, halogen, —CN, —$OR_C$, —$SR_C$, —$NR_C R_D$, —(C=O)$R_C$ or an aliphatic, alicyclic, heteroaliphatic, heteroalicyclic, aryl or heteroaryl moiety, wherein each occurrence of $R_C$ and $R_D$ is independently hydrogen, a protecting group, or an aliphatic, alicyclic, heteroaliphatic, heteroalicyclic, aryl or heteroaryl moiety, or $R_C$ and $R_D$, taken together, form a heteroalicyclic or heteroaryl moiety; or wherein any two adjacent groups $R_1$, $R_2$, $R_3$ and $R_4$, taken together, form an alicyclic or heteroalicyclic moiety, or an aryl or heteroaryl moiety;
$R_5$ and $R_6$ are each independently an aliphatic, alicyclic, heteroaliphatic, heteroalicyclic, aryl or heteroaryl moiety; and Q is an epoxycarbonyl moiety having the structure:

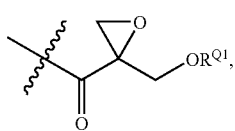

wherein $R^{Q1}$ is hydrogen, an aliphatic, alicyclic, heteroaliphatic, heteroalicyclic, aryl or heteroaryl moiety, an oxygen protecting group or a prodrug moiety.

2. The compound of claim 1, wherein the compound has the structure:

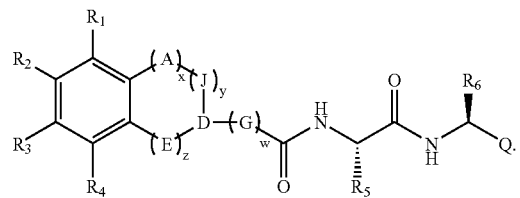

3. The compound of claim 1, wherein $R_5$ is —$CH_2 OR_{5a}$ and the compound has the structure:

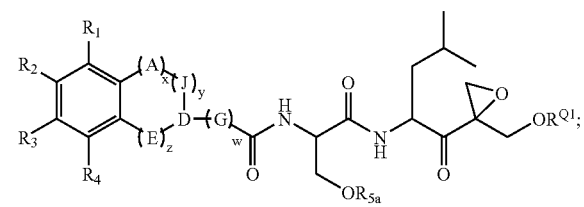

wherein $R_{5a}$ is hydrogen, an aliphatic, alicyclic, heteroaliphatic, heteroalicyclic, aryl or heteroaryl moiety, an oxygen protecting group or a prodrug moiety.

4. The compound of claim 1, wherein $R_5$ is aryl or heteroaryl and the compound has the structure:

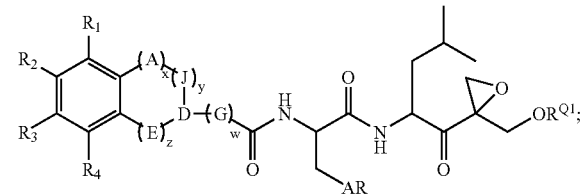

wherein AR is an aryl or heteroaryl moiety.

5. The compound of claim 1, wherein $R_5$ is —$CH_2 NR_{5a} R_b$ or heteroaryl and the compound has the structure:

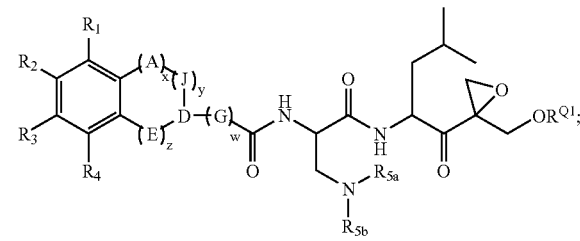

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety.

6. The compound of claim 1, wherein x, y and z are each 1, and A, J, and E are each $CH_2$ and D is CH.

7. The compound of claim 1, wherein G is CH$_2$ and w is 0, 1, or 2.

8. The compound of claim 1, wherein x, y and z are each 1; A, J, and E are each CH$_2$; D is CH; G is CH$_2$ and w is 0, 1, or 2.

9. The compound of claim 1, wherein x, y and z are each 1; A, J, and E are each CH$_2$ and the compound has the structure:

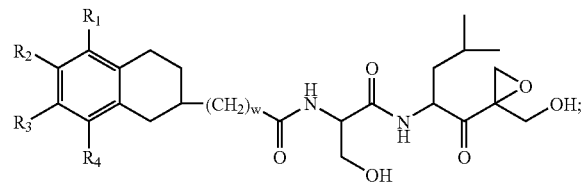

wherein w is 0, 1 or 2; and R$_1$, R$_2$, R$_3$ and R$_4$ are each independently hydrogen, OR$_C$, halogen, or NR$_C$R$_D$, wherein each occurrence of R$_C$ and R$_D$ is independently hydrogen or lower alkyl.

10. The compound of claim 1, wherein x, y and z are each 1; A, J, and E are each CH$_2$ and the compound has the structure:

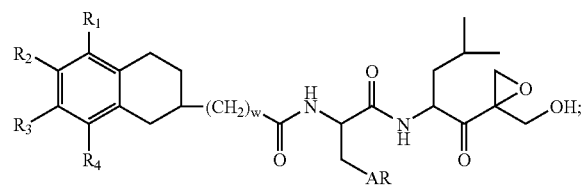

wherein AR is an aryl or heteroaryl moiety; w is 0, 1 or 2; and R$_1$, R$_2$, R$_3$ and R$_4$ are each independently hydrogen, OR$_C$, halogen, or NR$_C$R$_D$, wherein each occurrence of R$_C$ and R$_D$ is independently hydrogen or lower alkyl.

11. The compound of claim 1, wherein x, y and z are each 1; A, J, and E are each CH$_2$, D is CH and the compound has the structure:

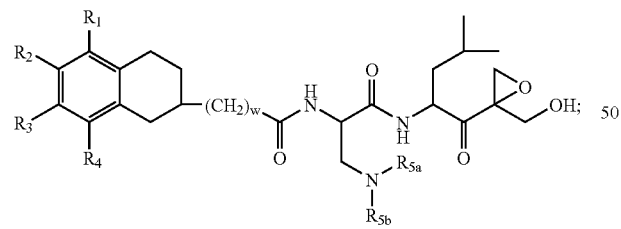

wherein R$_{5a}$ and R$_{5b}$ are each independently hydrogen, a nitrogen protecting group, an aliphatic, alicyclic, heteroaliphatic, heteroalicyclic, aryl or heteroaryl moiety, or a prodrug, or R$_{5a}$ and R$_{5b}$, taken together, form a heteroalicyclic or heteroaryl moiety; w is 0, 1 or 2; and R$_1$, R$_2$, R$_3$ and R$_4$ are each independently hydrogen, OR$_C$, halogen, or NR$_C$R$_D$, wherein each occurrence of R$_C$ and R$_D$ is independently hydrogen or lower alkyl.

12. The compound of claim 1, wherein x, y and z are each 1; A, J, and E are each CH$_2$, D is CH and the compound has the structure:

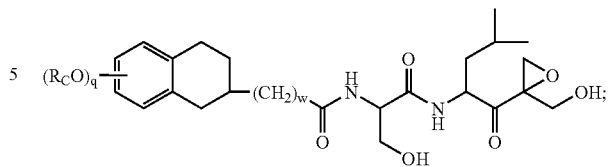

wherein w is 0, 1 or 2, each occurrence of R$_C$ is independently lower alkyl, and q is 0, 1, 2, 3 or 4.

13. The compound of claim 1, wherein x, y and z are each 1; A, J, and E are each CH$_2$, D is CH and the compound has the structure:

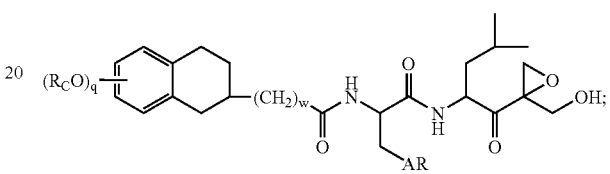

wherein AR is an aryl or heteroaryl moiety; w is 0, 1 or 2, each occurrence of R$_C$ is independently lower alkyl, and q is 0, 1, 2, 3 or 4.

14. The compound of claim 1, wherein x, y and z are each 1; A, J, and E are each CH$_2$, D is CH and the compound has the structure:

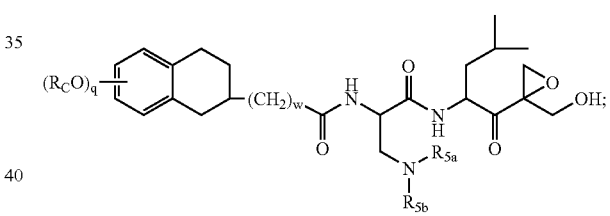

wherein R$_{5a}$ and R$_{5b}$ are each independently hydrogen, a nitrogen protecting group, an aliphatic, alicyclic, heteroaliphatic, heteroalicyclic, aryl or heteroaryl moiety, or a prodrug, or R$_{5a}$ and R$_{5b}$, taken together, form a heteroalicyclic or heteroaryl moiety; w is 0, 1 or 2, each occurrence of R$_C$ is independently lower alkyl, and q is 0, 1, 2, 3 or 4.

15. The compound of claim 1, wherein x, y and z are each 1; A, J, and E are each CH$_2$, D is CH and the compound has the structure:

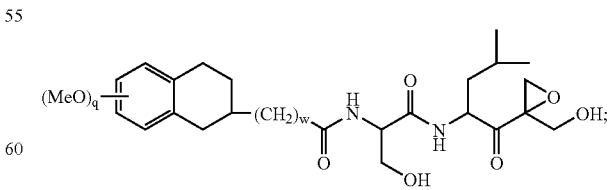

wherein w is 0, 1 or 2; and q is 0, 1, 2, 3 or 4.

16. The compound of claim 1, wherein x, y and z are each 1; A, J, and E are each CH$_2$, D is CH and the compound has the structure:

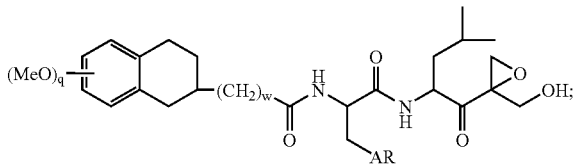

wherein AR is an aryl or heteroaryl moiety; w is 0, 1 or 2; and q is 0, 1, 2, 3 or 4.

17. The compound of claim 1, wherein x, y and z are each 1; A, J, and E are each $CH_2$, D is CH and the compound has the structure:

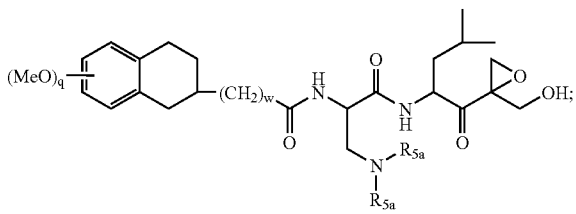

wherein $R_{5a}$ and $R_{5b}$ are each independently hydrogen, a nitrogen protecting group, an aliphatic, alicyclic, heteroaliphatic, heteroalicyclic, aryl or heteroaryl moiety, or a prodrug, or $R_{5a}$ and $R_{5b}$, taken together, form a heteroalicyclic or heteroaryl moiety; w is 0, 1 or 2; and q is 0, 1, 2, 3 or 4.

18. The compound of any one of claims 1, 2, or 3-5, wherein x, y and z are each 1 and A-J-D-E together represent —$CH_2$—$CH_2$—$CH_2$—$CH_2$—.

19. The compound of any one of claims 1, 2, 3-5, wherein x is 0, y and z are each 1, and J-D-E together represent —$CH_2$—$CH_2$—$CH_2$—.

20. The compound of any one of claims 1, 2, 3-5, wherein x is 0, z is 0 and E is absent and J-D together represents —$CH_2$—$CH_2$—.

21. The compound of any one of claims 1, 2, 3-5, wherein x, y and z are each 1 and A-J-D-E together represent —N=CH—CH=N—.

22. The compound of any one of claims 1, 2, 3-5, wherein x, y and z are each 1 and A-J-D-E together represent —$CH_2$—$CH_2$—$CH_2$—$CH_2$— and G is $CH_2$ and w is 0, 1 or 2.

23. The compound of claim 1, wherein $R_1$, $R_2$, $R_3$ and $R_4$ are each independently hydrogen, halogen, protected or unprotected hydroxyl, protected or unprotected thiol, protected or unprotected amino, alkyl, alkoxy, thioalkyl, mono- or di-substituted alkylamino, or wherein any two adjacent groups $R_1$, $R_2$, $R_3$ or $R_4$, taken together are a cycloalkyl, heterocycloalkyl, aryl or heteroaryl moiety,
whereby each of the alkyl moieties is independently substituted or unsubstituted, linear or branched, cyclic or acyclic, and each of the aryl and heteroaryl moieties is independently substituted or unsubstituted.

24. The compound of claim 1, wherein $R_1$, $R_2$, $R_3$ and $R_4$ are each independently hydrogen or lower alkoxy.

25. The compound of claim 1, wherein $R_1$, $R_2$, $R_3$ and $R_4$ are each independently hydrogen or methoxy.

26. The compound of claim 1, wherein $R_1$, $R_2$, $R_3$ and $R_4$ are each methoxy.

27. The compound of claim 1, wherein $R_1$ is hydrogen and each of $R_2$, $R_3$ and $R_4$ are independently lower alkoxy.

28. The compound of claim 1, wherein $R_1$ is hydrogen and each of $R_2$, $R_3$ and $R_4$ are methoxy.

29. The compound of claim 1, wherein $R_5$ is alkyl, cycloalkyl, alkenyl, cycloalkenyl, alkynyl, cycloalkynyl, $C_{1-6}OR_{5a}$, $C_{1-6}NR_{5a}R_{5b}$, aryl or heteroaryl; wherein $R_{5a}$ and $R_{5b}$ are each independently hydrogen, alkyl, alkenyl, alkynyl, cycloalkyl, cycloalkenyl, aryl, heteroaryl, —C($NH_2$)=N($NO_2$), —C(=O)$OR_{5c}$, —C(=O)$R_{5c}$ or a protecting group; wherein $R_{5c}$ is hydrogen, alkyl, alkenyl, alkynyl, aryl or heteroaryl.

30. The compound of any one of claim 1, wherein $R_5$ is alkyl, cycloalkyl, —$CH_2OR_{5a}$, —$CH_2NR_{5a}R_{5b}$, —$CH_2$aryl or —$CH_2$heteroaryl; wherein $R_{5a}$ and $R_{5b}$ are each independently hydrogen, alkyl, alkenyl, alkynyl, cycloalkyl, cycloalkenyl, aryl, heteroaryl, —C($NH_2$)=N($NO_2$), —C(=O)$OR_{5c}$, —C(=O)$R_{5c}$ or a protecting group; wherein $R_{5c}$ is hydrogen, alkyl, alkenyl, alkynyl, aryl or heteroaryl.

31. The compound of claim 1, wherein $R_5$ is alkyl, cycloalkyl, $CH_2OR_{5a}$, $CH_2NR_{5a}R_{5b}$ or substituted or unsubstituted —$CH_2Ph$; wherein $R_{5a}$ and $R_{5b}$ are each independently hydrogen, alkyl, alkenyl, alkynyl, cycloalkyl, cycloalkenyl, aryl, heteroaryl, —C($NH_2$)=N($NO_2$), —C(=O)$OR_{5c}$, —C(=O)$R_{5c}$ or a protecting group; wherein $R_{5c}$ is hydrogen, alkyl, alkenyl, alkynyl, aryl or heteroaryl.

32. The compound of claim 1, wherein $R_5$ is —$CH_2OH$ or benzyl.

33. The compound of claim 1, wherein $R_6$ is alkyl, cycloalkyl, alkenyl, cycloalkenyl, alkynyl, cycloalkynyl, aryl or heteroaryl.

34. The compound of claim 1, wherein $R_6$ is lower alkyl or aryl.

35. The compound of claim 1, wherein $R_6$ is —$CH_2CH(CH_3)_2$.

36. The compound of claim 1, 2, 3 or 4, wherein Q has the structure:

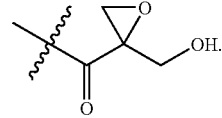

37. The compound of claim 36, wherein Q has the structure:

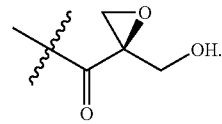

38. A pharmaceutical composition comprising a compound of claim 1; and
a pharmaceutically acceptable carrier or diluent, and optionally further comprising an additional therapeutic agent.

39. The pharmaceutical of claim 38 wherein the compound is present in an amount effective to exert an antiproliferative and/or anticancer effect.

40. The pharmaceutical of claim 38 wherein the compound and the additional therapeutic agent are present in an amount effective to exert an antiproliferative and/or anticancer effect.

41. The pharmaceutical of claim 38 wherein the compound is present in an amount effective to exert an anti-inflammatory effect.

42. The pharmaceutical of claim 38 wherein the compound and the additional therapeutic agent are present in an amount effective to exert an anti-inflammatory effect.

43. A method for treating cancer comprising:
administering to a subject in need thereof a therapeutically effective amount of a compound of claim 1; and
optionally further administering an additional therapeutic agent.

44. The method of claim 43, wherein the method is used to treat prostate, breast, colon, bladder, cervical, skin, testicular, kidney, ovarian, stomach, brain, liver, pancreatic or esophageal cancer or lymphoma, leukemia, or multiple myeloma.

45. The method of claim 43, wherein the cancer is a solid tumor.

46. The compound of claim 2, wherein Q is a moiety having the structure:

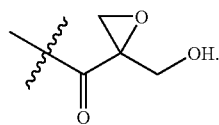

47. The compound of claim 46, wherein Q is a moiety having the structure:

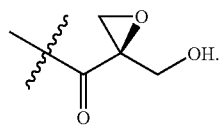

48. The compound of claim 46, wherein Q is a moiety having the structure:

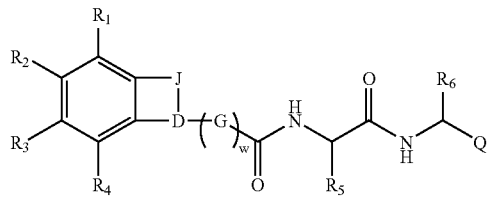

or pharmaceutically acceptable derivative thereof;
wherein each occurrence of J, D and G is independently $CR_A$, $CR_AR_B$, C=O, O, S, $NR_A$, or N, wherein each occurrence of $R_A$ and $R_B$ is independently hydrogen, a protecting group, or an aliphatic, alicyclic, heteroaliphatic, heteroalicyclic, aryl or heteroaryl moiety;
J and D, and D and G are each independently linked by a single or double bond as valency permits;
w is independently 0, 1, 2, 3, 4, 5 or 6,
$R_1$, $R_2$, $R_3$ and $R_4$ are each independently hydrogen, halogen, —CN, —$OR_C$, —$SR_C$, —$NR_CR_D$, —(C=O)$R_C$ or an aliphatic, alicyclic, heteroaliphatic, heteroalicyclic, aryl or heteroaryl moiety, wherein each occurrence of $R_C$ and $R_D$ is independently hydrogen, a protecting group, or an aliphatic, alicyclic, heteroaliphatic, heteroalicyclic, aryl or heteroaryl moiety, or $R_C$ and $R_D$, taken together, form a heteroalicyclic or heteroaryl moiety; or wherein any two adjacent groups $R_1$, $R_2$, $R_3$ and $R_4$, taken together, form an alicyclic or heteroalicyclic moiety, or an aryl or heteroaryl moiety;

$R_5$ and $R_6$ are each independently an aliphatic, alicyclic, heteroaliphatic, heteroalicyclic, aryl or heteroaryl moiety; and Q is an epoxycarbonyl moiety having the structure:

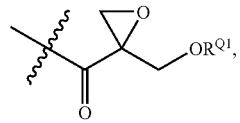

wherein $R^{Q1}$ is hydrogen, an aliphatic, alicyclic, heteroaliphatic, heteroalicyclic, aryl or heteroaryl moiety, an oxygen protecting group or a prodrug moiety.

49. The compound of claim 48, wherein J is $CH_2$ and D is CH.

50. The compound of claim 48, wherein the compound is:

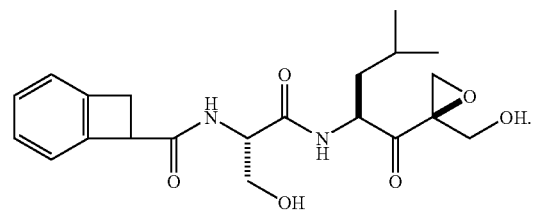

51. The compound of claim 1, wherein the compound is selected from the group consisting of the following compounds:

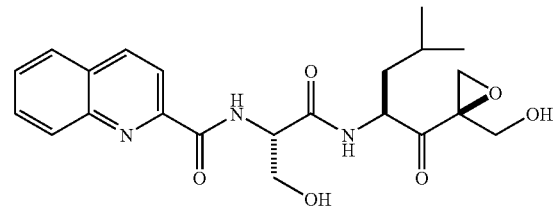

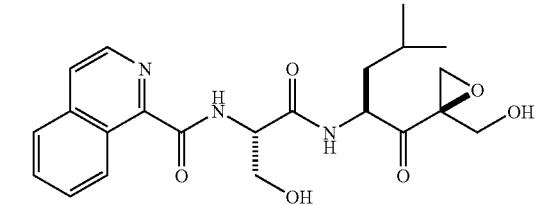

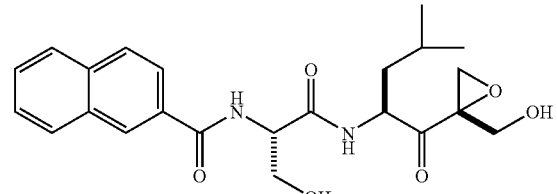

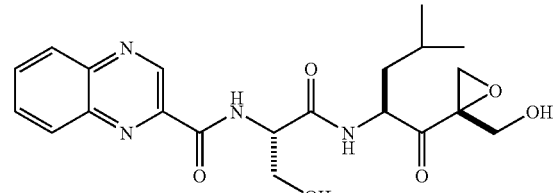

199
-continued
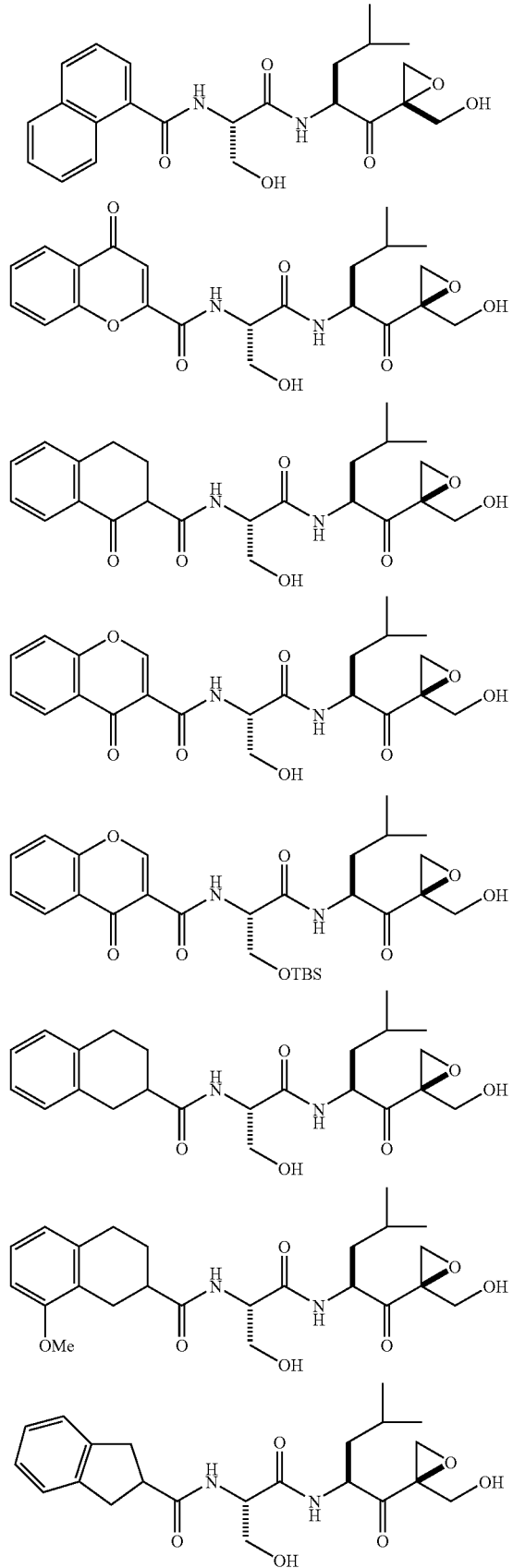
200
-continued
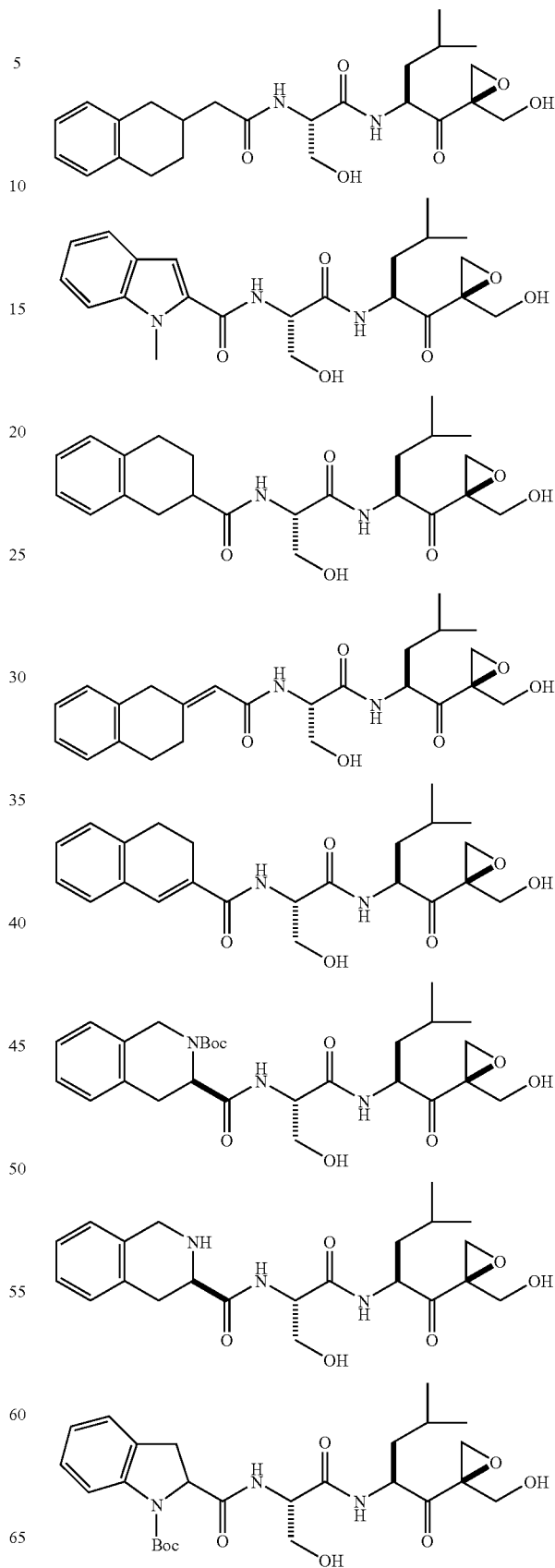

201
-continued
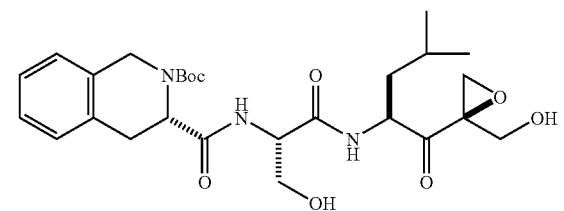
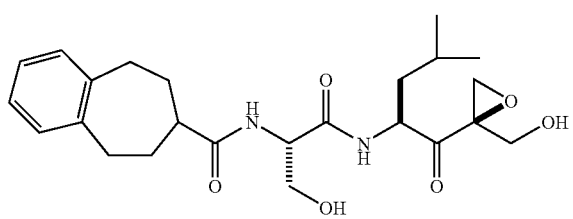
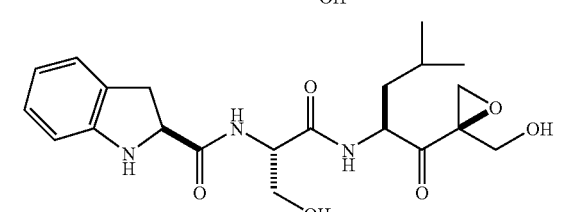
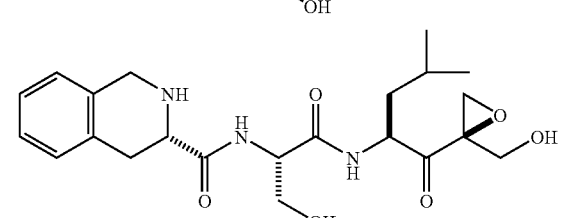
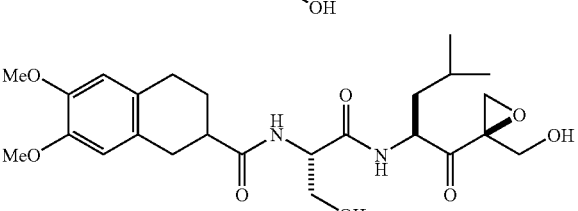
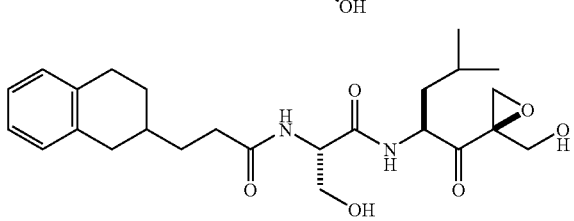
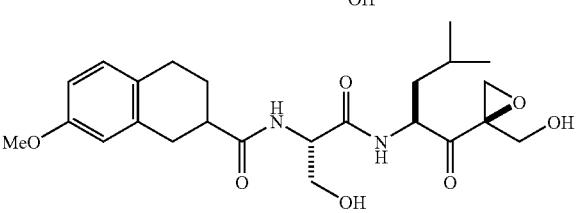
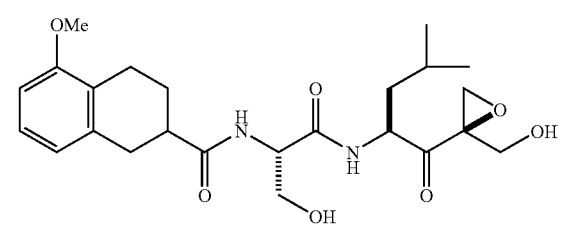
202
-continued
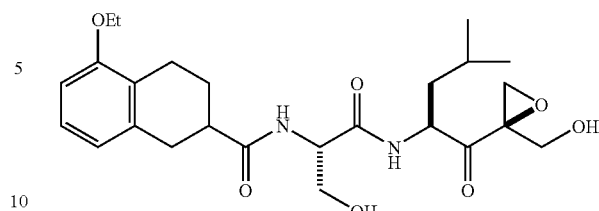
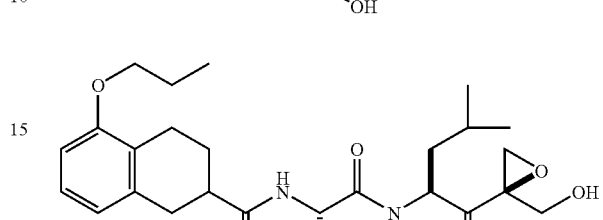
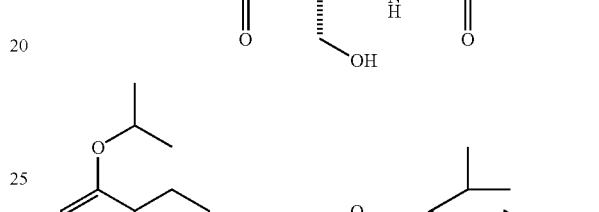
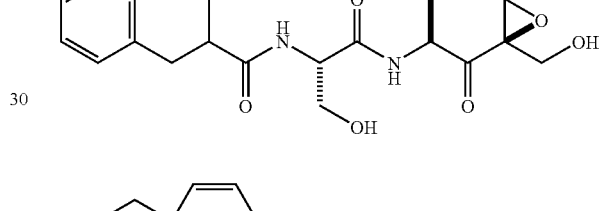
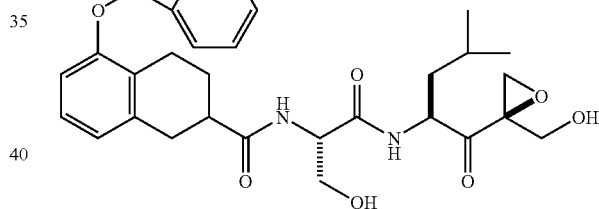
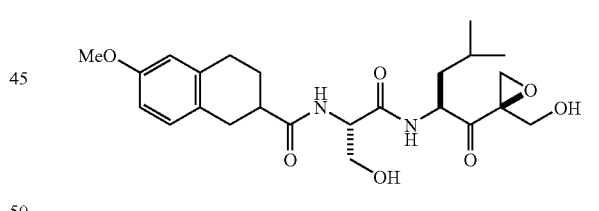
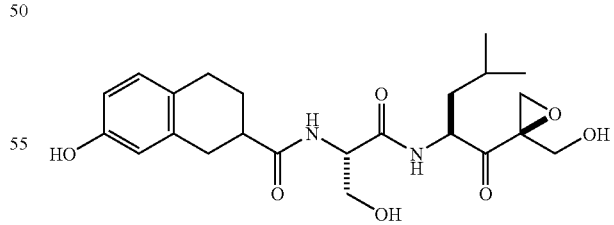
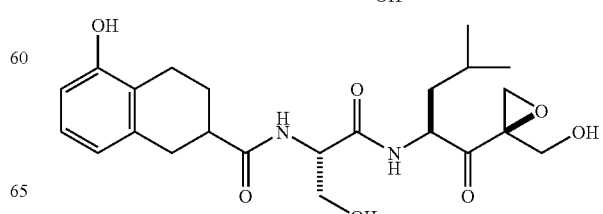

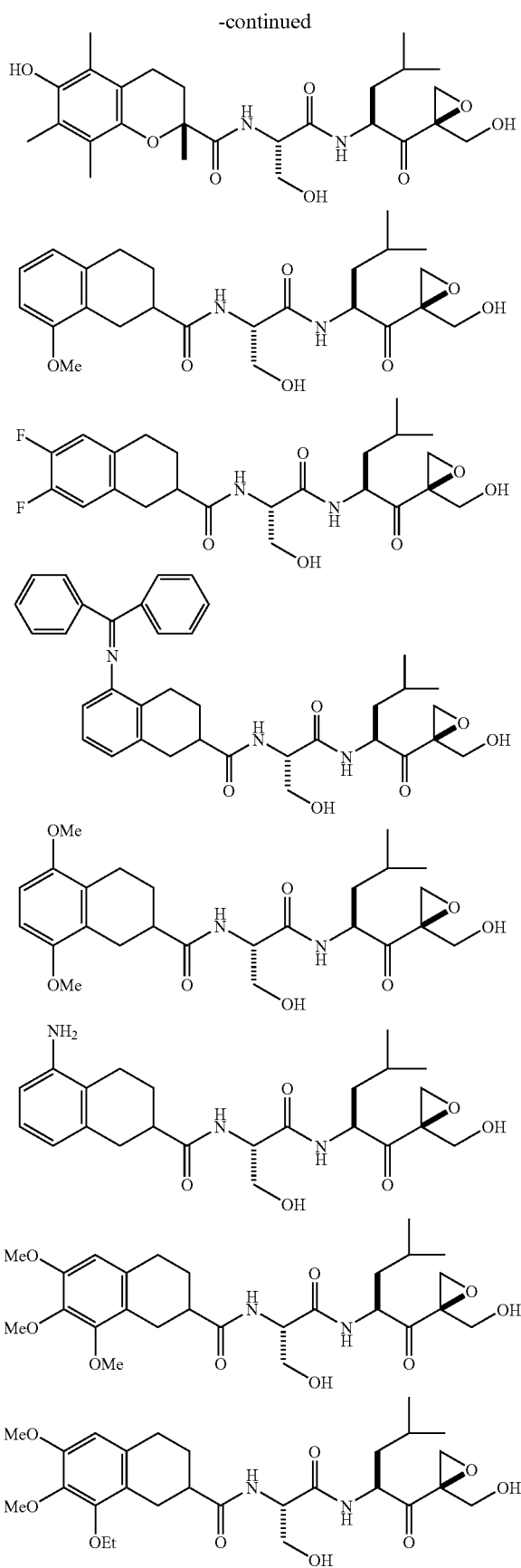

-continued
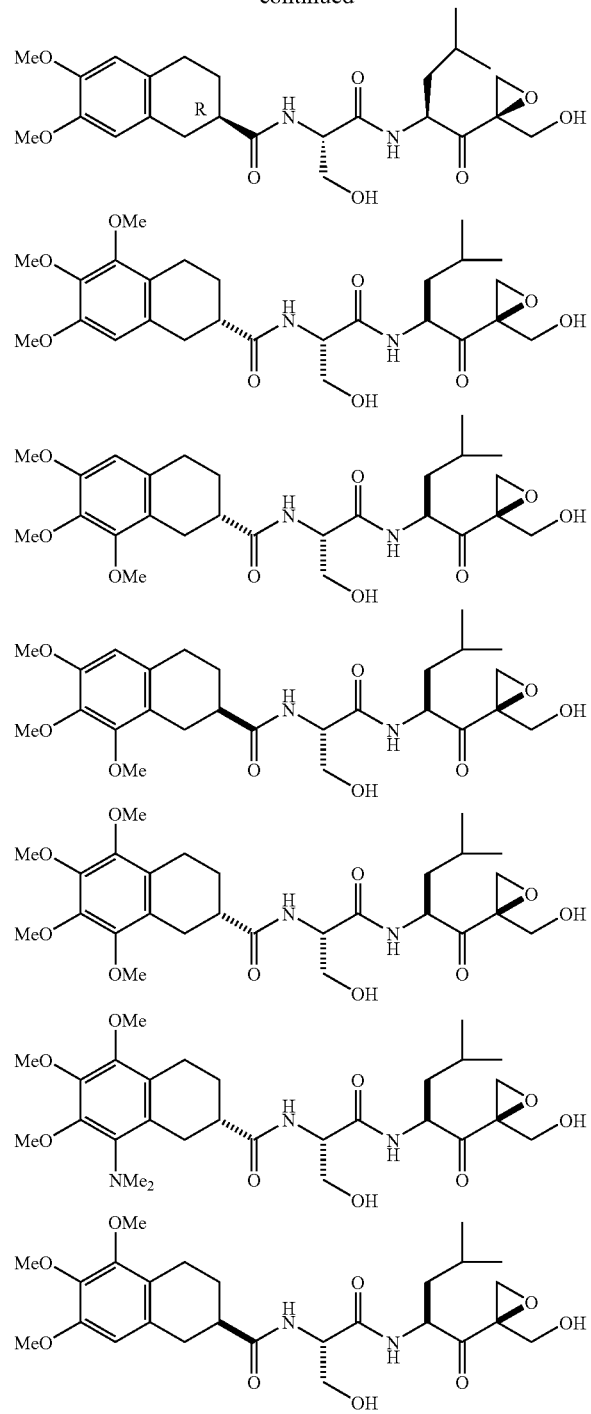
-continued
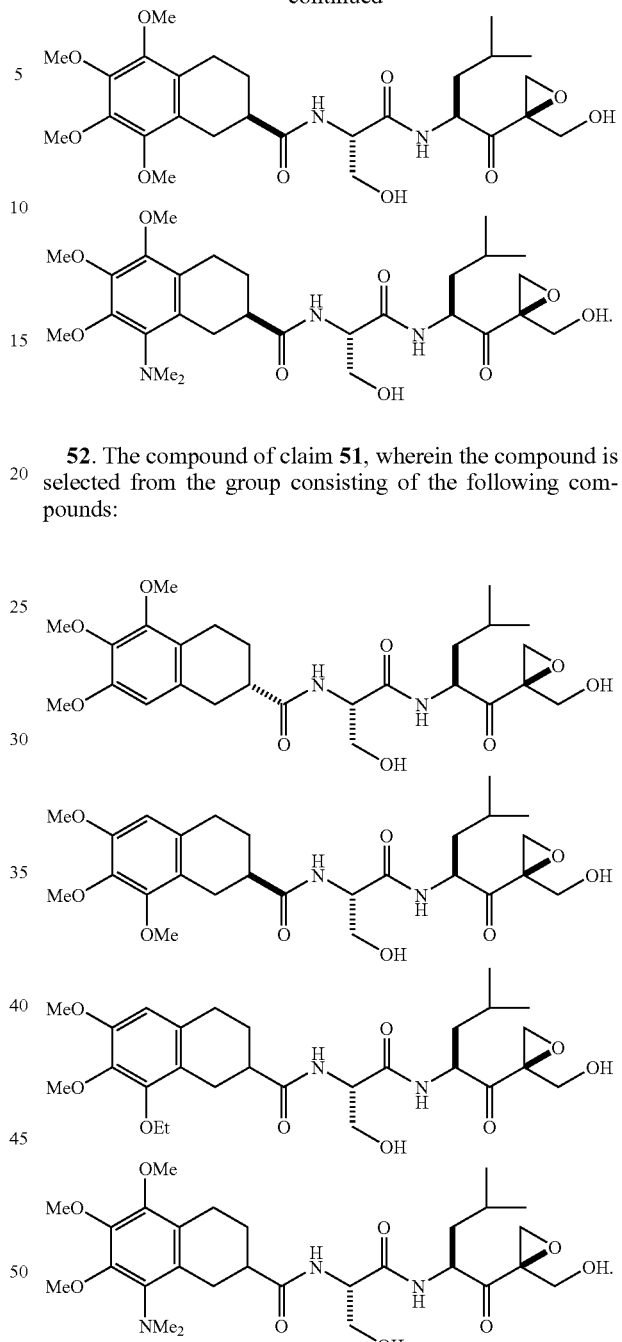
52. The compound of claim 51, wherein the compound is selected from the group consisting of the following compounds:
* * * * *

UNITED STATES PATENT AND TRADEMARK OFFICE
CERTIFICATE OF CORRECTION

PATENT NO.       : 7,524,883 B2
APPLICATION NO.  : 10/501120
DATED            : April 28, 2009
INVENTOR(S)      : Agoulnik et al.

It is certified that error appears in the above-identified patent and that said Letters Patent is hereby corrected as shown below:

In the Claims:
Column 191, Claim 1, Line 43: After "z is 2-6" and before ";"
please add -- and the sum of x and y is 1-6 --

Column 192, Claim 5, Line 46: Please correct "$R_b$" to read -- $R_{5b}$ --
Column 193, Claim 9, Line 7: After "$CH_2$" please add -- , D is CH --
            Claim 10, Line 25: After "$CH_2$" please add -- , D is CH --

Column 195, Claim 17, Line 27: Please correct "$R_{5a}$"

" 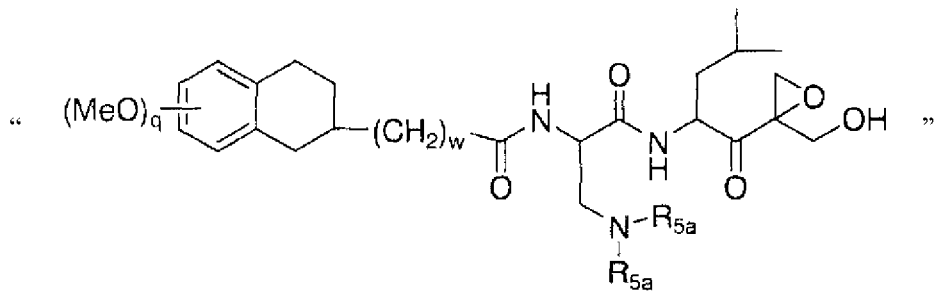 "

to read -- $R_{5b}$ -- as shown in the following compound

-- 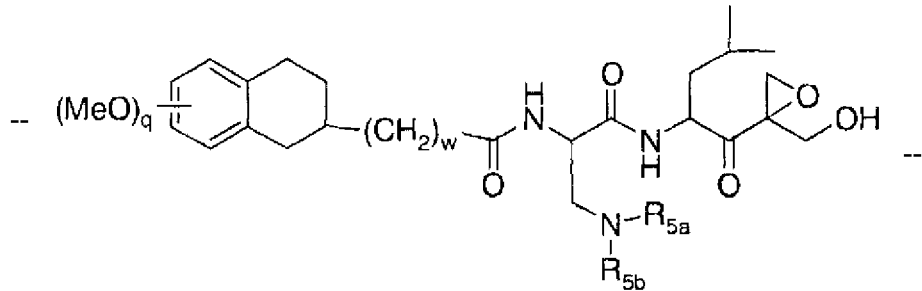 --

UNITED STATES PATENT AND TRADEMARK OFFICE
CERTIFICATE OF CORRECTION

PATENT NO. : 7,524,883 B2
APPLICATION NO. : 10/501120
DATED : April 28, 2009
INVENTOR(S) : Agoulnik et al.

It is certified that error appears in the above-identified patent and that said Letters Patent is hereby corrected as shown below:

Column 195, Claim 18, Line 35: Please correct compound to read
-- —CH$_2$CH$_2$CH-CH$_2$— --
    Claim 19, Line 38: Please correct compound to read
-- —CH$_2$-CH-CH$_2$- --
    Claim 21, Line 44: Please correct compound to read
-- —N=CH-C=N- --
    Claim 22, Line 48: Please correct compound to read
-- —CH$_2$CH$_2$CH-CH$_2$- --

Column 196, Claim 30, Line 11: Please delete "of any one"
    Claim 36, Line 34: Please correct "1, 2, 3 or 4"
to read -- 1 or 2 --

Column 197, Claim 48, Line 35: Please delete "The compound of claim 46, wherein Q is a moiety having the structure" and replace with: -- A compound having the structure --

Signed and Sealed this

Eleventh Day of August, 2009

David J. Kappos
*Director of the United States Patent and Trademark Office*